United States Patent
Chen et al.

(10) Patent No.: US 11,639,355 B2
(45) Date of Patent: May 2, 2023

(54) SUBSTITUTED PYRROLO[3,4-D]IMIDAZOLES AS MDM2-P53 INHIBITORS

(71) Applicants: LUOXIN PHARMACEUTICAL (SHANGHAI) CO., LTD., Shanghai (CN); SHANDONG LUOXIN PHARMACEUTICAL GROUP STOCK CO., LTD., Shandong (CN); MEDSHINE DISCOVERY INC., Jiangsu (CN)

(72) Inventors: Kevin X Chen, Shanghai (CN); Xiaobing Yan, Shanghai (CN); Jianglei Huang, Shanghai (CN); Yuekun Nie, Shanghai (CN); Guoping Hu, Shanghai (CN); Jian Li, Shanghai (CN); Shuhui Chen, Shanghai (CN); Jiaqiang Dong, Shanghai (CN); Tie-Lin Wang, Shanghai (CN)

(73) Assignees: LUOXIN PHARMACEUTICAL (SHANGHAI) CO., LTD., Shanghai (CN); SHANDONG LUOXIN PHARMACEUTICAL GROUP STOCK CO., LTD., Shandong (CN); MEDSHINE DISCOVERY INC., Jiangsu (CN)

( * ) Notice: Subject to any disclaimer, the term of this patent is extended or adjusted under 35 U.S.C. 154(b) by 135 days.

(21) Appl. No.: 16/979,202

(22) PCT Filed: Mar. 12, 2019

(86) PCT No.: PCT/CN2019/077845
§ 371 (c)(1),
(2) Date: Sep. 29, 2020

(87) PCT Pub. No.: WO2019/174576
PCT Pub. Date: Sep. 19, 2019

(65) Prior Publication Data
US 2021/0230164 A1    Jul. 29, 2021

(30) Foreign Application Priority Data

Mar. 12, 2018 (CN) .......................... 201810201653.4
Sep. 30, 2018 (CN) .......................... 201811157824.4

(51) Int. Cl.
C07D 239/22    (2006.01)
C07D 487/04    (2006.01)
A61P 35/00     (2006.01)
C07D 519/00    (2006.01)

(52) U.S. Cl.
CPC ............ C07D 487/04 (2013.01); A61P 35/00 (2018.01); C07D 519/00 (2013.01)

(58) Field of Classification Search
CPC .................................................. C07D 239/52

USPC ........................................................ 544/310
See application file for complete search history.

(56) References Cited

U.S. PATENT DOCUMENTS

2016/0108047 A1*    4/2016    Blank ................. A61K 31/513
                                                        546/273.1

FOREIGN PATENT DOCUMENTS

| CN | 105209467 A | 12/2015 |
|----|-------------|---------|
| CN | 105848682 A | 8/2016 |
| WO | 2013111105 A1 | 8/2013 |
| WO | 2013175417 A1 | 11/2013 |
| WO | 2014191894 A1 | 12/2014 |
| WO | 2015198266 A1 | 12/2015 |
| WO | 2017037579 A1 | 3/2017 |
| WO | 2018161871 A1 | 9/2018 |

OTHER PUBLICATIONS

Jun. 13, 20119 International Search Report issued in International Patent Application No. PCT/CN2019/077845.
(Continued)

*Primary Examiner* — Douglas M Willis
(74) *Attorney, Agent, or Firm* — Houston Beshining Law Office PLLC; Liangang Ye

(57) ABSTRACT

Disclosed is a novel class of MDM2-p53 inhibitor compounds having an imidaxopyrolone structure, and specifically disclosed are compounds represented by formulas (I-1) and (I-2) and pharmaceutically acceptable salts thereof.

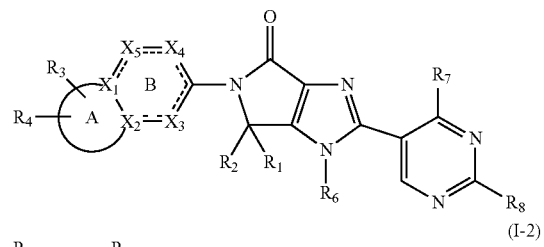

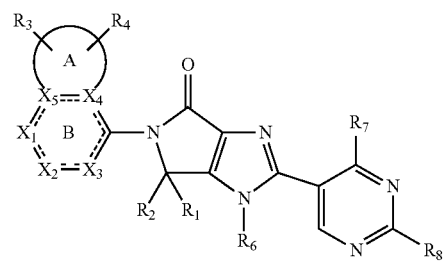

15 Claims, No Drawings

(56) References Cited

OTHER PUBLICATIONS

Jun. 13, 20119 Written Opinion of the International Searching Authority issued in International Patent Application No. PCT/CN2019/077845.
Feb. 18, 2021 extended European Search Report issued in European Patent Application No. 19767751.1.

\* cited by examiner

SUBSTITUTED PYRROLO[3,4-D]IMIDAZOLES AS MDM2-P53 INHIBITORS

CROSS-REFERENCE TO RELATED APPLICATIONS

The present application is a National Stage of International Application No. PCT/CN2019/077845, filed on Mar. 12, 2019, which claims the following right of priority: the Chinese Patent Application No. CN 201810201653.4, date of filing: Mar. 12, 2018; the Chinese Patent Application No. CN 201811157824.4, date of filing: Sep. 30, 2018; the contents of which are incorporated herein by reference in their entireties.

BACKGROUND OF THE INVENTION

Field of the Invention

The present disclosure relates to novel compounds as MDM2-p53 inhibitors, and specifically discloses compounds represented by formulas (I-1) and (I-2) and pharmaceutically acceptable salts thereof. The present disclosure also relates to use of the compounds as MDM2-p53 inhibitors or the pharmaceutical composition thereof in the manufacture of a medicine for treating cancers, bacterial infections, and viral infections.

Description of Related Art p53 is a tumor suppressor and transcription factor that responds to cell stress by activating the transcription of many genes involved in cell cycle arrest, apoptosis, senescence, and DNA repair. Unlike normal cells where p53 activation is caused by uncommon causes, tumor cells are under constant cell stress from various damages including hypoxia and activation of pro-apoptotic oncogenes. Thus, it has a strong selective advantage for the inactivation of p53 pathway in tumors, and it has been proposed that elimination of p53 functions may be a prerequisite for tumor survival. To support this view, three investigative research groups have used mouse models to prove that the lack of p53 functions is a continuing requirement for the maintenance of established tumors. When investigating researchers restore the p53 functions of a p53-inactivated tumor, the tumor regresses.

In 50% of solid tumors and 10% of liquid tumors, p53 is inactivated by mutation and/or deletion. In cancers, other major members of the p53 pathway also undergo genetic or epigenetic changes. MDM2 is an oncogen protein that inhibits p53 functions and is activated by gene amplification at a reported incidence of up to 10%. MDM2 is then inhibited by another tumor suppressor, p14ARF. Changes downstream of p53 are thought to be responsible for at least partially inactivating the p53 pathway in p53WT (p53 wild-type) tumors. To support this concept, some p53WT tumors appear to show reduced apoptotic function, but their ability to undergo cell cycle arrest remains intact. One cancer treatment strategy involves the use of small molecules that bind to MDM2 and counteract its interaction with p53. The MDM2 inhibits p53 activity through three mechanisms: 1) for use as an E3 ubiquitin ligase to promote p53 degradation; 2) binding to a p53 transcription activation domain and blocking the p53 transcription activation domain; and 3) exporting p53 from the nucleus to the cytoplasm. All the three mechanisms will be blocked by counteracting the MDM2-p53 interaction. In particular, such a treatment strategy can be applied to p53WT tumors, and studies using small-molecule MDM2 inhibitors have shown that tumor growth is hopefully reduced in vitro and in vivo. Further, in patients with p53-inactivated tumors, the stabilization of wild-type p53 in normal tissues caused by MDM2 inhibition may allow selective protection of normal tissues from damage by mitotic toxicants.

As used herein, MDM2 means a human MDM2 protein, and p53 means a human p53 protein. It should be noted that human MDM2 can also be referred to as HDM2 or hMDM2.

Research on the treatment of tumors and other diseases based on inhibiting the interaction between p53 and MDM2 has been carried out for many years. There is no drugs against this target on the market, but many molecules have entered different clinical stages. The small-molecule MDM2-p53 inhibitor NVP-HDM201 developed by Novartis has now entered clinical phase II for the treatment of liposarcoma. It is disclosed in patent no. WO 2013111105 and has the following structure:

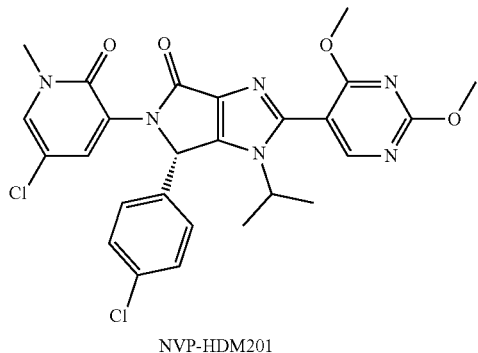 [SMILES: COc1ncc(-c2nc3c(n2C(C)C)[C@H](c2ccc(Cl)cc2)N(c2cc(Cl)cn(C)c2=O)C3=O)c(OC)n1]

NVP-HDM201

The reported data of the NVP-HDM201 molecule shows that it has a good in vitro activity, but its PK properties need to be further improved. In particular, the stability of the drug in mouse liver microsomes is poor; the half-life thereof in mice is short; and the drug plasma exposure is low. The present disclosure modifies some of the readily metabolized sites of the NVP-HDM201 on the basis of the drug molecule, and designs a new class of compounds with longer half-life, higher mouse plasma exposure and better mouse oral bioavailability, and shows a better tumor suppression effect in the mouse model.

BRIEF SUMMARY OF THE INVENTION

The present disclosure provides a compound represented by formula (I-1) or (I-2) or pharmaceutically acceptable salts thereof,

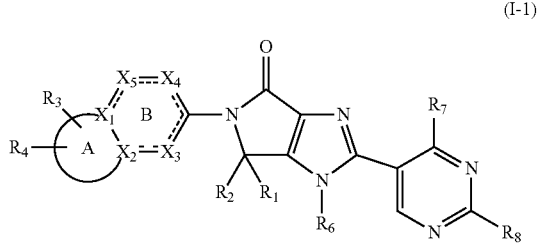

(I-1)

-continued (I-2)

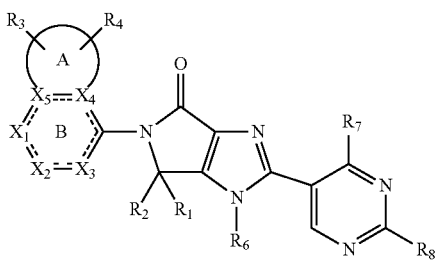

wherein

⚟ is selected from a double bond and a single bond;
ring A is selected from 5-membered heterocycloalkenyl, 5-membered heteroaryl and 5-membered heterocycloalkyl;
ring B is selected from 6-membered aryl and 6-membered heteroaryl;
each $X_1$ is independently selected from C, CH, C($R_5$) and N;
each $X_2$ is independently selected from C, CH, C($R_9$) and N;
each $X_3$ is independently selected from C, CH, C($R_{10}$) and N;
each $X_4$ is independently selected from C, CH, C($R_{11}$) and N;
each $X_5$ is independently selected from C, CH, C($R_{12}$) and N;
each $R_1$ is independently selected from H, $C_{1-3}$ alkyl and $C_{1-3}$ heteroalkyl, wherein the $C_{1-3}$ alkyl and $C_{1-3}$ heteroalkyl are optionally substituted with 1, 2 or 3 $R_a$;
each $R_2$ is independently selected from phenyl and 5-6 membered heteroaryl, wherein the phenyl and 5-6-membered heteroaryl are optionally substituted with 1, 2 or 3 $R_b$;
$R_3$ and $R_4$ are each independently selected from H, halogen, OH, CN, $NH_2$, $C_{1-3}$ alkyl and $C_{1-3}$ heteroalkyl, wherein the $C_{1-3}$ alkyl and $C_{1-3}$ heteroalkyl are optionally substituted with 1, 2 or 3 $R_c$;
$R_5$, $R_9$, $R_{10}$, $R_{11}$ and $R_{12}$ are each independently selected from halogen, OH, CN, $NH_2$, $C_{1-3}$ alkyl and $C_{1-3}$ heteroalkyl, wherein the $C_{1-3}$ alkyl and $C_{1-3}$ heteroalkyl are optionally substituted with 1, 2 or 3 $R_d$;
each $R_6$ is independently selected from $C_{1-6}$ alkyl, $C_{1-6}$ heteroalkyl, $C_{3-6}$ cycloalkyl and 3-6 membered heterocycloalkyl, wherein the $C_{1-6}$ alkyl, $C_{1-6}$ heteroalkyl, $C_{3-6}$ cycloalkyl and 3-6 membered heterocycloalkyl are optionally substituted with 1, 2 or 3 $R_e$;
$R_7$ and $R_8$ are each independently selected from $C_{1-3}$ alkyl-O—, wherein the $C_{1-3}$alkyl-O— is optionally substituted with 1, 2 or 3 halogens;
$R_a$, $R_b$, $R_c$, $R_d$ and $R_e$ are each independently selected from halogen, OH, CN, $NH_2$, $C_{1-3}$ alkyl, $C_{3-5}$ cycloalkyl and $C_{1-3}$ heteroalkyl, wherein the $C_{1-3}$ alkyl, $C_{3-5}$ cycloalkyl and $C_{1-3}$ heteroalkyl are optionally substituted with 1, 2 or 3 R;
R is selected from F, Cl, Br, I, OH, CN, $NH_2$, $NO_2$, $CH_3$, $CH_3CH_2$, $CH_3CH_2CH_2$, $(CH_3)_2CH$, $CF_3$, $CHF_2$, $CH_2F$ and $CH_3O$;
the 5-membered heterocycloalkenyl, 5-membered heteroaryl, 6-membered heteroaryl, 5-membered heterocycloalkyl, $C_{1-3}$ heteroalkyl, $C_{1-6}$ heteroalkyl, 5-6 membered heteroaryl, 3-6 membered heterocycloalkyl comprise 1, 2 or 3 heteroatoms or heteroatomic groups independently selected from N, —NH—, —O—, —S—, —C(=O)—, —C(=S)—, —C(=O)O—, —S(=O)— and —S(=O)$_2$—.

The present disclosure provides a compound represented by formula (I-1) or a pharmaceutically acceptable salt thereof, (I-1)

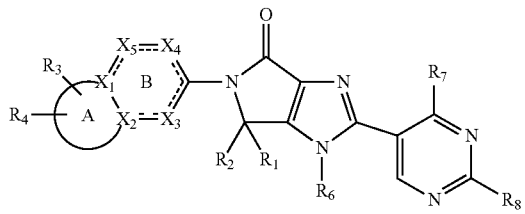

wherein

⚟ is selected from a double bond and a single bond;
ring A is selected from 5-membered heterocycloalkenyl, 5-membered heteroaryl and 5-membered heterocycloalkyl, wherein each the 5-membered heterocycloalkenyl, 5-membered heteroaryl and 5-membered heterocycloalkyl independently comprises 1 or 2 heteroatoms or heteroatomic groups independently selected from N, —NH—, —O—, —S—, —C(=O)—, —C(=S)—, —C(=O)O—, —S(=O)— and —S(=O)$_2$—;
provided that when ring A is selected from 5-membered heteroaryl, then the heteroatoms of the ring A do not simultaneously contain N and —O—;
ring B is selected from 6-membered aryl and 6-membered heteroaryl;
$X_1$ is selected from C, CH, C($R_5$) and N;
$X_2$ is selected from C, CH, C($R_9$) and N;
$X_3$ is selected from C, CH, C($R_{10}$) and N;
$X_4$ is selected from C, CH, C($R_{11}$) and N;
$X_5$ is selected from C, CH, C($R_{12}$) and N;
$R_1$ is selected from H, $C_{1-3}$ alkyl and $C_{1-3}$ heteroalkyl, wherein the $C_{1-3}$ alkyl and $C_{1-3}$ heteroalkyl are each independently and optionally substituted with 1, 2 or 3 $R_a$;
$R_2$ is selected from phenyl and 5-6 membered heteroaryl, wherein the phenyl and 5-6-membered heteroaryl are each independently and optionally substituted with 1, 2 or 3 $R_b$;
$R_3$ and $R_4$ are each independently selected from H, halogen, OH, CN, $NH_2$, $C_{1-3}$ alkyl and $C_{1-3}$ heteroalkyl, wherein the $C_{1-3}$ alkyl and $C_{1-3}$ heteroalkyl are each independently and optionally substituted with 1, 2 or 3 $R_c$;
$R_5$, $R_9$, $R_{10}$, $R_{11}$ and $R_{12}$ are each independently selected from halogen, OH, CN, $NH_2$, $C_{1-3}$ alkyl and $C_{1-3}$ heteroalkyl, wherein the $C_{1-3}$ alkyl and $C_{1-3}$ heteroalkyl are each independently and optionally substituted with 1, 2 or 3 $R_d$;
$R_6$ is selected from $C_{1-6}$ alkyl, $C_{1-6}$ heteroalkyl, $C_{3-6}$ cycloalkyl and 3-6 membered heterocycloalkyl, wherein the $C_{1-6}$ alkyl, $C_{1-6}$ heteroalkyl, $C_{3-6}$ cycloalkyl and 3-6 membered heterocycloalkyl are each independently and optionally substituted with 1, 2 or 3 $R_e$;
$R_7$ and $R_8$ are each independently selected from $C_{1-3}$ alkyl-O—, wherein the $C_{1-3}$ alkyl-O— is optionally substituted with 1, 2 or 3 halogens;
$R_a$, $R_b$, $R_c$, $R_d$ and $R_e$ are each independently selected from halogen, OH, CN, $NH_2$, $C_{1-3}$ alkyl, $C_{3-5}$ cycloalkyl and $C_{1-3}$ heteroalkyl, wherein the $C_{1-3}$ alkyl, $C_{3-5}$ cycloalkyl and $C_{1-3}$ heteroalkyl are each independently and optionally substituted with 1, 2 or 3 R;
R is selected from F, Cl, Br, I, OH, CN, $NH_2$, $NO_2$, $CH_3$, $CH_3CH_2$, $CH_3CH_2CH_2$, $(CH_3)_2CH$, $CF_3$, $CHF_2$, $CH_2F$ and $CH_3O$;

each the 6-membered heteroaryl, C$_{1-3}$ heteroalkyl, C$_{1-6}$ heteroalkyl, 5-6 membered heteroaryl and 3-6 membered heterocycloalkyl independently comprises 1, 2 or 3 heteroatoms or heteroatomic groups independently selected from N, —NH—, —O—, —S—, —C(=O)—, —C(=S)—, —C(=O)O—, —S(=O)— and —S(=O)$_2$—.

The present disclosure provides a compound represented by formula (I-2) or a pharmaceutically acceptable salt thereof,

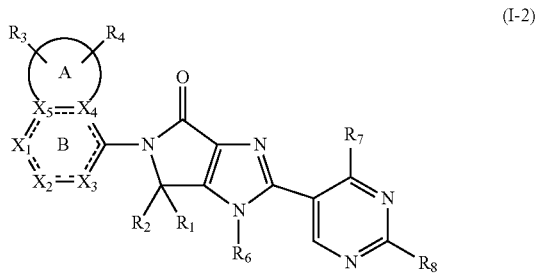

(I-2)

wherein

⌁ is selected from a double bond and a single bond;

ring A is selected from 5-membered heterocycloalkenyl, 5-membered heteroaryl and 5-membered heterocycloalkyl;

ring B is selected from 6-membered aryl and 6-membered heteroaryl;

X$_1$ is selected from C, CH, C(R$_5$) and N;
X$_2$ is selected from C, CH, C(R$_9$) and N;
X$_3$ is selected from C, CH, C(R$_{10}$) and N;
X$_4$ is selected from C, CH, C(R$_{11}$) and N;
X$_5$ is selected from C, CH, C(R$_{12}$) and N;

R$_1$ is selected from H, C$_{1-3}$ alkyl and C$_{1-3}$ heteroalkyl, wherein the C$_{1-3}$ alkyl and C$_{1-3}$ heteroalkyl are each independently and optionally substituted with 1, 2 or 3 R$_a$;

R$_2$ is selected from phenyl and 5-6 membered heteroaryl, wherein the phenyl and 5-6-membered heteroaryl are each independently and optionally substituted with 1, 2 or 3 R$_b$;

R$_3$ and R$_4$ are each independently selected from H, halogen, OH, CN, NH$_2$, C$_{1-3}$ alkyl and C$_{1-3}$ heteroalkyl, wherein the C$_{1-3}$ alkyl and C$_{1-3}$ heteroalkyl are each independently and optionally substituted with 1, 2 or 3 R$_c$;

R$_5$, R$_9$, R$_{10}$, R$_{11}$ and R$_{12}$ are each independently selected from halogen, OH, CN, NH$_2$, C$_{1-3}$ alkyl and C$_{1-3}$ heteroalkyl, wherein the C$_{1-3}$ alkyl and C$_{1-3}$ heteroalkyl are each independently and optionally substituted with 1, 2 or 3 R$_d$;

R$_6$ is selected from C$_{1-6}$ alkyl, C$_{1-6}$ heteroalkyl, C$_{3-4}$ cycloalkyl and 3-6 membered heterocycloalkyl, wherein the C$_{1-6}$ alkyl, C$_{1-6}$ heteroalkyl, C$_{3-5}$ cycloalkyl and 3-6 membered heterocycloalkyl are each independently and optionally substituted with 1, 2 or 3 R$_e$;

R$_7$ and R$_8$ are each independently selected from C$_{1-3}$ alkyl-O—, wherein the C$_{1-3}$ alkyl-O— is optionally substituted with 1, 2 or 3 halogens;

R$_a$, R$_b$, R$_c$, R$_d$ and R$_e$ are each independently selected from halogen, OH, CN, NH$_2$, C$_{1-3}$ alkyl, C$_{3-5}$ cycloalkyl and C$_{1-3}$ heteroalkyl, wherein the C$_{1-3}$ alkyl, C$_{3-5}$ cycloalkyl and C$_{1-3}$ heteroalkyl are each independently and optionally substituted with 1, 2 or 3 R;

R is selected from F, Cl, Br, I, OH, CN, NH$_2$, NO$_2$, CH$_3$, CH$_3$CH$_2$, CH$_3$CH$_2$CH$_2$, (CH$_3$)$_2$CH, CF$_3$, CHF$_2$, CH$_2$F and CH$_3$O;

each the 5-membered heterocycloalkenyl, 5-membered heteroaryl, 6-membered heteroaryl, 5-membered heterocycloalkyl, C$_{1-3}$ heteroalkyl, C$_{1-6}$ heteroalkyl, 5-6 membered heteroaryl, 3-6 membered heterocycloalkyl independently comprises 1, 2 or 3 heteroatoms or heteroatomic groups independently selected from N, —NH—, —O—, —S—, —C(=O)—, —C(=S)—, —C(=O)O—, —S(=O)— and —S(=O)$_2$—.

In some embodiments of the present disclosure, the above-mentioned R$_a$, R$_b$, R$_c$, R$_d$ and R$_e$ are each independently selected from F, C$_1$, Br, I, OH, CN, NH$_2$, CH$_3$, CH$_3$CH$_2$, CF$_3$, CHF$_2$, CH$_2$F, CH$_3$O and cyclopropyl.

In some embodiments of the present disclosure, each the above-mentioned is independently selected from H, CH$_3$, CH$_3$CH$_2$,

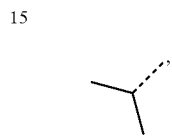

CH$_2$O(CH$_3$) and CH$_2$OH.

In some embodiments of the present disclosure, each the above-mentioned R$_2$ is independently selected from thienyl, thiazolyl and phenyl, wherein the thienyl, thiazolyl and phenyl are optionally substituted with 1, 2 or 3 R$_b$.

In some embodiments of the present disclosure, each the above-mentioned R$_2$ is independently selected from

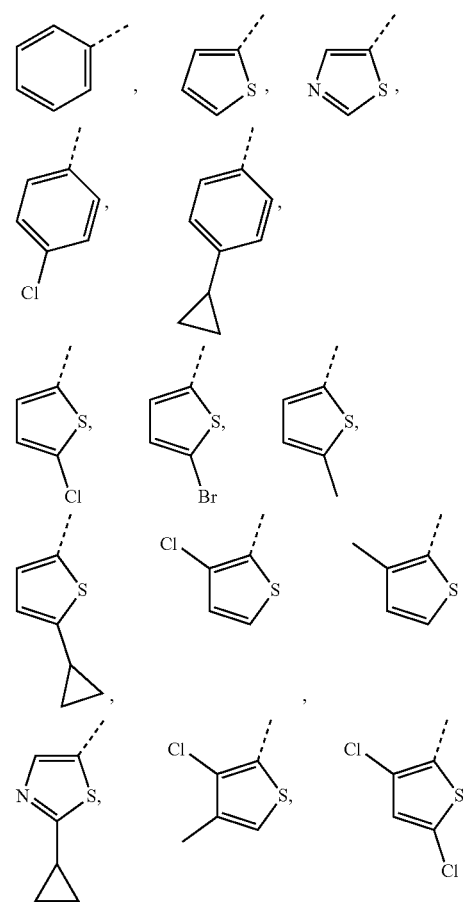

and

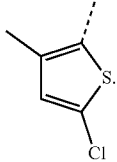

In some embodiments of the present disclosure, the above-mentioned $R_3$ and $R_4$ are each independently selected from H, F, Cl, Br, I, OH, CN, $CH_3$,

and

wherein the $CH_3$,

and

are optionally substituted with 1, 2 or 3 $R_c$.

In some embodiments of the present disclosure, the above-mentioned $R_3$ and $R_4$ are each independently selected from H, F, Cl, Br, I, OH, CN, $CH_3$,

and

In some embodiments of the present disclosure, the above-mentioned $R_5$, $R_9$, $R_{10}$, $R_{11}$ and $R_{12}$ are each independently selected from F, Cl, Br, I, OH, CN, $CH_3$,

wherein the $CH_3$,

and

are optionally substituted with 1, 2 or 3 $R_d$.

In some embodiments of the present disclosure, the above-mentioned $R_5$, $R_9$, $R_{10}$, $R_{11}$ and $R_{12}$ are each independently selected from F, Cl, Br, I, OH, CN, $CH_3$,

and

In some embodiments of the present disclosure, each the above-mentioned R, is independently selected from $C_{1-5}$ alkyl and $C_{3-6}$ cycloalkyl, wherein the $C_{1-5}$ alkyl and $C_{3-6}$ cycloalkyl are optionally substituted with 1, 2 or 3 $R_e$.

In some embodiments of the present disclosure, each the above-mentioned $R_6$ is independently selected from $CH_3$, $CH_3CH_2$,

and cyclopropyl.

In some embodiments of the present disclosure, the above-mentioned $R_7$ and $R_8$ are each independently selected from $CH_3O$, $CH_3CH_2CH_2O$, $(CH_3)_2CHO$, $CH_2FO$, $CHF_2O$, $CF_3O$ and $CH_3CH_2O$.

In some embodiments of the present disclosure, each the above-mentioned ring A is independently selected from thiazolyl, isothiazolyl, 1,3-dioxolyl, imidazolyl, pyrrolyl, 3H-pyrrolyl, isoxazolyl and oxazolyl.

In some embodiments of the present disclosure, the above-mentioned moiety

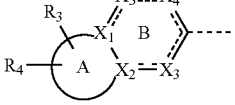

is selected from

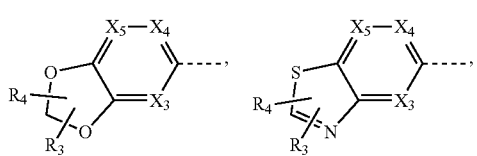 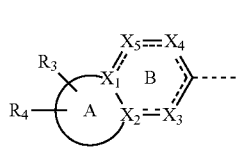

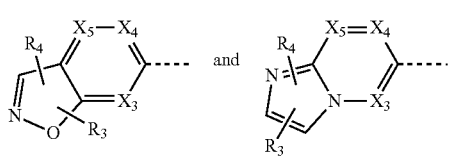

In some embodiments of the present disclosure, the above-mentioned moiety

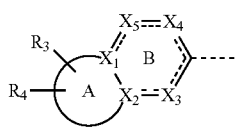

is selected from

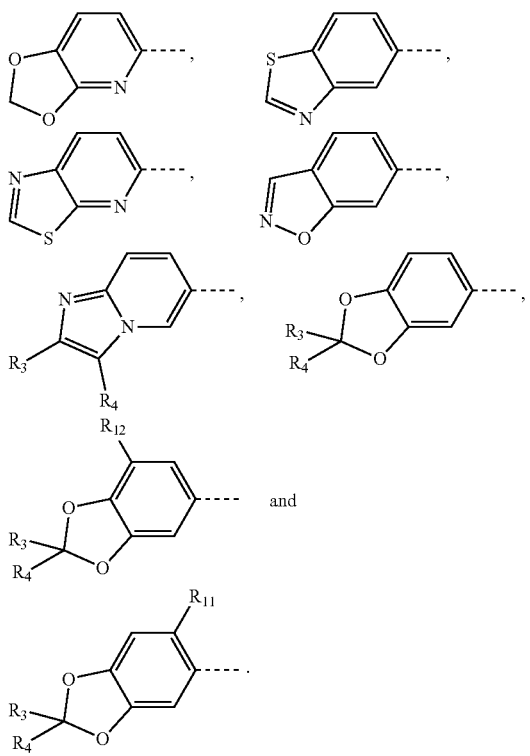

In some embodiments of the present disclosure, the above-mentioned moiety

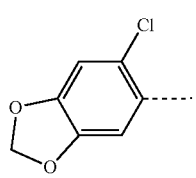

is selected from

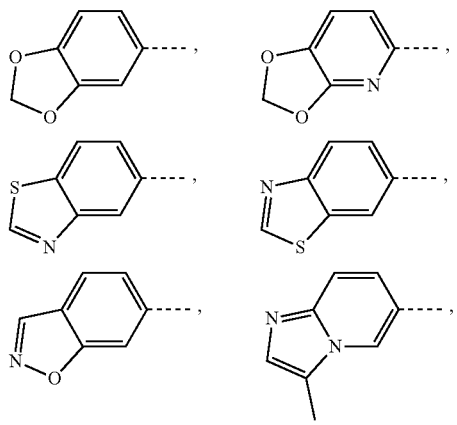

and

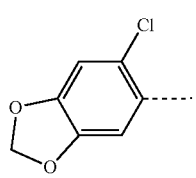

In some embodiments of the present disclosure, in the above-mentioned formula (I-1), ring A is selected from thiazolyl, isothiazolyl, 1,3-dioxolyl, imidazolyl, pyrrolyl and 3H-pyrrolyl.

In some embodiments of the present disclosure, in the above-mentioned formula (I-1), the moiety
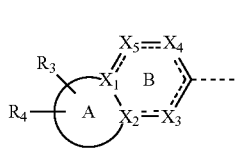
is selected from
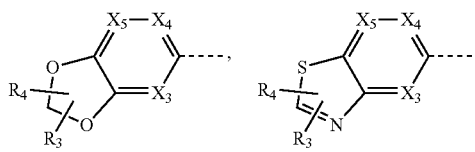
and
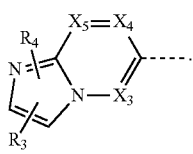
In some embodiments of the present disclosure, in the above-mentioned formula (I-1), the moiety
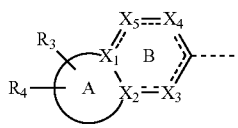
is selected from
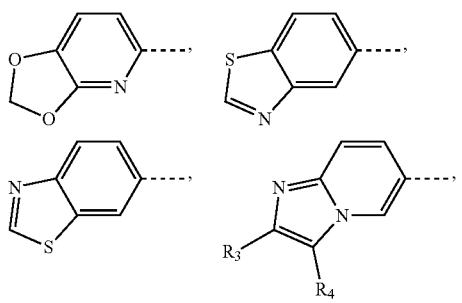
and
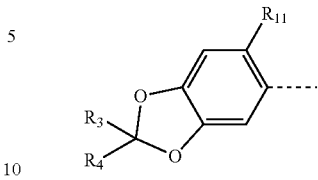
In some embodiments of the present disclosure, in the above-mentioned formula (I-1), the moiety
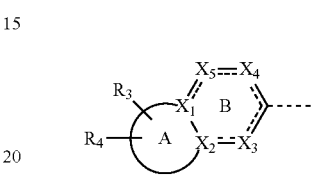
is selected from
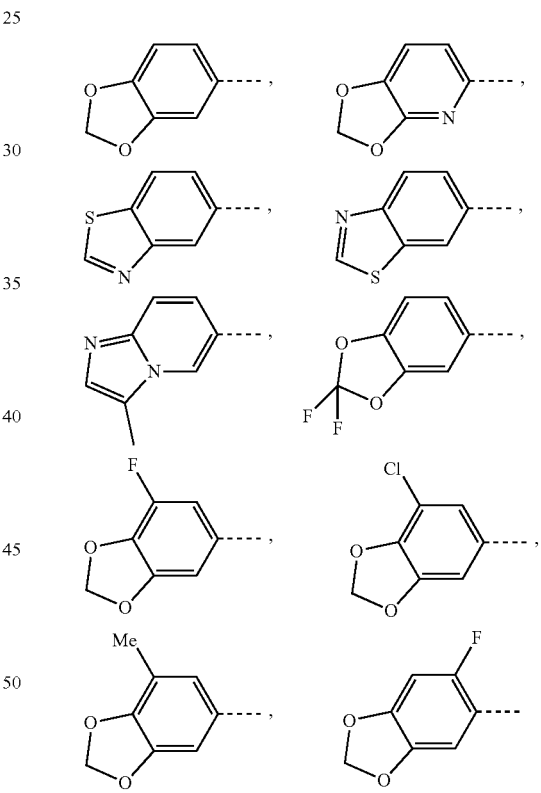
and
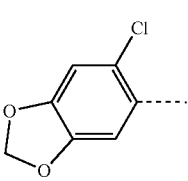

In some embodiments of the present disclosure, the above-mentioned moiety

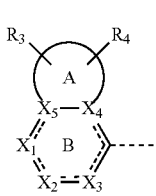

is selected from

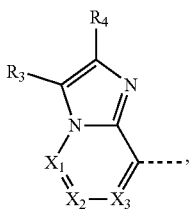 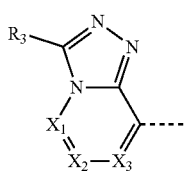

and

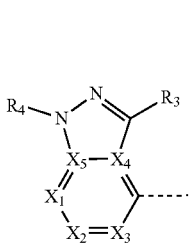

In some embodiments of the present disclosure, the above-mentioned moiety

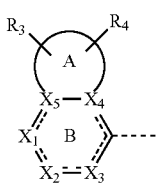

is selected from

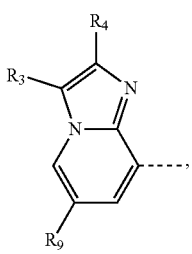 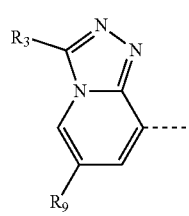

and

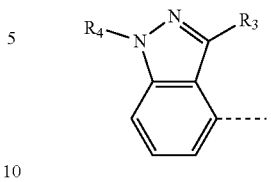

In some embodiments of the present disclosure, the above-mentioned moiety

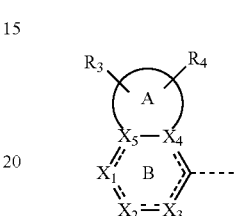

is selected from

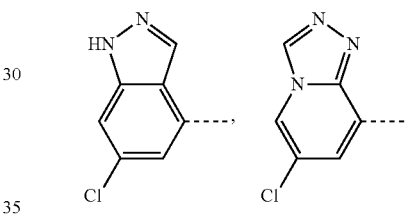

and

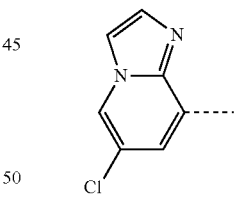

In some embodiments of the present disclosure, in the above-mentioned formula,

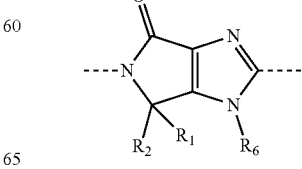

is selected from

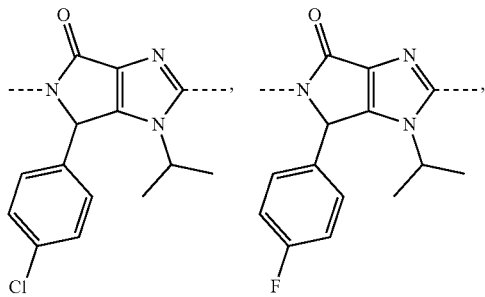

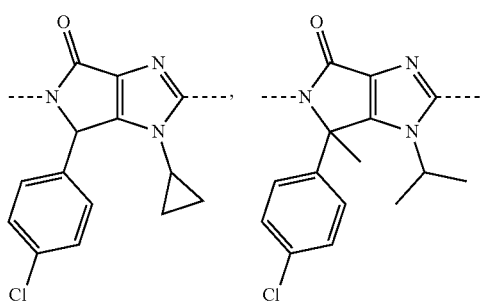

and

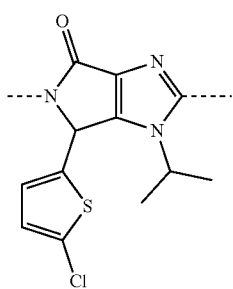

In some embodiments of the present disclosure, in the above-mentioned formula (I-2), ring A is selected from thiazolyl, isothiazolyl, 1,3-dioxolyl, imidazolyl, pyrrolyl, 3H-pyrrolyl, oxazolyl, isoxazolyl and 1,2,4-triazolyl.

In some embodiments of the present disclosure, the moiety

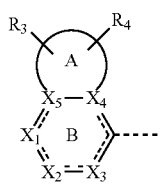

is selected from

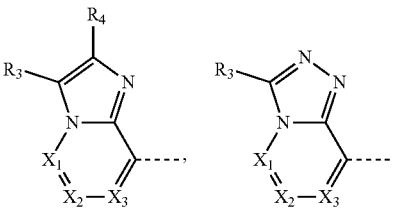

and

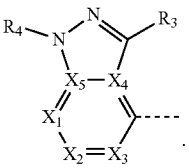

In some embodiments of the present disclosure, in the above-mentioned formula (I-2), the moiety

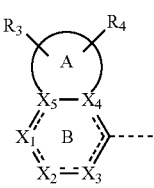

is selected from

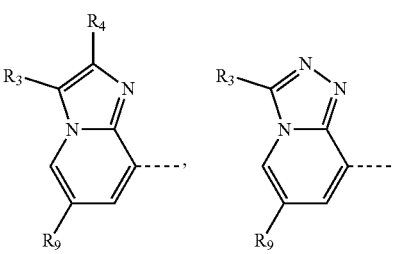

and

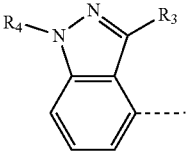

In some embodiments of the present disclosure, in the above-mentioned formula (I-2), the moiety

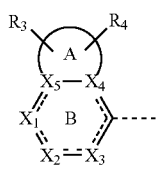

is selected from

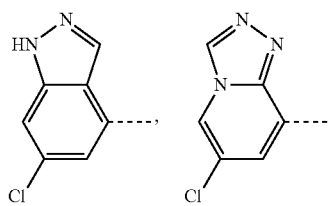

and

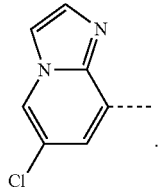

In some embodiments of the present disclosure, the above-mentioned $R_a$, $R_b$, $R_c$, $R_d$ and R are each independently selected from F, Cl, Br, I, OH, CN, $NH_2$, $CH_3$, $CH_3CH_2$, $CF_3$, $CHF_2$, $CH_2F$, $CH_3O$ and cyclopropyl, and other variables are as defined in the present disclosure.

In some embodiments of the present disclosure, each the above-mentioned is independently selected from H, $CH_3$, $CH_3CH_2$,

$CH_2O(CH_3)$ and $CH_2OH$.

In some embodiments of the present disclosure, each the above-mentioned $R_2$ is independently selected from thienyl, thiazolyl and phenyl, wherein the thienyl, thiazolyl and phenyl are optionally substituted with 1, 2 or 3 $R_b$, and other variables are as defined in the present disclosure.

In some embodiments of the present disclosure, each the above-mentioned $R_2$ is independently selected from

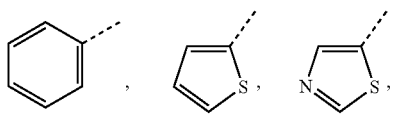

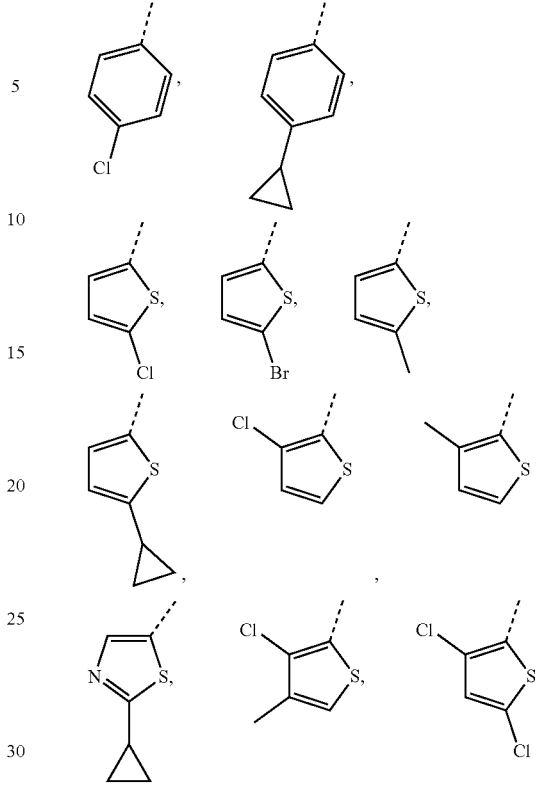

and

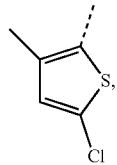

and other variables are as defined in the present disclosure.

In some embodiments of the present disclosure, the above-mentioned $R_3$ and $R_4$ are each independently selected from H, F, Cl, Br, I, OH, CN, $CH_3$,

and

wherein the $CH_3$,

and

are optionally substituted with 1, 2 or 3 $R_c$, and other variables are as defined in the present disclosure.

In some embodiments of the present disclosure, the above-mentioned $R_3$ and $R_4$ are each independently selected from H, F, Cl, Br, I, OH, CN, CH$_3$,

and

and other variables are as defined in the present disclosure.

In some embodiments of the present disclosure, the above-mentioned $R_5$, $R_9$, $R_{10}$, $R_{11}$ and $R_{12}$ are each independently selected from F, Cl, Br, I, OH, CN, CH$_3$,

and

wherein the CH$_3$,

and

are optionally substituted with 1, 2 or 3 $R_d$, and other variables are as defined in the present disclosure.

In some embodiments of the present disclosure, the above-mentioned $R_5$, $R_9$, $R_{10}$, $R_{11}$ and $R_{12}$ are each independently selected from F, Cl, Br, I, OH, CN, CH$_3$,

and

and other variables are as defined in the present disclosure.

In some embodiments of the present disclosure, each the above-mentioned $R_6$ is independently selected from $C_{1-5}$ alkyl and $C_{3-6}$ cycloalkyl, wherein the $C_{1-5}$ alkyl and $C_{3-6}$ cycloalkyl are optionally substituted with 1, 2 or 3 $R_e$, and other variables are as defined in the present disclosure.

In some embodiments of the present disclosure, each the above-mentioned $R_6$ is independently selected from CH$_3$, CH$_3$CH$_2$,

and cyclopropyl, and other variables are as defined in the present disclosure.

In some embodiments of the present disclosure, the above-mentioned $R_7$ and $R_8$ are each independently selected from CH$_3$O, CH$_3$CH$_2$CH$_2$O, (CH$_3$)$_2$CHO, CH$_2$FO, CHF$_2$O, CF$_3$O and CH$_3$CH$_2$O, and other variables are as defined in the present disclosure.

In some embodiments of the present disclosure, each the above-mentioned ring A is independently selected from thiazolyl, isothiazolyl, 1,3-dioxolyl, imidazolyl, pyrrolyl, 3H-pyrrolyl, isoxazolyl and oxazolyl, and other variables are as defined in the present disclosure.

In some embodiments of the present disclosure, the above-mentioned moiety

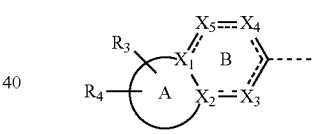

is selected from

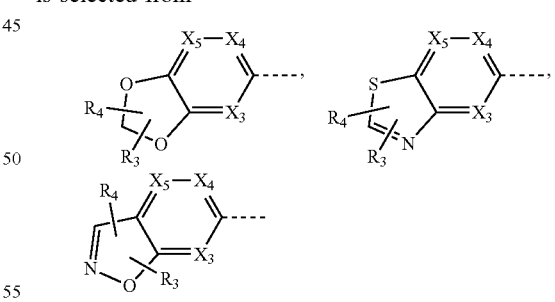

and

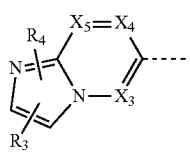

and other variables are as defined in the present disclosure.

In some embodiments of the present disclosure, the above-mentioned moiety

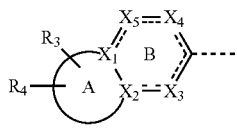

is selected from

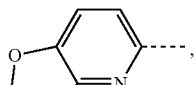 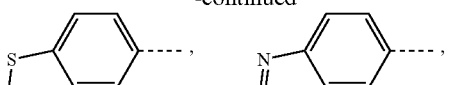

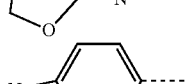 

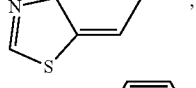 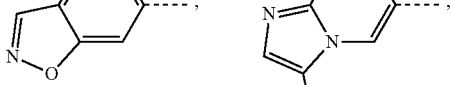

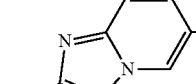 

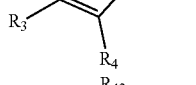 

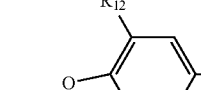 

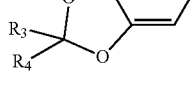 

 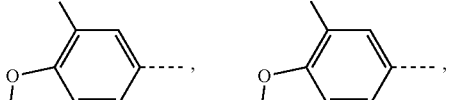

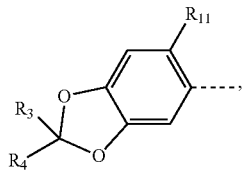

and

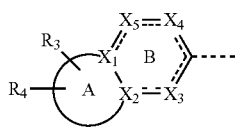

and other variables are as defined in the present disclosure.

In some embodiments of the present disclosure, the above-mentioned moiety

is selected from

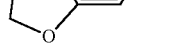

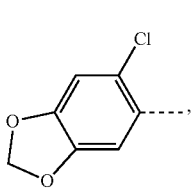

and

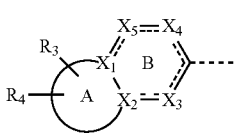

and other variables are as defined in the present disclosure.

In some embodiments of the present disclosure, in the above-mentioned formula (I-1), ring A is selected from thiazolyl, isothiazolyl, 1,3-dioxolyl, imidazolyl, pyrrolyl and 3H-pyrrolyl, and other variables are as defined in the present disclosure.

In some embodiments of the present disclosure, in the above-mentioned formula (I-1), the moiety is selected from

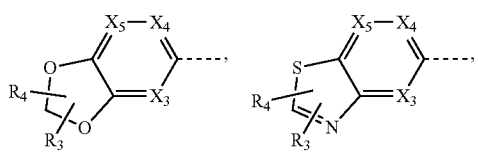

and

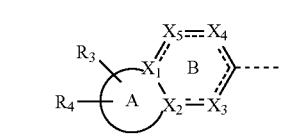

and other variables are as defined in the present disclosure.

In some embodiments of the present disclosure, in the above-mentioned formula (I-1), the moiety

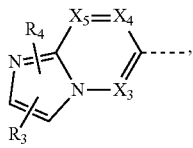

is selected from

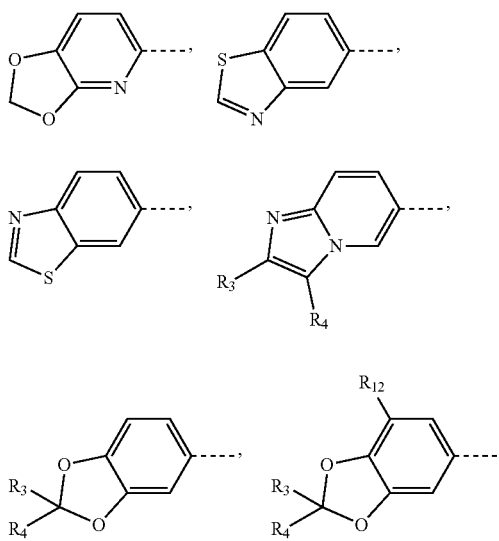

and

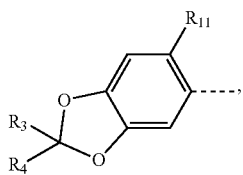

and other variables are as defined in the present disclosure.

In some embodiments of the present disclosure, in the above-mentioned formula (I-1), the moiety

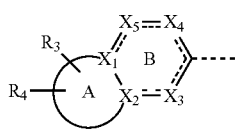

is selected from

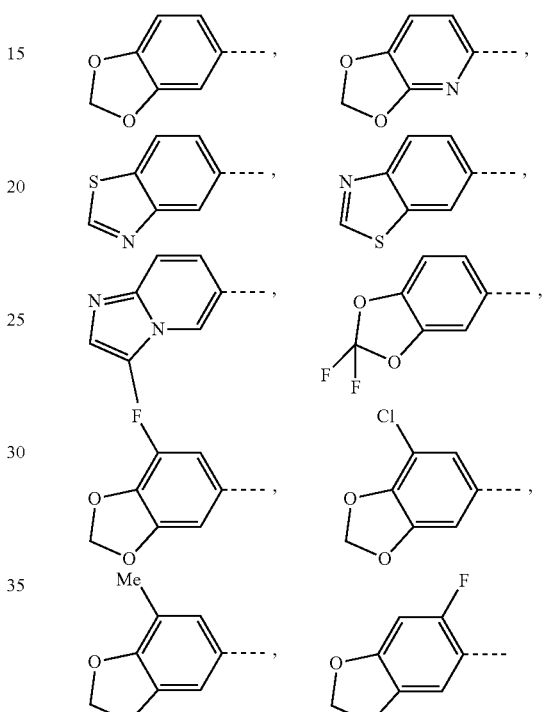

and

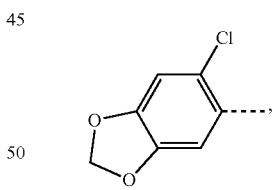

and other variables are as defined in the present disclosure.

In some embodiments of the present disclosure, the above-mentioned moiety

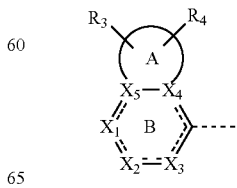

is selected from

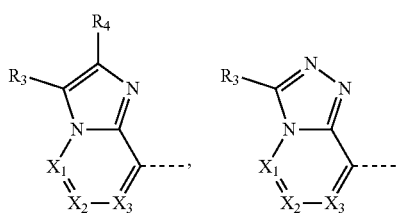

and

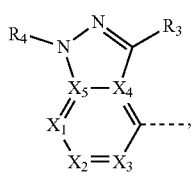

and other variables are as defined in the present disclosure.

In some embodiments of the present disclosure, the above-mentioned moiety

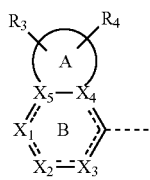

is selected from

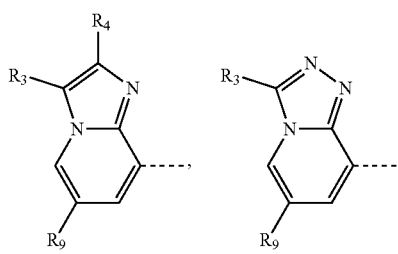

and

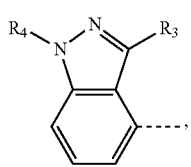

and other variables are as defined in the present disclosure.

In some embodiments of the present disclosure, the above-mentioned moiety

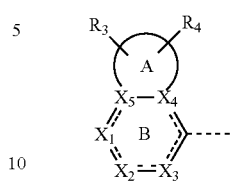

is selected from

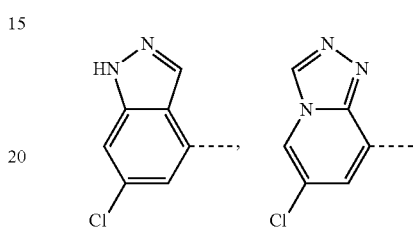

and

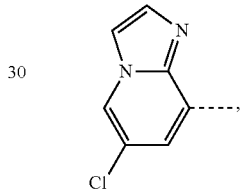

and other variables are as defined in the present disclosure.

In some embodiments of the present disclosure, in the above-mentioned formula (I-2), ring A is selected from thiazolyl, isothiazolyl, 1,3-dioxolyl, imidazolyl, pyrrolyl, 3H-pyrrolyl, oxazolyl, isoxazolyl and 1,2,4-triazolyl, and other variables are as defined in the present disclosure.

In some embodiments of the present disclosure, in the above-mentioned formula (I-2), the moiety

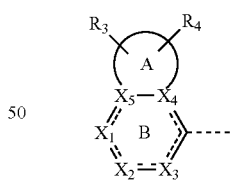

is selected from

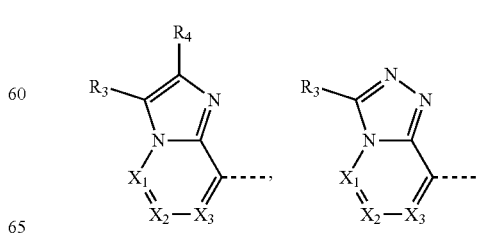

and

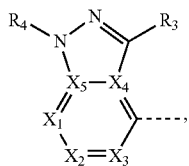

and other variables are as defined in the present disclosure.

In some embodiments of the present disclosure, in the above-mentioned formula (I-2), the moiety

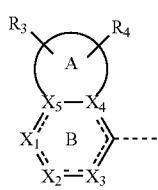

is selected from

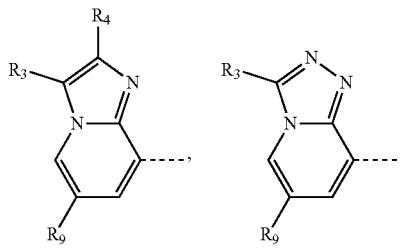

and

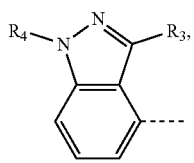

and other variables are as defined in the present disclosure.

In some embodiments of the present disclosure, in the above-mentioned formula (I-2), the moiety

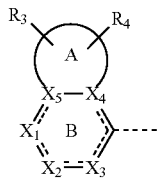

is selected from

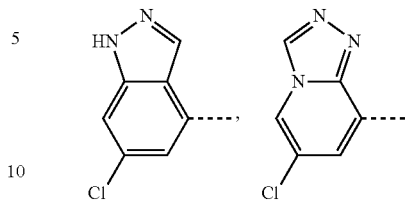

and

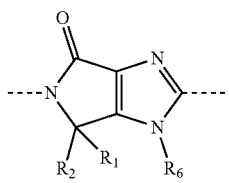

and other variables are as defined in the present disclosure.

In some embodiments of the present disclosure, in the above-mentioned formula,

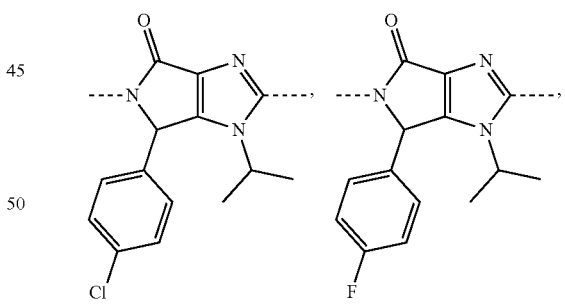

is selected from

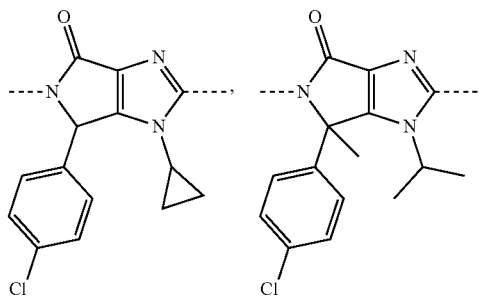

and

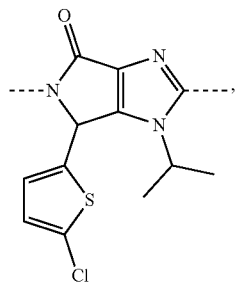

and other variables are as defined in the present disclosure.

In some embodiments of the present disclosure, for the above-mentioned compound or a pharmaceutically acceptable salt thereof, the compound is selected from (I-3)

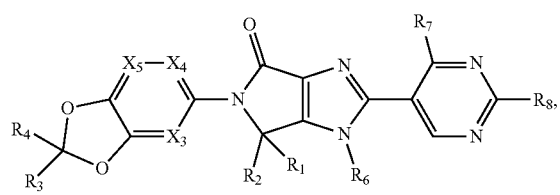

wherein $X_3$, $X_4$, $X_5$, $R_1$, $R_2$, $R_3$, $R_4$, $R_5$, $R_6$, $R_7$ and $R_8$ are as defined in the present disclosure. The present disclosure also provides a compound or a pharmaceutically acceptable salt thereof, which is selected from

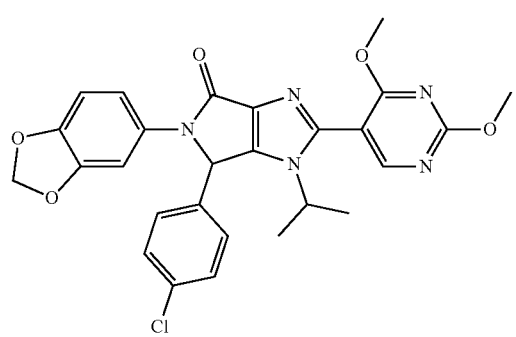

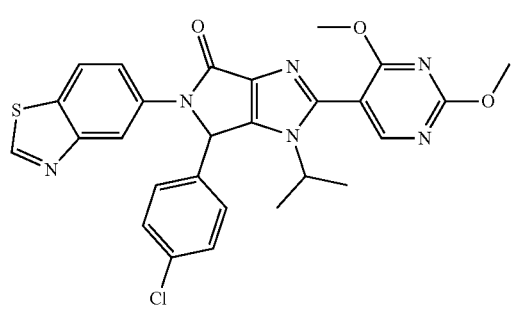

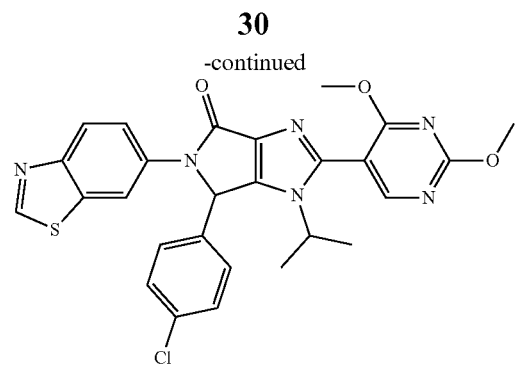

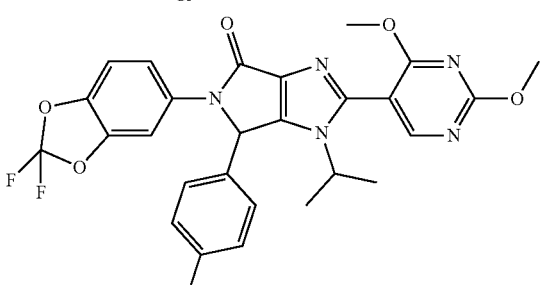

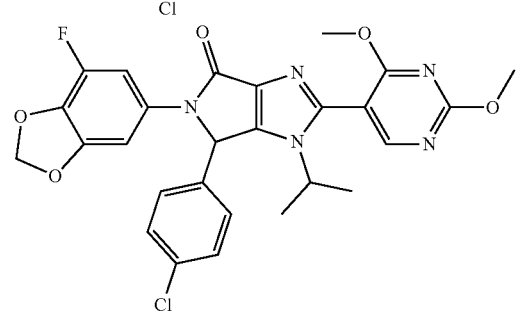

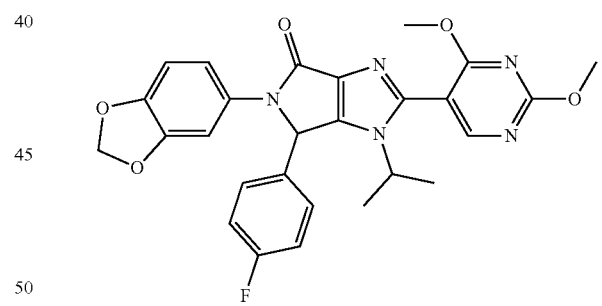

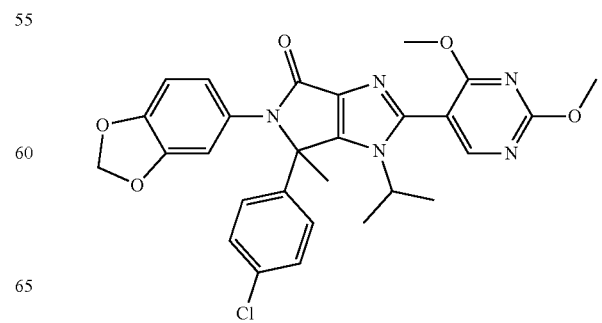

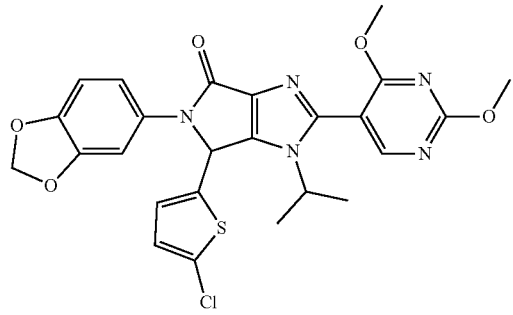
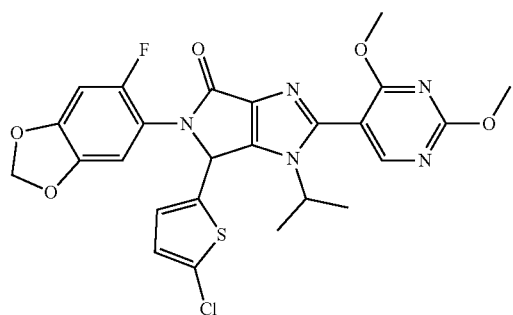
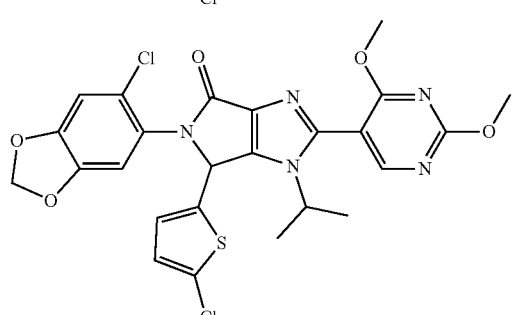
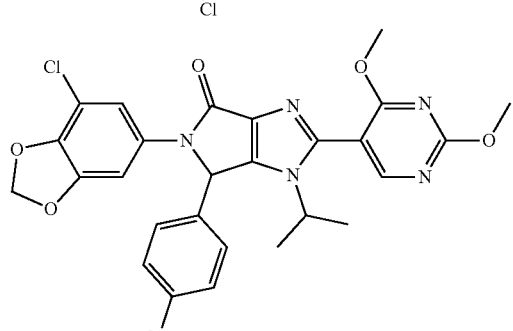
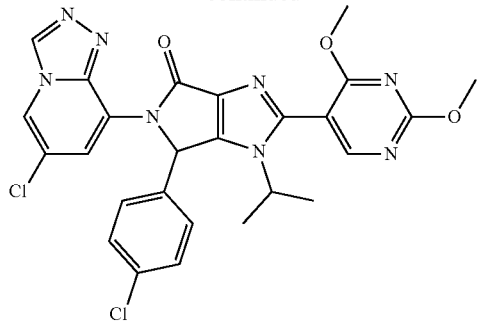
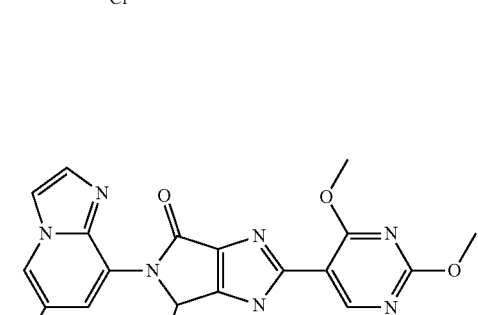
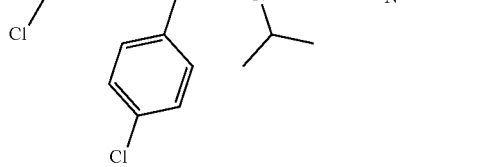
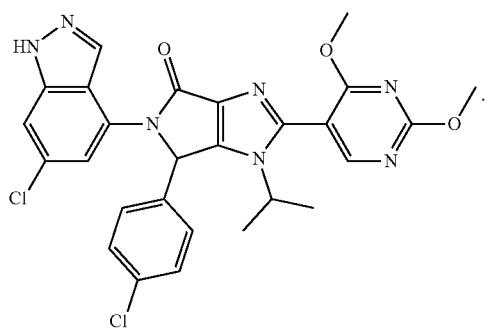
In some embodiments of the present disclosure, the above-mentioned compound or a pharmaceutically acceptable salt thereof is selected from
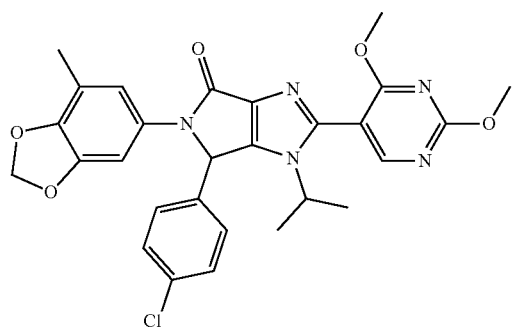
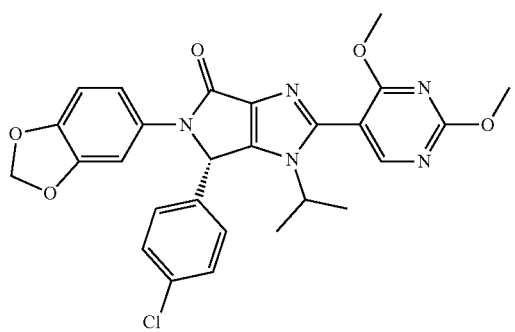

33
-continued
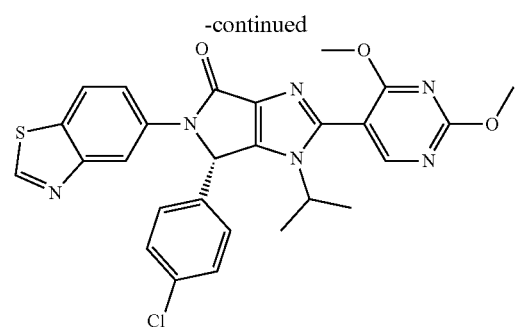
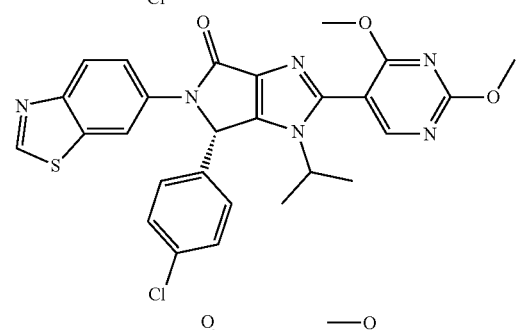
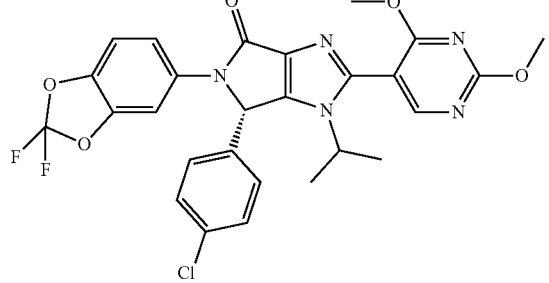
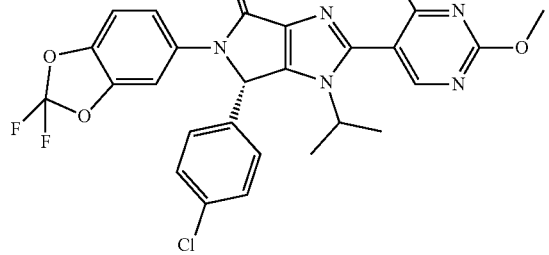
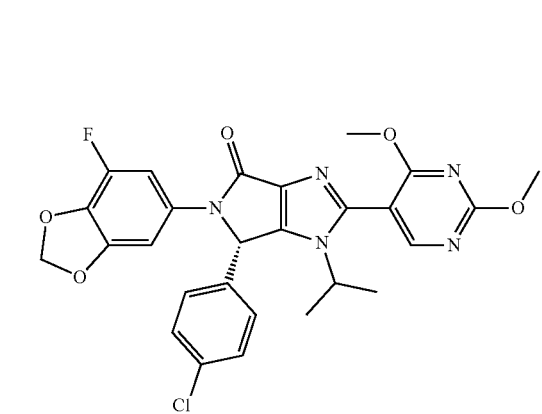
34
-continued
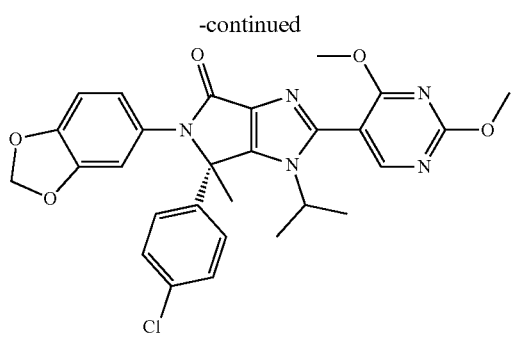
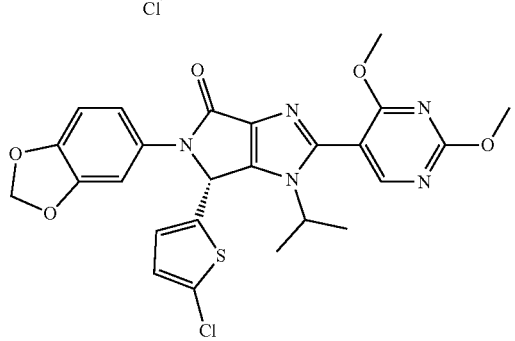
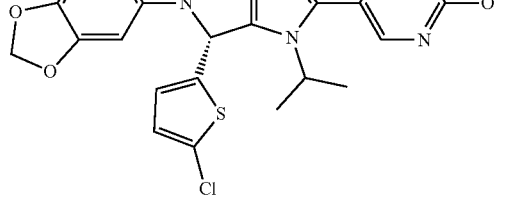
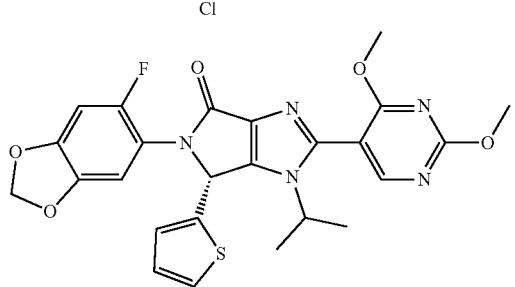
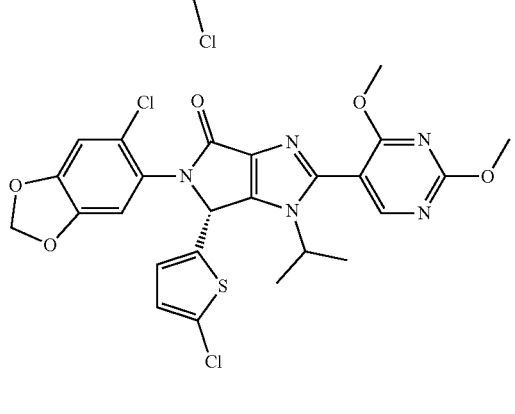

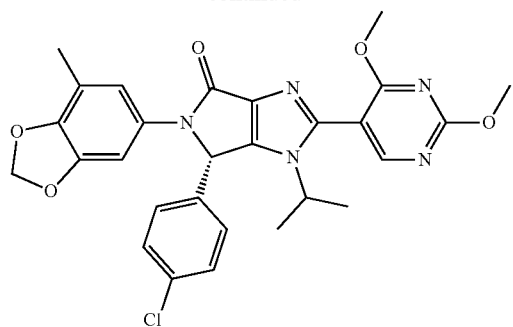
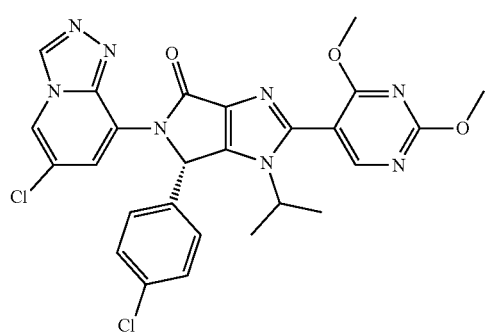
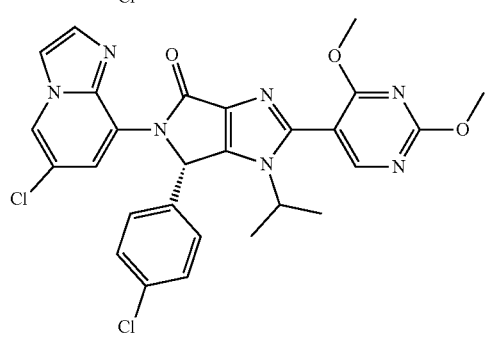
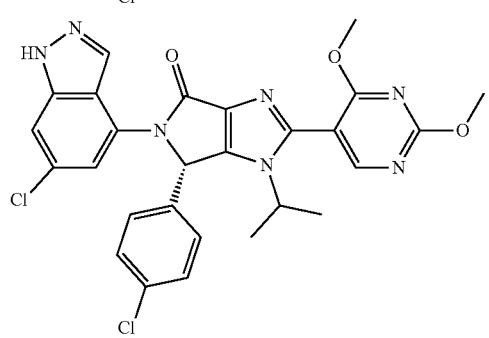
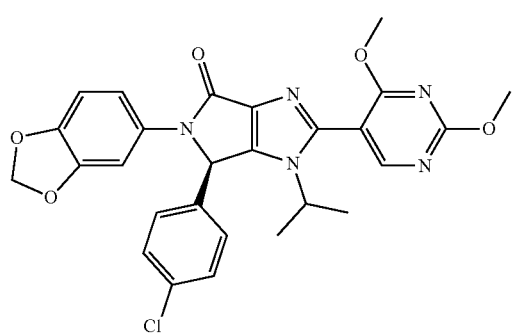
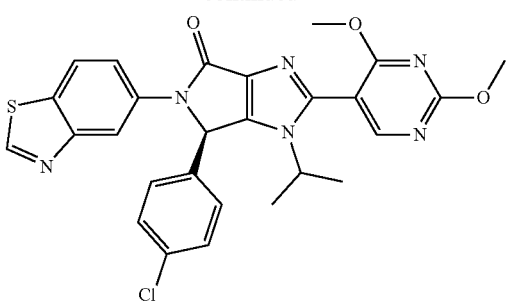
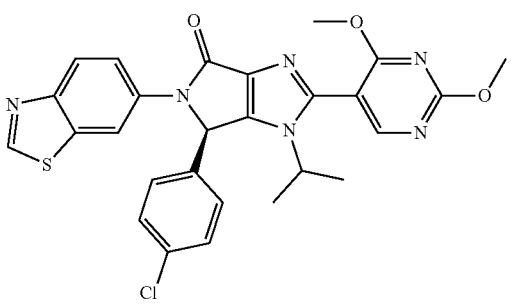
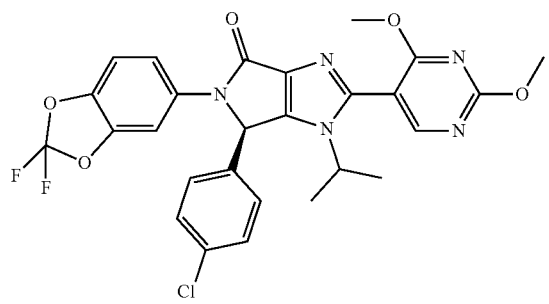
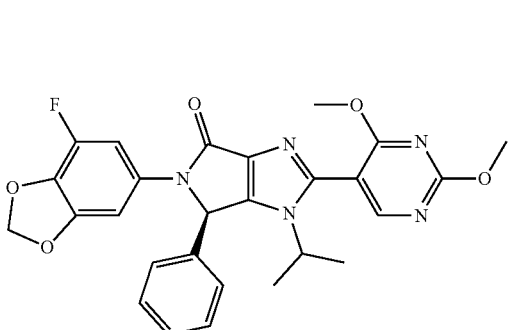
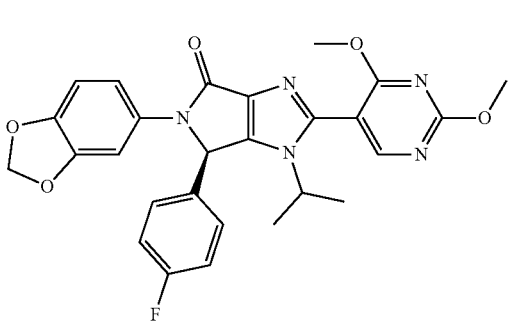

-continued

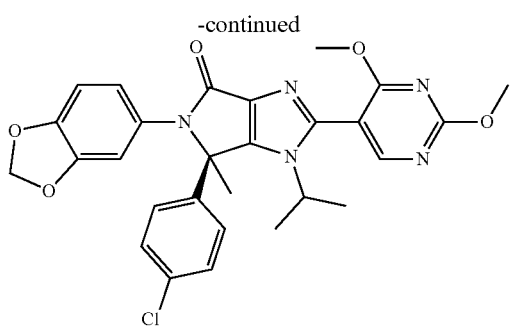
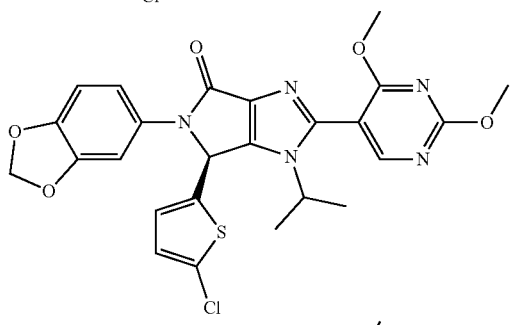
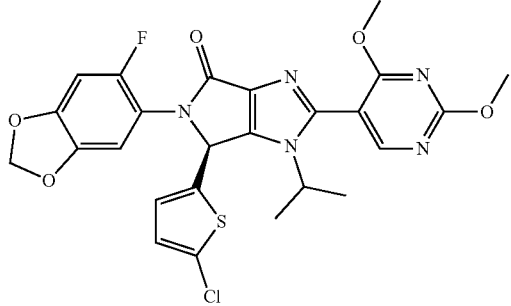
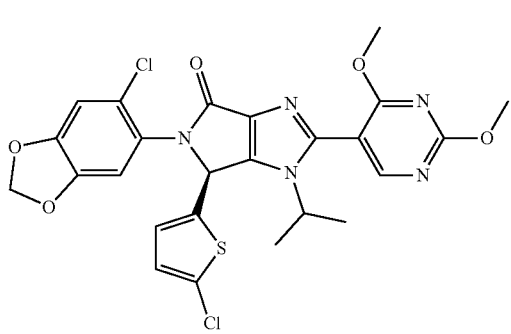
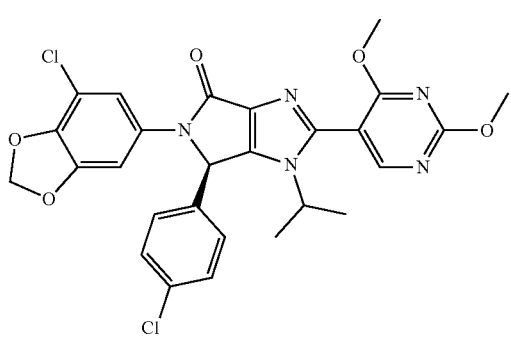

-continued

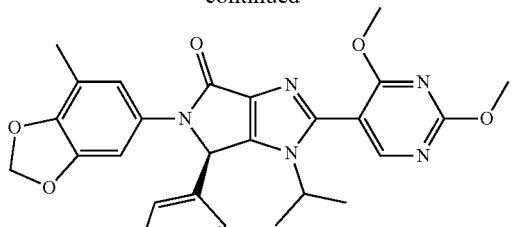
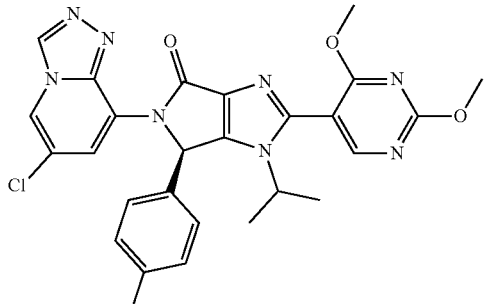
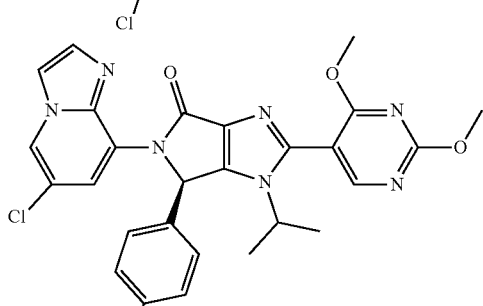
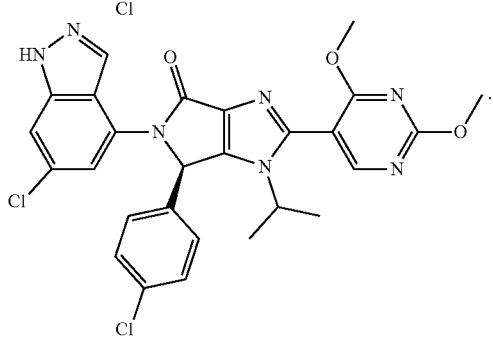

The present disclosure further provides uses of the above-mentioned compound or a pharmaceutically acceptable salt thereof in the manufacture of a medicine for treating cancers, bacterial infections, and viral infections.

There are still some embodiments of the present disclosure derived from any combination of the above variables.

DETAILED DESCRIPTION OF THE INVENTION

Technical Effects

The drug molecule with an imidaxopyrolone structure involved in the present disclosure is obviously different from the MDM2-p53 inhibitor reported in earlier patents, and this type of drug molecule can inhibit the interaction between p53 and MDM2 and activate the downstream effector group of the p53. In in vitro experiments, the drug molecule with an imidaxopyrolone structure shows a good activity in binding to the MDM2 protein target and inhibiting the growth of SJSA-1 tumor cells. In addition, in in-vivo experiments in mice, the drug molecule shows better PK properties and better anti-tumor efficacy than the reference molecule. Based on this, the drug molecule with an imidaxopyrolone structure involved in the present disclosure can be used to treat solid tumors such as breast tumors, colon tumors, lung tumors, esophageal tumors and prostate tumors, as well as liquid tumors such as lymphomas and leukemias, bacterial infections, viral infections, ulcers and inflammations or the like.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof. The term "pharmaceutically acceptable" as used herein refers to those compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present disclosure, which is prepared from the compound having specific substituents found in the present disclosure with relatively non-toxic acids or bases. When compounds of the present disclosure contain relatively acidic functional groups, base addition salts can be obtained by contacting the neutral form of such compounds with a sufficient amount of base, either in pure solution or a suitable inert solvent. Pharmaceutically acceptable base addition salts include sodium, potassium, calcium, ammonium, organic amine or magnesium salts or similar salts. When compounds of the present disclosure contain relatively basic functional groups, acid addition salts can be obtained by contacting the neutral form of such compounds with a sufficient amount of acid, either in pure solution or a suitable inert solvent. Examples of pharmaceutically acceptable acid addition salts include salts of inorganic acids, which include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid; and salts of organic acids, which include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and also include salts of amino acids (such as arginine), and salts of organic acids such as glucuronic acid. Certain specific compounds of the present disclosure contain basic and acidic functional groups and thus can be converted to any base or acid addition salt.

The pharmaceutically acceptable salts of the present disclosure can be synthesized from a parent compound containing acid radicals or base radicals by conventional chemical methods. In general, the method for preparing such salts comprises: in water or an organic solvent or a mixture of both, reacting these compounds in free acid or base forms with a stoichiometric amount of a suitable base or acid to prepare the salts.

In addition to salt forms, the compounds provided by the disclosure also exist in prodrug forms. The prodrugs of the compounds described herein are prone to chemical changes under physiological conditions, and thus are converted into the compounds of the present disclosure. In addition, prodrugs can be converted to the compounds of the disclosure by chemical or biochemical methods in the in vivo environment.

Certain compounds of the present disclosure may exist in unsolvated or solvated forms, including hydrated forms. Generally speaking, the solvated form is equivalent to the unsolvated form, and both are included in the scope of the present disclosure.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present disclosure. Additional asymmetric carbon atoms may be present in a substituent such as an alkyl group. All these isomers and mixtures thereof are included in the scope of the present disclosure.

Unless otherwise stated, the term "enantiomer" or "optical isomers" refers to stereoisomers that are mirror images of each other.

Unless otherwise stated, the term "cis-trans isomer" or "geometric isomer" is caused by the fact that double bonds or single bonds of ring-forming carbon atoms cannot rotate freely.

Unless otherwise stated, the term "diastereomers" refers to stereoisomers in which molecules have two or more chiral centers and are not mirror images of each other.

Unless otherwise stated, "(D)" or "(+)" means dextrorotatory, "(L)" or "(−)" means levorotatory, and "(DL)" or "(±)" means racemic.

Unless otherwise stated, the wedge-shaped solid bond ( ▰ ) and the wedge-shaped dotted bond ( ▰ ) represent the absolute configuration of a stereoscopic center; the straight solid bond ( ▰ ) and straight dotted bond ( ▰ ) represent the relative configuration of a stereoscopic center; the wavy line ( ▰ ) represents the wedge-shaped solid bond ( ▰ ) or the wedge-shaped dotted bond ( ▰ ); or the wavy line ( ▰ ) represents the straight solid bond ( ▰ ) and the straight dotted bond ( ▰ ).

The compounds of the present disclosure may exist in specific. Unless otherwise stated, the term "tautomer" or "tautomeric form" means that at room temperature, isomers with different functional groups are in dynamic equilibrium and can be quickly converted to each other. Where tautomerization is possible (such as in solution), a chemical equilibrium of tautomers can be achieved. For example, proton tautomers (also known as prototropic tautomers) include interconversion via migration of a proton, such as keto-enol isomerization and imine-enamine isomerization. Valence tautomers include some interconversions by recombination of some of bond-forming electrons. A specific example of keto-enol tautomerization is the interconversion between two tautomers, pentane-2,4-dione and 4-hydroxypent-3-en-2-one.

Unless otherwise stated, the terms "rich in one isomer", "isomer enriched", "rich in one enantiomer" or "enantiomerically enriched" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomers and D and L isomers can be prepared using chiral synthesis or chiral reagents or other conventional techniques. If a particular enantiomer of a compound of the present disclosure is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished using chromatography, which uses chiral stationary phases, optionally in combination with chemical derivatization methods (e.g., formation of carbamates from amines). The compounds of the present disclosure may contain unnatural proportions of atomic isotopes at one or more of the atoms constituting the compound. For example, the compounds may be radiolabeled with radioactive isotopes, such as tritium ($^3$H), iodine-125 ($^{125}$I) or C-14 ($^{14}$C). For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present disclosure, whether radioactive or not, are intended to be encompassed within the scope of the present disclosure. "Optional" or "optionally" means that the subsequently described event or circumstance may, but not necessarily occur, and that the description includes instances where said event or circumstance occurs and instances where said event or circumstance does not occur.

The term "substituted" means that any one or more hydrogen atoms on the designated atom is substituted by a substituent, which may include heavy hydrogen and hydrogen variants, provided that the valence state of the designated atom is normal, and the substituted compound is stable. Where the substituent is oxygen (i.e., =O), it means that two hydrogen atoms are substituted. Oxygen substitution does not occur on aromatic groups. The term "optionally substituted" means that it may or may not be substituted.

Unless otherwise specified, the type and number of substituents may be arbitrary on the basis that they can be achieved in chemistry.

Where any variable (such as R) appears more than once in the composition or structure of a compound, its definition in each case is independent. Thus, for example, if a group is substituted with 0-2 R, the group can optionally be substituted with up to two R, and R in each case has independent options. In addition, combinations of substituents and/or variants thereof are permissible only if such combinations result in stable compounds.

When the number of a linking group is 0, such as —(CRR)$_0$—, it means that the linking group is a single bond.

When one of the variables is selected from a single bond, it means that the two groups to which it is connected are directly connected. For example, when L represents a single bond in A-L-Z, it means that the structure is actually A-Z.

When a substituent is vacant, it means that the substituent does not exist. For example, when X is vacant in A-X, it means that the structure is actually A. When the bond of a substituent can be cross-connected to more than two atoms on a ring, the substituent can be bonded to any atom on the ring, for example, the moiety

or

indicates that the substituent R can be substituted at any position on the cyclohexyl or cyclohexadiene. When the substituents listed do not indicate through which atom they are connected to the substituted group, such substituents can be bonded through any of the atoms thereof, for example, pyridyl as a substituent can be attached to the substituted group via any carbon atom on the pyridine ring.

When the linking group listed does not indicate the linking direction thereof, the linking direction is arbitrary, for example, the linking group L is -M-W— in

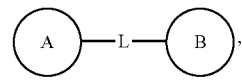

at this situation, -M-W— can connect ring A and ring B in the same direction as the reading order from left to right to form

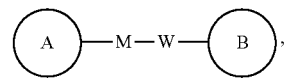

and can also connect ring A and ring B in the opposite direction as the reading order from left to right to form

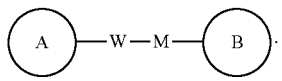

Combinations of the linking groups, substituents, and/or variants thereof are permissible only if such combinations result in stable compounds.

Unless otherwise specified, the term "hetero" means a heteroatom or a heteroatomic group (i.e., an atomic groups containing a heteroatom), including atoms other than carbon (C) and hydrogen (H) as well as atomic groups containing such heteroatoms, for example, oxygen (O), nitrogen (N), sulfur (S), silicon (Si), germanium (Ge), aluminum (Al), boron (B), —O—, —S—, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, "ring" means substituted or unsubstituted cycloalkyl, heterocycloalkyl, cycloalkenyl, heterocycloalkenyl, cycloalkynyl, heterocycloalkynyl, aryl, or heteroaryl. The ring includes a monocyclic ring, and also includes a spiro ring, a fused ring, a bridge ring and other bicyclic or polycyclic ring systems. The number of atoms in a ring is usually defined as the member number of the ring. For example, "5- to 7-membered ring" means that there are 5 to 7 atoms arranging in a circle. Unless otherwise specified, the ring optionally contains 1 to 3 heteroatoms. Therefore, "5- to 7-membered ring" includes, for example, phenyl, pyridyl, and piperidinyl; on the other hand, the term "5- to 7-membered heterocycloalkyl" includes pyridyl and piperidyl, but excludes phenyl. The term "ring" also includes ring systems containing at least one ring, each ring of which independently conforms to the above definition.

Unless otherwise specified, the term "alkyl" is used to represent a linear or branched saturated hydrocarbon group. In some embodiments, the alkyl is $C_{1-12}$ alkyl. In other embodiments, the alkyl is $C_{1-6}$ alkyl. In other embodiments, the alkyl is $C_{1-3}$ alkyl. It may be mono-substituted (such as —CH$_2$F) or poly-substituted (such as —CF$_3$), and may be monovalent, divalent (such as methylene) or polyvalent (such as methine). Examples of alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl) and hexyl.

Unless otherwise specified, "alkenyl" is used to represent a linear or branched hydrocarbon group containing one or more carbon-carbon double bonds, which may be located at any position of the group. In some embodiments, the alkenyl is $C_{2-8}$ alkenyl. In other embodiments, the alkenyl is $C_{2-6}$ alkenyl. In other embodiments, the alkenyl is $C_{2-4}$ alkenyl. It may be mono-substituted or poly-substituted, and may be monovalent, divalent or polyvalent. Examples of alkenyl include, but are not limited to, vinyl, propenyl, butenyl, pentenyl, hexenyl, butadienyl, piperylene and hexadienyl.

Unless otherwise specified, "alkynyl" is used to represent a linear or branched hydrocarbon group containing one or more carbon-carbon triple bonds which may be located at any position of the group. In some embodiments, the alkynyl is $C_{2-8}$ alkynyl. In other embodiments, the alkynyl is $C_{2-6}$ alkynyl. In other embodiments, the alkenyl is $C_{2-4}$ alkenyl. It may be mono-substituted or poly-substituted, and may be monovalent, divalent or polyvalent. Examples of alkynyl include, but are not limited to, ethynyl, propynyl, butynyl and pentynyl.

Unless otherwise specified, the term "heteroalkyl" by itself or in combination with another term means a stable linear or branched alkyl atomic group consisting of a certain number of carbon atoms and at least one heteroatom or heteroatomic group, or a combination thereof. In some embodiments, the heteroatom is selected from B, O, N and S, wherein the nitrogen and sulfur atoms are optionally oxidized, and the nitrogen heteroatom is optionally quaternized. In other embodiments, the heteroatomic group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkyl is $C_{1-6}$ heteroalkyl. In other embodiments, the heteroalkyl is $C_{1-3}$ heteroalkyl. Heteroatom or heteroatomic group may be located at any internal position of heteroalkyl, including the connection positions of the alkyl to the remainder of the molecule. However, the terms "alkoxy", "alkylamino" and "alkylthio" (or thioalkoxy) are used in their conventional sense and refer to those alkyl groups attached to the remainder of the molecule via an oxygen atom, an amino group, or a sulfur atom, respectively. Examples of heteroalkyl include but are not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$, —S(=O)—CH$_3$, —CH$_2$—CH$_2$—S(=O)$_2$—CH$_3$, —CH=CHO—CH$_3$, —CH$_2$—CH=N—OCH$_3$ and —CH=CH—N(CH$_3$)—CH$_3$. Up to two heteroatoms can be consecutive, such as —CH$_2$—NH—OCH$_3$.

Unless otherwise specified, the term "heteroalkenyl" by itself or in combination with another term means a stable linear or branched alkenyl atomic group consisting of a certain number of carbon atoms and at least one heteroatom or heteroatomic group, or a combination thereof. In some embodiments, the heteroatom is selected from B, O, N and S, wherein the nitrogen and sulfur atoms are optionally oxidized, and the nitrogen heteroatom is optionally quaternized. In other embodiments, the heteroatomic group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkenyl is $C_{2-6}$ heteroalkenyl. In other embodiments, the heteroalkyl is $C_{2-4}$ heteroalkenyl. Heteroatom or heteroatomic group may be located at any internal position of heteroalkenyl, including the connection positions of the alkenyl to the remainder of the molecule. However, the terms "alkenyloxy", "alkenylamino" and "alkenylthio" are used in their conventional sense and refer to those alkenyl groups attached to the remainder of the molecule via an oxygen atom, an amino group, or a sulfur atom, respectively. Examples of heteroalkenyl include but are not limited to, —O—CH=CH$_2$, —O—CH=CHCH$_3$, —O—CH=C(CH$_3$)$_2$, —CH=CHO—CH$_3$, —O—CH=CHCH$_2$CH$_3$, —CH$_2$—CH=CH—OCH$_3$, —NH—CH=CH$_2$, —N(CH=CH$_2$)—CH$_3$, —CH=CH—NH—CH$_3$, —CH=CH—N(CH$_3$)$_2$, —S—CH=CH$_2$, —S—CH=CHCH$_3$, —S—CH=C(CH$_3$)$_2$, —CH$_2$—S—CH=CH$_2$, —S(=O)—CH=CH$_2$ and —CH=CH—S(=O)$_2$—CH$_3$. Up to two heteroatoms may be consecutive, for example, —CH=CH—NH—OCH$_3$.

Unless otherwise specified, the term "heteroalkynyl" by itself or in combination with another term means a stable linear or branched alkynyl atomic group consisting of a certain number of carbon atoms and at least one heteroatom or heteroatomic group, or a combination thereof. In some embodiments, the heteroatom is selected from B, O, N and S, wherein the nitrogen and sulfur atoms are optionally oxidized, and the nitrogen heteroatom is optionally quaternized. In other embodiments, the heteroatomic group is selected from —C(=O)O—, —C(=O)—, —C(=S)—, —S(=O)—, —S(=O)$_2$—, —C(=O)N(H)—, —N(H)—, —C(=NH)—, —S(=O)$_2$N(H)— and —S(=O)N(H)—. In some embodiments, the heteroalkynyl is $C_{2-6}$ heteroalkynyl. In other embodiments, the heteroalkyl is $C_{2-4}$ heteroalkynyl. Heteroatom or heteroatomic group may be located at any internal position of heteroalkynyl, including the connection positions of the alkynyl to the remainder of the molecule. However, the terms "alkynyloxy", "alkynylamino" and "alkynylthio" are used in their conventional sense and refer to those alkynyl groups attached to the remainder of the molecule via an oxygen atom, an amino group, or a sulfur atom, respectively. Examples of heteroalkynyl include but are not limited to,

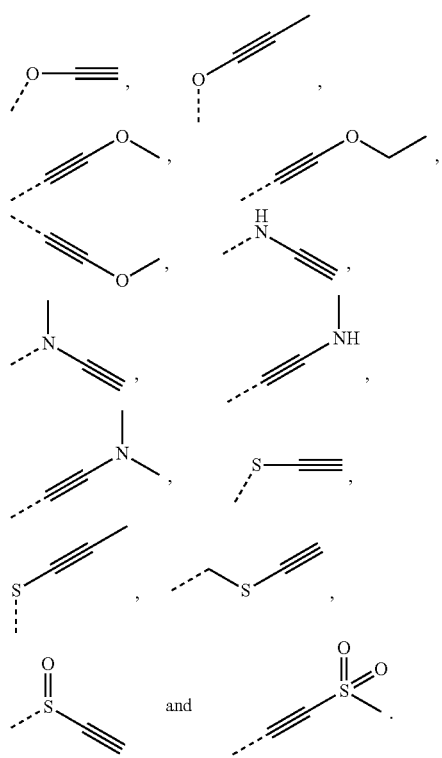

Up to two heteroatoms may be consecutive, for example,

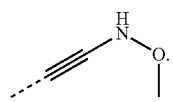

Unless otherwise specified, "cycloalkyl" includes any stable cyclic alkyl including a monocyclic, bicyclic or tricyclic ring system, wherein the bicyclic and tricyclic ring systems include a spiro ring, a fused ring, and a bridge ring. In some embodiments, the cycloalkyl is $C_{3-8}$ cycloalkyl. In other embodiments, the cycloalkyl is $C_{3-6}$ cycloalkyl. In other embodiments, the cycloalkyl is $C_{5-6}$ cycloalkyl. It may be mono-substituted or poly-substituted, and may be monovalent, divalent or polyvalent. Examples of the cycloalkyl include, but are not limited to, cyclopropyl, cyclobutyl, cyclopentyl, cyclohexyl, cycloheptyl, norbornyl, [2.2.2] bicyclooctane, and [4.4.0] bicyclodecane.

Unless otherwise specified, "cycloalkenyl" includes any stable cyclic alkenyl containing one or more unsaturated carbon-carbon double bonds at any position of the group, which includes a monocyclic, bicyclic or tricyclic system, wherein the bicyclic and tricyclic ring systems include a spiro ring, a fused ring, and a bridge ring, but any ring in the systems is non-aromatic. In some embodiments, the cycloalkenyl is $C_{3-8}$ cycloalkenyl. In other embodiments, the cycloalkenyl is $C_{3-6}$ cycloalkenyl. In other embodiments, the cycloalkenyl is $C_{5-6}$ cycloalkenyl. It may be mono-substituted or poly-substituted, and may be monovalent, divalent or polyvalent. Examples of the cycloalkenyl include, but are not limited to, cyclopentenyl and cyclohexenyl.

Unless otherwise specified, "cycloalkynyl" includes any stable cyclic alkynyl containing one or more carbon-carbon triple bonds at any position of the group, which includes a monocyclic, bicyclic or tricyclic ring system, wherein the bicyclic and tricyclic ring systems include a spiro ring, a fused ring, and a bridge ring. It may be mono-substituted or poly-substituted, and may be monovalent, divalent or polyvalent.

Unless otherwise specified, the term "heterocycloalkyl" by itself or in combination with other terms respectively represents a cyclized "heteroalkyl" group, which includes a monocyclic, bicyclic or tricyclic ring system, wherein the bicyclic and tricyclic ring systems include a spiro ring, a fused ring, and a bridge ring. In addition, in terms of the "heterocycloalkyl", the heteroatom may occupy the connection position of the heterocyclic alkyl to the remainder of the molecule. In some embodiments, the heterocycloalkyl is 4- to 6-membered heterocycloalkyl. In other embodiments, the heterocycloalkyl is 5- to 6-membered heterocycloalkyl. Examples of heterocycloalkyl include, but are not limited to, azetidinyl, oxetanyl, thiatanyl, pyrrolidinyl, pyrazolidinyl, imidazolidinyl, tetrahydrothienyl (including tetrahydrothien-2-yl and tetrahydrothien-3-yl), tetrahydrofiranyl (including tetrahydrofiran-2-yl), tetrahydropyranyl, piperidinyl (including 1-piperidinyl, 2-piperidinyl and 3-piperidinyl), piperazinyl (including 1-piperazinyl and 2-piperazinyl), morpholinyl (including 3-morpholinyl and 4-morpholinyl), dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

Unless otherwise specified, the term "heterocycloalkenyl" by itself or in combination with other terms respectively represents a cyclized "heteroalkenyl" group, which includes a monocyclic, bicyclic and tricyclic ring system, wherein the bicyclic and tricyclic ring systems include a spiro ring, a fused ring, and a bridge ring, but any ring in the systems is non-aromatic. In addition, in terms of the "heterocycloalkenyl", the heteroatom may occupy the connection position of the heterocycloalkenyl to the remainder of the molecule. In some embodiments, the heterocycloalkenyl is 4- to 6-membered heterocycloalkenyl. In other embodiments, the heterocycloalkenyl is 5- to 6-membered heterocycloalkenyl. Examples of heterocycloalkenyl groups include but are not limited to,

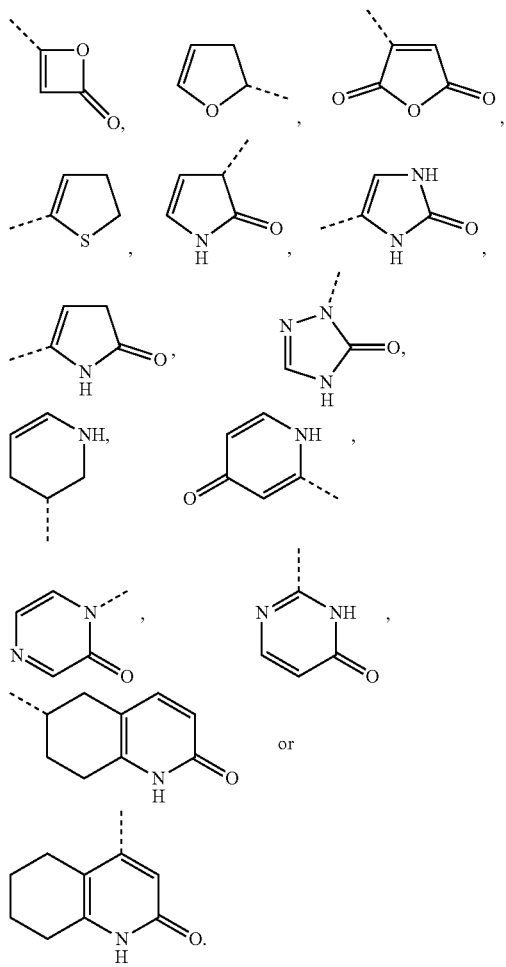

Unless otherwise specified, the term "heterocycloalkynyl" by itself or in combination with other terms respectively represents a cyclized "heteroalkynyl" group, which includes a monocyclic, bicyclic and tricyclic ring system, wherein the bicyclic and tricyclic ring systems include a spiro ring, a fused ring, and a bridge ring. In addition, in terms of the "heterocycloalkynyl", the heteroatom may occupy the connection position of the heterocycloalkynyl with the remainder of the molecule. In some embodiments, the heterocycloalkynyl is 4- to 6-membered heterocycloalkynyl. In other embodiments, the heterocycloalkynyl is 5- to 6-membered heterocycloalkynyl. Unless otherwise specified, the term "halo" or "halogen" by itself or as part of another substituent means a fluorine, chlorine, bromine or iodine atom. In addition, the term "haloalkyl" is intended to include monohaloalkyl and polyhaloalkyl. For example, the term "halo($C_1$-$C_4$)alkyl" is intended to include, but is not limited to, trifluoromethyl, 2,2,2-trifluoroethyl, 4-chlorobutyl and 3-bromopropyl. Unless otherwise specified, examples of haloalkyl include, but are not limited to: trifluoromethyl, trichloromethyl, pentafluoroethyl and pentachloroethyl.

"Alkoxy" represents the above alkyl having a specific number of carbon atoms connected via an oxygen bridge. Unless otherwise specified, $C_{1-6}$ alkoxy includes $C_1$, $C_2$, $C_3$, $C_4$, $C_5$ and $C_6$ alkoxy. In some embodiments, the alkoxy is $C_{1-3}$ alkoxy. Examples of alkoxy include, but are not limited to: methoxy, ethoxy, n-propoxy, isopropoxy, n-butoxy, sec-butoxy, tert-butoxy, n-pentoxy and S-pentoxy.

Unless otherwise specified, the terms "aromatic ring" and "aryl" in the present disclosure can be used interchangeably. The term "aromatic ring" or "aryl" means a polyunsaturated carbocyclic system, which may be a monocyclic, bicyclic or tricyclic system, in which at least one ring is aromatic, and the rings in the bicyclic and polycyclic ring systems are fused together. It may be mono-substituted or poly-substituted, and may be monovalent, divalent, or polyvalent. In some embodiments, the aryl is $C_{6-12}$ aryl. In other embodiments, the aryl is $C_{6-10}$ aryl. Examples of aryl include, but are not limited to, phenyl, naphthyl (including 1-naphthyl and 2-naphthyl). The substituent of any one of the above aryl ring systems is selected from the acceptable substituents described in the present disclosure.

Unless otherwise specified, the terms "heteroaryl ring" and "heteroaryl" of the present disclosure can be used interchangeably. The term "heteroaryl" refers to aryl (or aromatic ring) containing 1, 2, 3 or 4 heteroatoms independently selected from B, N, O and S, which may be a monocyclic, bicyclic or tricyclic ring system, wherein the nitrogen atom may be substituted or unsubstituted (i.e., N or NR, wherein R is H or other substituents already defined herein), and optionally quaternized, and the nitrogen and sulfur heteroatoms may be optionally oxidized (i.e., NO and $S(O)_p$, wherein p is 1 or 2). Heteroaryl can be connected to the remainder of the molecule via a heteroatom. In some embodiments, the heteroaryl is 5- to 10-membered heteroaryl. In other embodiments, the heteroaryl is 5- to 6-membered heteroaryl. Examples of the heteroaryl include, but are not limited to, pyrrolyl (including N-pyrrolyl, 2-pyrrolyl and 3-pyrrolyl), pyrazolyl (including 2-pyrazolyl and 3-pyrazolyl), imidazolyl (including N-imidazolyl, 2-imidazolyl, 4-imidazolyl and 5-imidazolyl), oxazolyl (including 2-oxazolyl, 4-oxazolyl and 5-oxazolyl), triazolyl (1H-1,2,3-triazolyl, 2H-1,2,3-tiazolyl, 1H-1,2,4-tiazolyl and 4H-1,2,4-triazolyl), tetrazolyl, isoxazolyl (3-isoxazolyl, 4-isoxazolyl, and 5-isoxazolyl), thiazolyl (including 2-thiazolyl, 4-thiazole and 5-thiazolyl), furyl (including 2-furanyl and 3-furanyl), thienyl (including 2-thienyl and 3-thienyl), pyridyl (including 2-pyridyl, 3-pyridyl and 4-pyridyl), pyrazinyl, pyrimidinyl (including 2-pyrimidinyl and 4-pyrimidinyl), benzothiazolyl (including 5-benzothiazolyl), purinyl, benzimidazolyl (including 2-benzimidazolyl), indolyl (including 5-indolyl), isoquinolinyl (including 1-isoquinolinyl and 5-isoquinolinyl), quinoxalinyl (including 2-quinoxalinyl and 5-quinoxalinyl), quinolinyl (including 3-quinolinyl and 6-quinolinyl), pyrazinyl, purinyl, and benzoxazolyl. The substituent of any one of the above heteroaryl ring systems is selected from the acceptable substituents described in the present disclosure.

Unless otherwise specified, the term "aralkyl" is intended to include those groups where an aryl group is attached to an alkyl group, and in some embodiments, the aralkyl is $C_{6-10}$ aryl-$C_{1-4}$ alkyl. In other embodiments, the aralkyl is $C_{6-10}$ aryl-$C_{1-2}$ alkyl. Examples of aralkyl include, but are not limited to, benzyl, phenethyl, and naphthylmethyl. "Aryloxy" and "arylthio" respectively represent those groups in which the carbon atom (such as methyl) in the aralkyl group is replaced by an oxygen or sulfur atom, and in some embodiments, the aryloxy is $C_{6-10}$ aryl-O—$C_{1-2}$ alkyl. In embodiments, the aryloxy is $C_{6-10}$ aryl-$C_{1-2}$ alkyl-O—. In other embodiments, the arylthio is $C_{6-10}$ aryl-S—$C_{1-2}$ alkyl. In other embodiments, the arylthio is $C_{6-10}$ aryl-$C_{1-2}$ alkyl- S—. Examples of aryloxy and arylthio include, but are not limited to, phenoxymethyl, 3-(1-naphthyloxy)propyl, and phenylthiomethyl.

Unless otherwise specified, the term "heteroaralkyl" is intended to include those groups where a heteroaryl group is attached to an alkyl group, and in some embodiments, the heteroaralkyl is 5- to 8-membered heteroaryl-$C_{1-4}$ alkyl. In other embodiments, the heteroaralkyl is 5- to 6-membered heteroaryl-$C_{1-2}$ alkyl. Examples of heteroaralkyl include, but are not limited to, pyrrolylmethyl, pyrazolylmethyl, pyridylmethyl, and pyrimidinylmethyl. "Heteroaryloxy" and "heteroarylthio" respectively represent those groups in which the carbon atom (such as methyl) in the heteroaralkyl group is replaced by an oxygen or sulfur atom, and in some embodiments, the heteroaryloxy is 5- to 8-membered heteroaryl-O—$C_{1-2}$ alkyl. In other embodiments, the heteroaryloxy is 5- to 6-membered heteroaryl-$C_{1-2}$ alkyl-O—. In some embodiments, the heteroarylthio is 5- to 8-membered heteroaryl-S—$C_{1-2}$ alkyl. In other embodiments, the heteroarylthio is 5- to 6-membered heteroaryl-$C_{1-2}$ alkyl-S—. Examples of heteroaryloxy and heteroarylthio include, but are not limited to, pyrroleoxymethyl, pyrazolyloxymethyl, 2-pyridyloxymethyl, pyrrolylmethyl, pyrazolylmethyl, and 2-pyridylthiomethyl.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, and also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$; Similarly, n-membered to n+m-membered means that the number of atoms in the ring is n to n+m, for example, a 3- to 12-membered ring includes a 3-membered ring, a 4-membered ring, a 5-membered ring, a 6-membered ring, a 7-membered ring, a 8-membered ring, a 9-membered ring, a 10-membered ring, a 11-membered ring, and a 12-membered ring, and also includes any range from n to n+m, for example, a 3- to 12-membered ring includes a 3- to 6-membered ring, a 3- to 9-membered ring, a 5- to 6-membered ring, a 5- to 7-membered ring, a 6- to 7-membered ring, a 6- to 8-membered ring, and a 6- to 10-membered ring.

The term "leaving group" refers to a functional group or atom that can be substituted by another functional group or atom through a substitution reaction (e.g., an affinity substitution reaction). For example, representative leaving groups include trifluoromethanesulfonate; chlorine, bromine and iodine; sulfonates, such as methanesulfonate, tosylate, p-bromobenzenesulfonate, and p-toluenesulfonate; and acyloxy, such as acetoxy and trifluoroacetoxy.

The term "protecting group" includes, but is not limited to, "amino protecting group", "hydroxyl protecting group" or "mercapto protecting group". The term "amino protecting group" refers to a protecting group suitable for preventing side reactions occur at the nitrogen atom of an amino group. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl)methyl; silyl, such as trimethylsilyl (TMS) and tert-butyldimethylsilyl (TBS). The term "hydroxyl protecting group" refers to a protecting group suitable for preventing side reactions of a hydroxyl group. Representative hydroxyl protecting groups include, but are not limited to: alkyl, such as methyl, ethyl and tert-butyl; acyl, such as alkanoyl (e.g., acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyldimethylsilyl (TBS).

The compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The solvents used in the present disclosure are commercially available. The present disclosure uses the following abbreviations: aq represents water; HATU represents O-(7-azabenzotriazol-1-yl)-N,N,N',N'-tetramethylurea hexafluorophosphate; EDC represents N-(3-dimethylaminopropyl)-N'-ethylcarbodiimide hydrochloride; m-CPBA represents 3-chloroperoxybenzoic acid; eq represents equivalent; mol represents mole; mmol represents millimole; kg represents kilogram; g represents gram; mg represents milligram; L represents liter; ml represents milliliter; mm represents millimeter; μm represents micrometer; CDI represents carbonyldiimidazole; DCM represents dichloromethane; DCE represents 1,2-dichloroethane; $AlCl_3$ represents aluminum trichloride; $NH_4Cl$ represents ammonium chloride; $Na_2SO_3$ represents sodium sulfite; NaCl represents sodium chloride; $Na_2SO_4$ represents sodium sulfate; LiOH represents lithium hydroxide; NaOH represents sodium hydroxide; t-BuOK represents potassium tert-butoxide; $K_3PO_4$ represents potassium phosphate; CuI represents cuprous iodide; $NaHCO_3$ represents sodium bicarbonate; $SnCl_2$ represents tin dichloride; $Cs_2CO_3$ represents strontium carbonate; $Na_2CO_3$ represents sodium carbonate; $Na_2S_2O_3$ represents sodium thiosulfate; $K_2CO_3$ represents potassium carbonate; KOAc represents potassium acetate; NaH represents sodium hydrogen; KHMDS represents potassium bis(trimethylsilyl)amide; DIEA represents N,N-diisopropylethylamine; DMEDA represents N,N'-dimethylethylenediamine; $NH_3.H_2O$ represents ammonia water; NMP represents N-methylpyrrolidone; NBS represents N-bromosuccinimide; THF represents tetrahydrofiran; PE represents petroleum ether; DIAD represents diisopropyl azodicarboxylate; DMF represents N,N-dimethylformamide; DMSO represents dimethyl sulfoxide; EtOAc or EA represents ethyl acetate; EtOH represents ethanol; MeOH represents methanol; MTBE represents methyl tert-butyl ether; FA represents formic acid; CAN represents acetonitrile; CBz represents benzyloxycarbonyl, which is an amine protecting group; BOC represents tert-butoxycarbonyl, which is an amine protecting group; HOAc represents acetic acid; $NaCNBH_3$ represents sodium cyanoborohydride; DMAP represents 4-dimethylaminopyridine; r.t. represents room temperature; O/N represents overnight; $Boc_2O$ represents di-tert-butyl dicarbonate; TFA represents trifluoroacetic acid; DIPEA represents diisopropylethylamine; $SOCl_2$ represents thionyl chloride; $CS_2$ represents carbon disulfide; TsOH represents p-toluenesulfonic acid; $CH_3I$ or MeI represents methyl iodide; $CH_2Br_2$ represents dibromomethane; $CH_2I_2$ represents diiodomethane; DPPA represents diphenylphosphoryl azide; NCS represents N-chlorosuccinimide; LDA represents lithium diisopropylamide; $T_3P$ represents 1-propyl phosphoric anhydride; tBuXPhos Pd G3 represents methanesulfonato(2-di-tert-butylphosphino-2',4',6'-triisopropyl-1,1'-biphenyl)(2'-amino-1,1'-biphenyl-2-yl) palladium (II); $Pd_2(dba)_3$ represents tris(dibenzylideneacetone)dipalladium; Xantphos represents 4,5-bisdiphenylphosphino-9,9-dimethylxanthene; Pd(dppf)$Cl_2CH_2Cl_2$ represents [1,1'-bis(diphenylphosphino)

ferrocene]palladium dichloride dichloromethane complex; Pd(PPh$_3$)$_4$ represents tetrakistriphenylphosphine palladium; XPHOS-PD-G2 represents chloro(2-dicyclohexylphosphino-2',4',6'-triisopropyl-1,1'-biphenyl)[2-(2'-amino-1,1'-biphenyl)]palladium (II); TEA represents triethylamine; sPHOS-PD-G2 represents chloro(2-dicyclohexylphosphino-2',6'-dimethoxy-1,1'-biphenyl)(2'-amino-1,1'-biphenyl-2-yl) palladium (II); TLC represents thin layer chromatographic separation; HPLC represents high performance liquid chromatographic separation; SFC represents supercritical fluid chromatographic separation.

Compounds are named by hand or ChemDraw® software, and commercially available compounds are named by the supplier catalog names.

DETAILED DESCRIPTION OF EMBODIMENTS

The present disclosure will be described in detail with the following examples, but not imply any adverse limitation to the present disclosure. The present disclosure has been described in detail herein, and the specific embodiments thereof are also disclosed therein. For a person skilled in the art, without departing from the spirit and scope of the present disclosure, all the variations and improvements made to the specific embodiments of the present disclosure would have been obvious.

Example 1

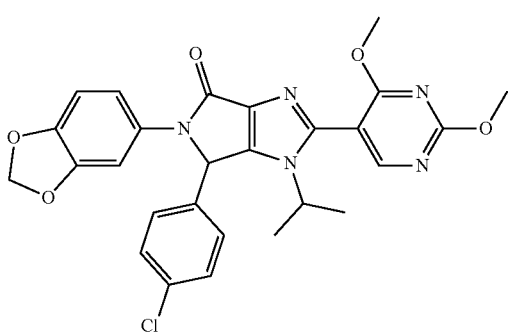

1-I and 1-II

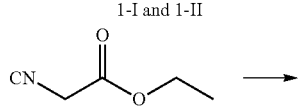

1-1

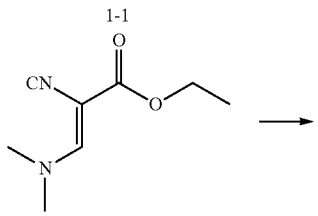

1-a

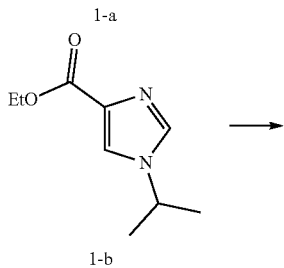

1-b

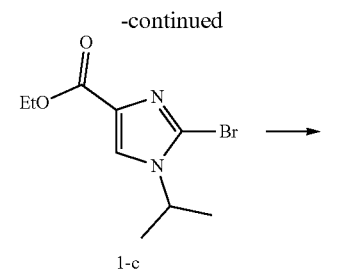

1-c

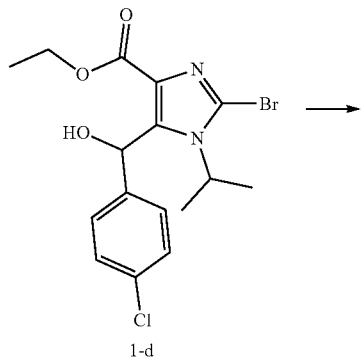

1-d

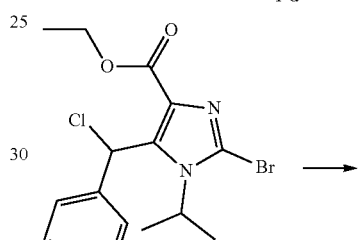

1-e

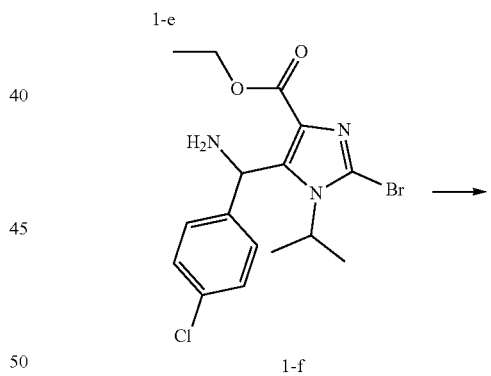

1-f

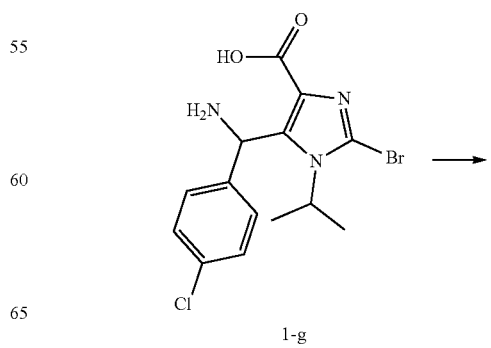

1-g

-continued

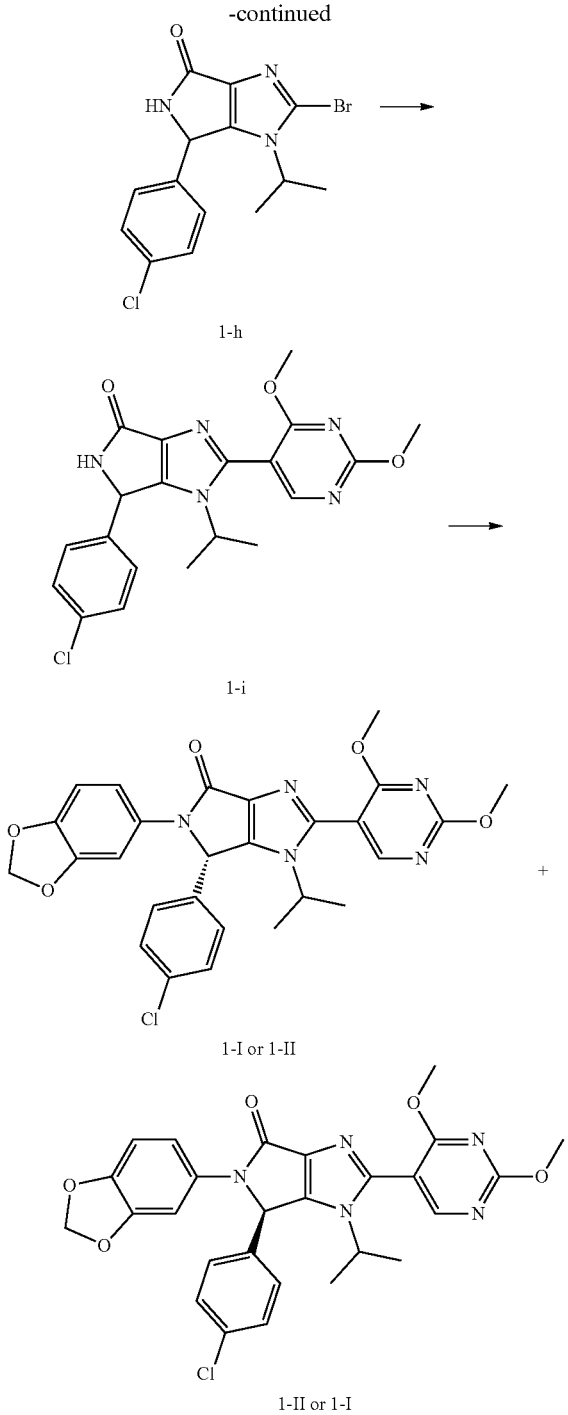

1-h 1-i

1-I or 1-II

1-II or 1-I

Step A: At 25° C., to a solution of compound 1-1 (2.00 kg, 17.68 mol, 1.94 L, 1.00 eq) in EtOH (25.00 L) was added dropwise N,N-dimethylformamide dimethylacetal (2.74 kg, 22.98 mol, 3.04 L, 1.30 eq), and the reaction solution was stirred for 16 hours. The reaction solution was concentrated under reduced pressure to obtain a crude product. The crude product was purified and separated by a silica gel chromatographic column (V/V) (PE:EA=1:0-2.5:1) to obtain compound 1-a (2.5 kg, yield: 84.07%).

Step B: At 25° C., to the compound 1-a (2.50 kg, 14.86 mol, 1.00 eq) was added 2-propylamine (2.64 kg, 44.58 mol, 3.82 L, 3.00 eq), and the reaction solution was heated to 85° C. and stirred for 16 hours. The reaction solution was cooled to room temperature, and then concentrated under reduced pressure to obtain compound 1-b (2.4 kg, yield: 88.63%).

Step C: At 25° C., to a solution of the compound 1-b (1.20 kg, 6.59 mol, 1.00 eq) in THF (30.00 L) were added $K_3PO_4$ (3.70 kg, 17.43 mol, 2.65 eq) and NBS (2.50 kg, 14.05 mol, 2.13 eq), and stirred for 12 hours. The reaction solution was filtered, and the filtrate was added with 20 L saturated $Na_2SO_3$ solution, and extracted with EA (10 L*2); the organic phases were combined, washed with saturated brine (10 L*2), dried over anhydrous sodium sulfate and then filtered, and the filtrate was concentrated under reduced pressure to obtain a crude product. The crude product was purified and separated by a silica gel chromatographic column (V/V) (PE:EA=1:0-1:1) to obtain compound 1-c (1.03 kg, yield: 59.85%).

Step D: At −70° C. under nitrogen protection, to a solution of the compound 1-c (50 g, 191.49 mmol, 1 eq) in THF (500 mL) was added dropwise slowly LDA (2 M, 150 mL, 1.57 eq), and after stirring for 0.5 hour, a solution of 4-chlorobenzaldehyde (32.30 g, 229.78 mmol, 1.2 eq) in THF (30 mL) was added slowly to the reaction solution, and stirred for 1.5 hours at −70° C. after the dropwise addition was complete. $NH_4Cl$ (200 mL) was added to the reaction solution and extracted with EA (300 mL*2); the organic phases were combined, washed with water and saturated brine, dried over anhydrous sodium sulfate and then filtered, and the filtrate was concentrated under reduced pressure to obtain a crude product. The crude product was purified and separated by a silica gel chromatographic column (V/V) (PE:EA=10:1-3:1) to obtain compound 1-d (12 g, yield: 15.62%).

Step E: At 25° C., to a solution of the compound 1-d (12 g, 29.87 mmol, 1 eq) in DCM (120 mL) was added $SOCl_2$ (21.32 g, 179.25 mmol, 13.00 mL, 6 eq), and stirred for 1 hour. Water (80 mL) was slowly added to the reaction solution, and the organic phase was separated, washed with saturated brine, dried over anhydrous sodium sulfate and filtered, and then the filtrate was concentrated under reduced pressure to obtain compound 1-e (9 g, yield: 71.66%).

Step F: At 25° C., to a solution of the compound 1-e (9.00 g, 21.42 mmol, 1.00 eq) in dioxane (30.00 mL) was added $NH_3.H_2O$ (12.85 g, 128.31 mmol, 661.14 μL, purity: 35%, 5.99 eq), and stirred for 2 hours. The saturated ammonium chloride (30 mL) solution was slowly added to the reaction solution, and extracted with EA (60 mL*2); the organic phases were combined, washed with saturated brine (30 mL), dried over anhydrous sodium sulfate and filtered, and then the filtrate was concentrated under reduced pressure to obtain a crude product. The crude product was purified and separated by a silica gel chromatographic column (V/V) (PE:EA=3:1-1:1) to obtain compound 1-f (8.86 g, the crude product was directly used in the next step).

Step G: At 25° C., to a solution of the compound 1-f (8.86 g, 21.01 mmol, 1.00 eq) in THF (40.00 mL), EtOH (30.00 mL) and $H_2O$ (30.00 mL) was added LiOH (2.01 g, 84.04 mmol, 4.00 eq), and stirred for 12 hours. The reaction solution was concentrated under reduced pressure to remove EtOH and THF. The residue was extracted with EA (80 mL), and the aqueous phase was adjusted to PH=3 with HCl (3 M)

until solid production, and filtered, then the filter cake was dissolved in toluene and concentrated under reduced pressure to obtain compound 1-g (6.43 g, yield: 78%).

Step H: At 25° C., to a solution of the compound 1-g (6.43 g, 15.52 mmol, 1.00 eq) in DMF (60.00 mL) were added HATU (8.85 g, 23.28 mmol, 1.50 eq) and DIPEA (4.01 g, 31.04 mmol, 5.42 mL, 2.00 eq) respectively, and the reaction solution was stirred at 60° C. for 12 hours. After the reaction solution was cooled to room temperature, water (200 mL) was added to the reaction solution and extracted with EA (80 mL*3); the organic phases were combined, washed with water (50 mL*2) and saturated brine (50 mL) respectively, dried over anhydrous sodium sulfate, filtered and concentrated under reduced pressure to obtain compound 1-h (2.5 g, yield: 40.85%).

Step I: At 25° C., to a solution of the compound 1-h (2.5 g, 7.05 mmol, 1.00 eq) in dioxane (35.00 mL) and water (7.00 mL) were added 2,4-dimethoxypyrimidine-5-boronic acid (1.95 g, 10.57 mmol, 1.50 eq), $K_3PO_4$ (2.24 g, 10.57 mmol, 1.50 eq) and Pd(dppf)$Cl_2$.$CH_2Cl_2$ (287.85 mg, 352.48 µmol, 0.05 eq) respectively, and the reaction system was replaced with nitrogen three times, heated to 100° C. and stirred for 12 hours in a nitrogen atmosphere. After the reaction solution was cooled to room temperature, the saturated ammonium chloride (30 mL) solution was slowly added to the reaction solution, and extracted with EA (60 mL*2); the organic phases were combined, washed with saturated brine (30 mL), dried over anhydrous sodium sulfate, filtered, and concentrated under reduced pressure to obtain a crude product. The crude product was purified and separated by a silica gel chromatographic column (V/V) (PE:EA=1:0-3:1, EA:DCM=1:1-4:1) to obtain compound 1-i (1.9 g, yield: 60.56%).

Step J: At 25° C., to a solution of the compound 1-i (300 mg, 674.15 µmol, 1.00 eq) and 4-bromo-1,2-methylenedioxybenzene (271.03 mg, 1.35 mmol, 161.33 µL, 2.00 eq) in dioxane (10 mL) were added $Cs_2CO_3$ (439.30 mg, 1.35 mmol, 2.00 eq), CuI (64.20 mg, 337.07 µmol, 0.50 eq) and DMEDA (59.43 mg, 674.15 µmol, 72.56 µL, 1.00 eq) respectively, and the reaction system was replaced with nitrogen three times, heated to 70° C. and stirred for 12 hours in a nitrogen atmosphere. The reaction solution was cooled to room temperature, filtered and concentrated under reduced pressure to obtain a crude product. The crude product was purified and separated by a preparative plate (V/V) (PE:EA=0:1) and SFC (column: AD (250 mm*30 mm, 10 µm); mobile phase: [0.1% ammonia water, methanol]; [0.1% ammonia water, methanol]%: 55%-55%) to obtain compound 1-I (retention time: 2.974 min, 38 mg, yield: 10.5%) and compound 1-I (retention time: 3.487 min, 40 mg, yield: 10.81%).

1-I: $^1$H NMR (400 MHz, DMSO-$d_6$): δ=8.47 (s, 1H), 7.42-7.38 (m, 4H), 7.11 (d, J=1.8 Hz, 1H), 6.98-6.86 (m, 1H), 6.84-6.78 (m, 1H), 6.61 (s, 1H), 5.97 (d, J=12.8 Hz, 2H), 4.11 (td, J=6.7, 13.5 Hz, 1H), 3.98 (s, 3H), 3.93 (s, 3H), 1.38 (d, J=6.7 Hz, 3H), 0.50 (d, J=6.7 Hz, 3H). MS (ESI) m/z: 534.2 (M+H)$^+$.

1-II: $^1$H NMR (400 MHz, DMSO-$d_6$): δ=8.48 (s, 1H), 7.42-7.38 (m, 4H), 7.11 (s, 1H), 6.91 (d, J=8.4 Hz, 1H), 6.85-6.78 (m, 1H), 6.61 (s, 1H), 5.97 (d, J=12.9 Hz, 2H), 4.11 (td, J=6.7, 13.4 Hz, 1H), 3.98 (s, 3H), 3.93 (s, 3H), 1.38 (d, J=6.7 Hz, 3H), 0.50 (d, J=6.7 Hz, 3H). MS (ESI) m/z: 534.2 (M+H)$^+$.

Example 2

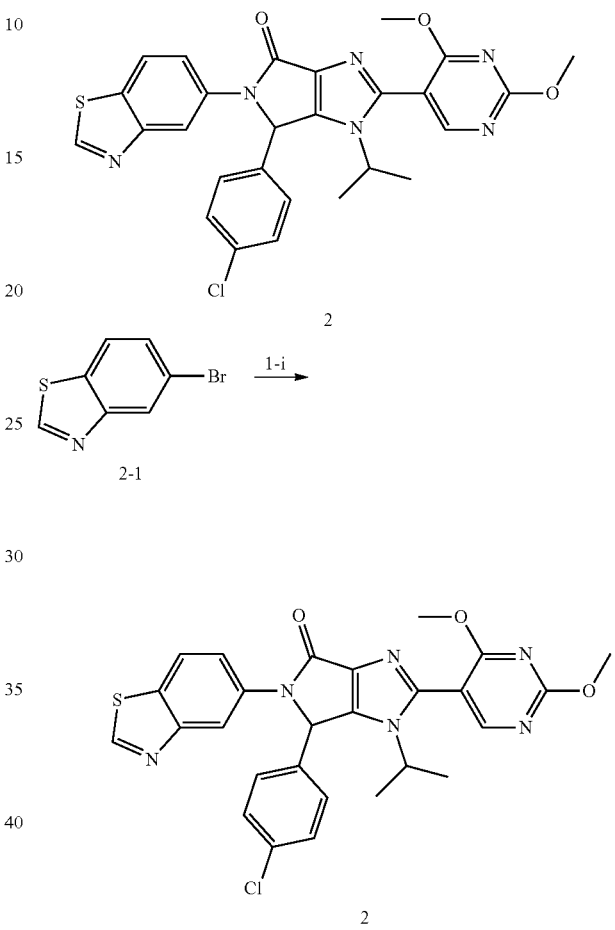

Step A: At room temperature under nitrogen protection, to a solution of the compound 1-i (150 mg, 337.07 µmol, 1 eq) and 5-bromobenzothiazole (144.32 mg, 674.15 µmol, 2 eq) in dioxane (8 mL) were added $Cs_2CO_3$ (219.65 mg, 674.15 µmol, 2 eq), XantPhos (39.01 mg, 67.41 µmol, 0.2 eq) and $Pd_2(dba)_3$ (61.73 mg, 67.41 µmol, 0.2 eq) respectively. The reaction system was replaced with nitrogen 3 times, heated to 90° C. and stirred for 12 hours. After cooling, the reaction solution was filtered and concentrated, and the residue was purified and separated by preparative TLC (V/V) (PE:EA=0:1) and preparative HPLC (column: Boston Green ODS 150 mm*30 mm 5 µm; mobile phase: [water (0.225% FA)-ACN]; ACN %: 43%-73%) to obtain compound 2 (7 mg, yield: 3.75%).

2: $^1$H NMR (400 MHz, DMSO-$d_6$): δ=9.38 (s, 1H), 8.51 (s, 1H), 8.29 (s, 1H), 8.07 (d, J=8.4 Hz, 1H), 7.74 (d, J=7.9 Hz, 1H), 7.55-7.35 (m, 4H), 6.92 (s, 1H), 4.15 (s, 1H), 4.00 (s, 3H), 3.95 (s, 3H), 1.43 (d, J=5.9 Hz, 3H), 0.52 (d, J=5.5 Hz, 3H). MS (ESI) m/z: 547.1 (M+H)$^+$.

Example 3

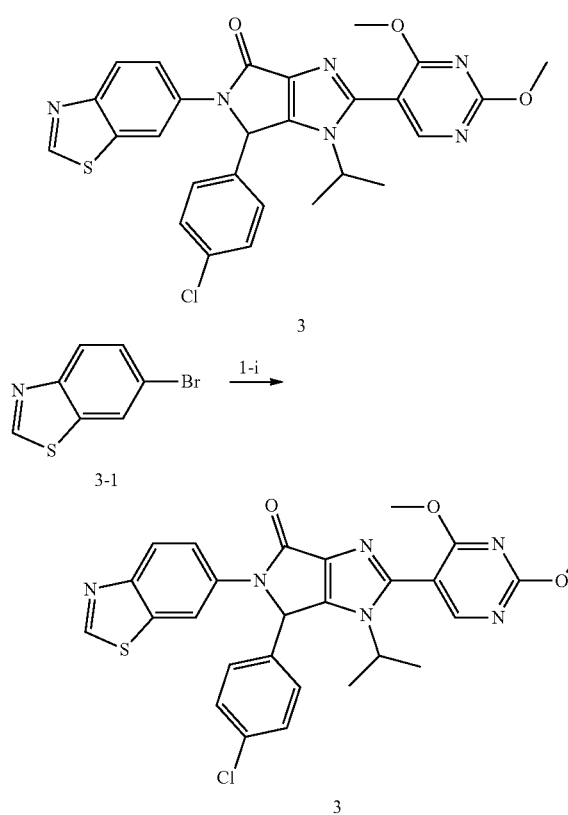

Step A: According to Step A of Example 2, 5-bromobenzothiazole was replaced with 6-bromo-1,3-benzothiazole. Purification and separation were performed by preparative TLC (V/V) (PE:EA=0:1) and preparative HPLC (column: Phenomenex Synergi C18 150 mm*25 mm*10 μm; mobile phase: [(0.225% FA)-ACN]; ACN %: 35%-65%) to obtain compound 3 (21 mg, yield: 11.24%).

3: $^1$H NMR (400 MHz, DMSO-d$_6$): δ=9.31 (s, 1H), 8.51 (s, 1H), 8.35 (s, 1H), 8.00 (d, J=8.8 Hz, 1H), 7.77 (d, J=8.8 Hz, 1H), 7.45 (s, 2H), 7.42-7.37 (m, 2H), 6.87 (s, 1H), 4.15 (td, J=6.6, 13.4 Hz, 1H), 4.00 (s, 3H), 3.95 (s, 3H), 1.43 (d, J=6.8 Hz, 3H), 0.52 (d, J=6.5 Hz, 3H). MS (ESI) m/z: 5471 (M+H)$^+$.

Example 4

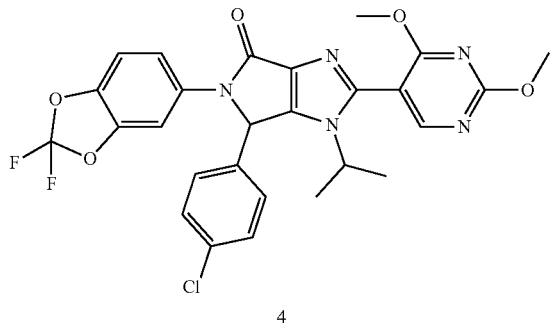

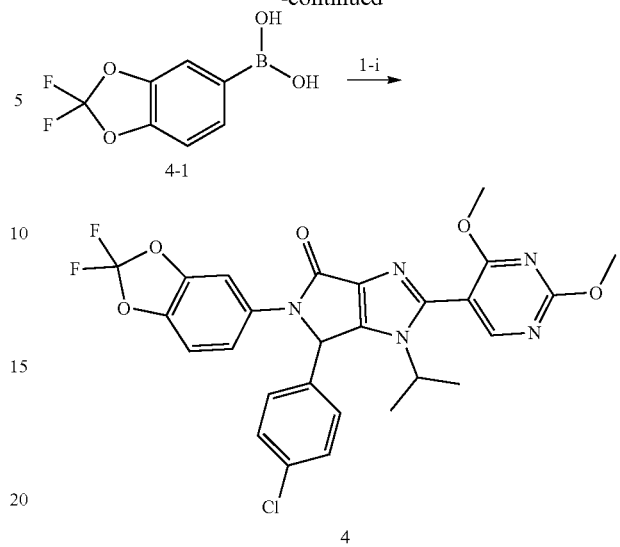

Step A: Under oxygen protection, to a solution of the compound 1-i (10 mg, 24.16 μmol, 1 eq) and compound 4-1 (7.32 mg, 36.24 μmol, 1.5 eq) in tetrahydrofuran (1 mL) were added copper acetate (8.78 mg, 48.33 μmol, 2 eq), triethylamine (9.78 mg, 96.65 μmol, 13.45 μL, 4 eq), pyridine (7.65 mg, 96.65 μmol, 7.80 μL, 4 eq) and 4A molecular sieve (24.16 mg, 241.63 μmol, 10 eq) respectively, and the reaction solution was heated to 50° C. and stirred for 12 hours. The reaction solution was filtered, the filter cake was washed with tetrahydrofuran (5 mL), and the filtrate was concentrated under reduced pressure. The residue was purified and separated by preparative TLC (EA) to obtain compound 4 (4.6 mg, yield: 33.3%).

4: $^1$H NMR (400 MHz, CDCl$_3$): δ=8.46 (s, 1H), 7.37-7.35 (m, 2H), 7.24-7.21 (m, 3H), 6.98-6.94 (m, 2H), 5.92 (s, 1H), 4.16-4.11 (m, 1H), 4.09 (s, 3H), 4.01 (s, 3H), 1.46 (d, J=6.8 Hz, 3H), 0.64 (d, J=6.8 Hz, 3H). MS (ESI) m/z: 570.1 (M+H)$^+$.

Example 5

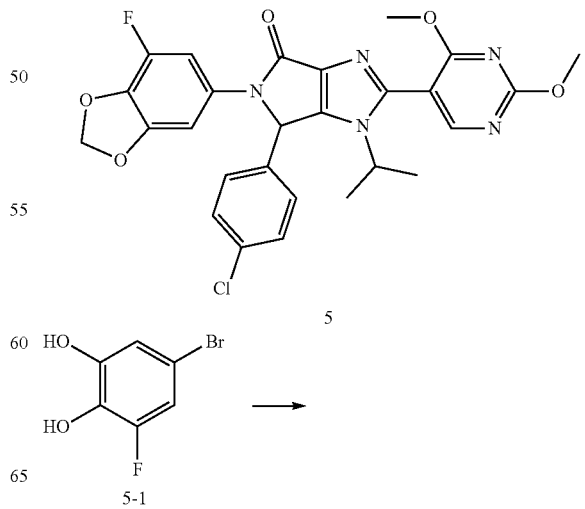

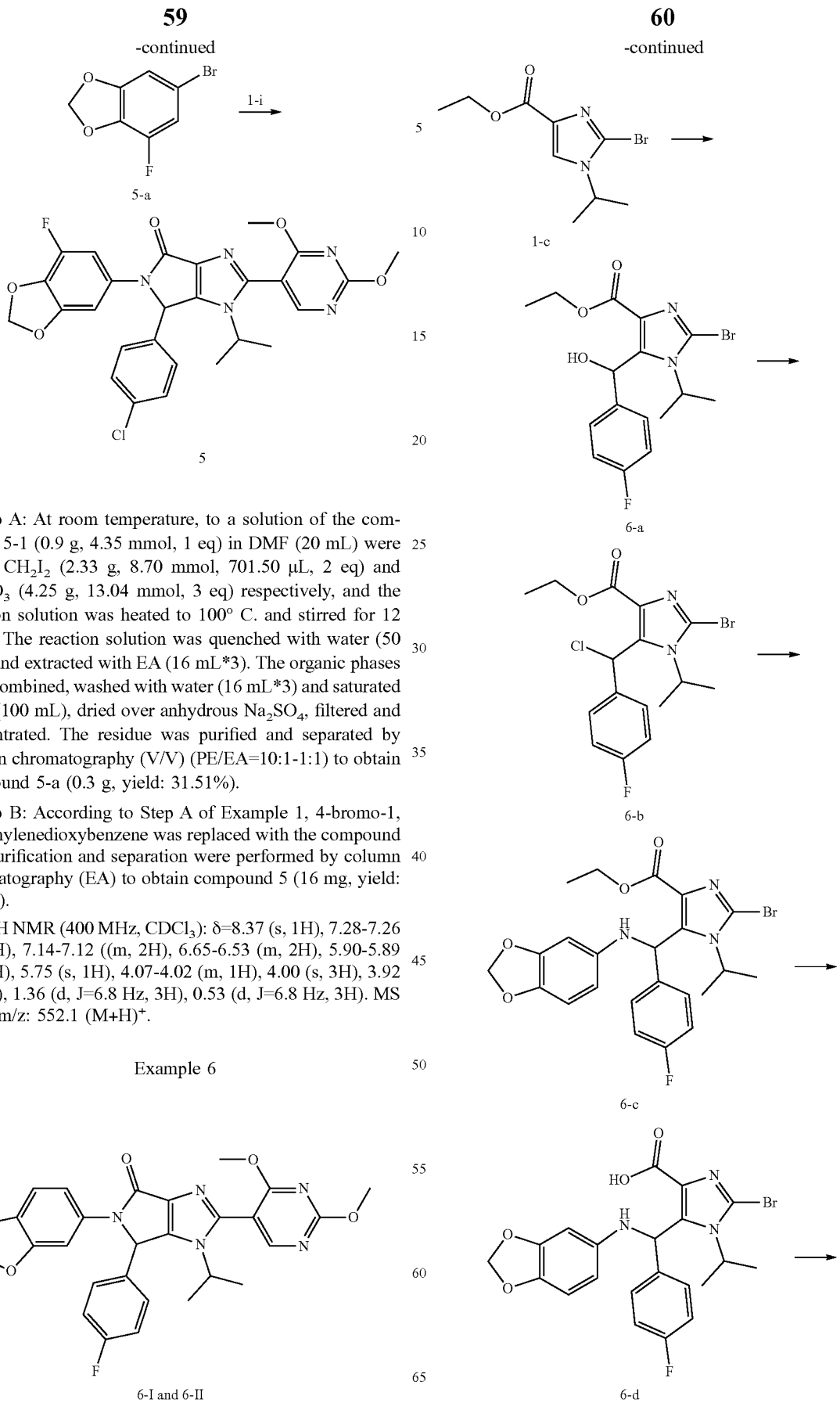

Step A: At room temperature, to a solution of the compound 5-1 (0.9 g, 4.35 mmol, 1 eq) in DMF (20 mL) were added $CH_2I_2$ (2.33 g, 8.70 mmol, 701.50 μL, 2 eq) and $Cs_2CO_3$ (4.25 g, 13.04 mmol, 3 eq) respectively, and the reaction solution was heated to 100° C. and stirred for 12 hours. The reaction solution was quenched with water (50 mL), and extracted with EA (16 mL*3). The organic phases were combined, washed with water (16 mL*3) and saturated brine (100 mL), dried over anhydrous $Na_2SO_4$, filtered and concentrated. The residue was purified and separated by column chromatography (V/V) (PE/EA=10:1-1:1) to obtain compound 5-a (0.3 g, yield: 31.51%).

Step B: According to Step A of Example 1, 4-bromo-1,2-methylenedioxybenzene was replaced with the compound 5-a. Purification and separation were performed by column chromatography (EA) to obtain compound 5 (16 mg, yield: 82.0%).

5: $^1$H NMR (400 MHz, $CDCl_3$): δ=8.37 (s, 1H), 7.28-7.26 (m, 2H), 7.14-7.12 ((m, 2H), 6.65-6.53 (m, 2H), 5.90-5.89 (m, 2H), 5.75 (s, 1H), 4.07-4.02 (m, 1H), 4.00 (s, 3H), 3.92 (s, 3H), 1.36 (d, J=6.8 Hz, 3H), 0.53 (d, J=6.8 Hz, 3H). MS (ESI) m/z: 552.1 (M+H)$^+$.

Example 6

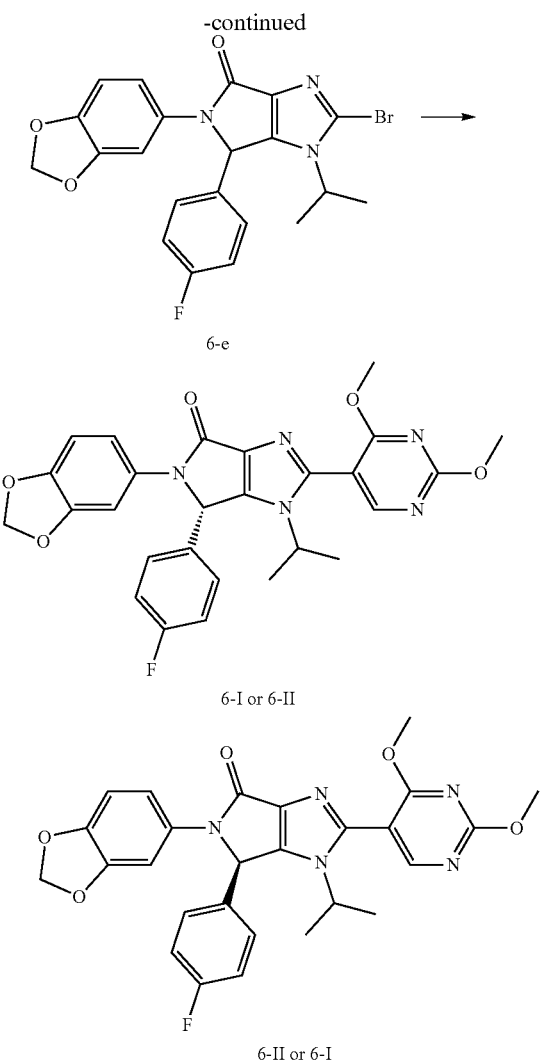

6-e

6-I or 6-II

6-II or 6-I

Step A: At −70° C. under nitrogen protection, to a solution of the compound 1-c (20 g, 76.59 mmol, 1.00 eq) in THF (150.00 mL) was added dropwise LDA (2 M, 76.59 mL, 2.00 eq) solution, and stirred for another 0.5 hour at −70° C. after the dropwise addition was complete. Subsequently, to the reaction solution was added dropwise a solution of p-fluorobenzaldehyde (9.51 g, 76.59 mmol, 8.06 mL, 1.0 eq) in THF (100 mL), and stirred for another 2.5 hours at −70° C. after the dropwise addition was complete. The reaction solution was quenched with 10% aqueous $NH_4Cl$ solution (1.2 L), and extracted with EA (500 mL*3). The organic layers were combined, washed with saturated brine (600 mL), dried over anhydrous $Na_2SO_4$, filtered and concentrated to obtain a crude product. The crude product was purified and separated by a silica gel chromatographic column (V/V) (PE:EA=5:1-1:1) to obtain compound 6-a (10.0 g, yield: 33.9%).

Step B: At 0° C., to a solution of the compound 6-a (10 g, 25.96 mmol, 1.00 eq) in DCM (20 mL) was added $SOCl_2$ (18.53 g, 155.75 mmol, 11.30 mL, 6.00 eq). The reaction solution was heated to 25° C. and stirred for 2 hours. The reaction solution was concentrated under reduced pressure, and the concentrated solution was diluted with toluene (100 mL) and concentrated under reduced pressure to obtain compound 6-b (10.0 g, yield: 95.43%).

Step C: At room temperature, to a solution of the compound 6-b (10 g, 24.77 mmol, 1 eq) and piperonylamine (3.74 g, 27.25 mmol, 1.1 eq) in acetonitrile (100 mL) was added DIPEA (9.61 g, 74.32 mmol, 12.94 mL, 3 eq), and the reaction solution was heated to 70° C. and stirred for 12 hours. The reaction solution was quenched with water (200 mL), and extracted with EA (100 mL*3). The organic layers were combined, washed with saturated brine (150 mL), dried over anhydrous $Na_2SO_4$, filtered and concentrated to obtain a crude product. The crude product was purified and separated by a silica gel chromatographic column (V/V) (PE:EA=5:1-1:1) to obtain compound 6-c (8.0 g, yield: 64.1%).

Step D: At room temperature, the compound 6-c (8 g, 15.86 mmol, 1 eq) and $LiOH.H_2O$ (2.66 g, 63.45 mmol, 4 eq) were added to a mixed solution of tetrahydrofuran (10 mL), ethanol (5 mL) and water (10 mL), and stirred for 12 hours at 25° C. The reaction solution was concentrated to remove ethanol and tetrahydrofuran, and the residue was adjusted to pH=3 with HCl (1M) and extracted with EA (30 mL*3); the organic phases were combined, washed with saturated brine (50 mL), dried over anhydrous $Na_2SO_4$, filtered and concentrated to obtain compound 6-d (5.0 g, yield: 66.18%).

Step E: At room temperature, to a solution of the compound 6-d (5 g, 10.50 mmol, 1 eq) in DMF (100 mL) were added HATU (5.99 g, 15.75 mmol, 1.5 eq) and DIPEA (4.07 g, 31.49 mmol, 5.49 mL, 3 eq) respectively, and the reaction solution was heated to 60° C. and stirred for 10 minutes. The reaction solution was quenched with water (150 mL) and extracted with EA (100 mL*3), and the organic phases were combined and washed with water (100 mL*3) and saturated brine (50 mL) respectively, dried over anhydrous $Na_2SO_4$, filtered and concentrated to obtain a crude product. The crude product was purified and separated by a silica gel chromatographic column (V/V) (PE:EA=3:1) to obtain compound 6-e (2.5 g, yield: 51.98%).

Step F: At room temperature under nitrogen protection, to a mixed solution of the compound 6-e (0.5 g, 1.09 mmol, 1 eq) in dioxane (15 mL) and water (6 mL) were added 2,4-dimethoxypyrimidine boronic acid (301.06 mg, 1.64 mmol, 1.5 eq), $K_3PO_4$ (694.78 mg, 3.27 mmol, 3 eq) and Xantphos (78.62 mg, 109.10 μmol, 0.1 eq) respectively, and the reaction solution was heated to 80° C. and stirred for 12 hours. The reaction solution was cooled to room temperature, quenched with water (50 mL), and extracted with EA (30 mL*3), and the organic phases were combined, washed with saturated brine (50 mL), dried over anhydrous $Na_2SO_4$, filtered and concentrated to obtain a crude product (0.14 g, yield: 20.12%). The crude product was purified by a silica gel chromatographic column (V/V) (PE:EA=1:2) and SFC (column: OJ (250 mm*30 mm, 10 μm); mobile phase: [0.1% ammonia water, methanol]; [0.1% ammonia water, methanol]%: 40%-40%) respectively to obtain compound 6-I (retention time: 1.863 min, 67 mg, yield: 45.46%) and compound 6-II (retention time: 2.864 min, 50 mg, yield: 33.93%).

6-I: 1H NMR (400 MHz, CDCl3): δ=8.47 (s, 1H), 7.24-7.22 (m, 2H), 7.07-7.05 (m, 2H), 6.83-6.82 (m, 1H), 6.70-6.67 (m, 2H), 5.93 (s, 2H), 5.92-5.84 (m, 1H), 4.15-4.10 (m, 1H), 4.09 (s, 3H), 4.02 (s, 3H), 1.45 (d, J=6.8 Hz, 3H), 0.64 (d, J=6.4 Hz, 3H). MS (ESI) m/z: 518.2 $(M+H)^+$.

6-II: 1H NMR (400 MHz, CDCl3): δ=8.47 (s, 1H), 7.24-7.22 (m, 2H), 7.07-7.05 (m, 2H), 6.83-6.82 (m, 1H), 6.70-6.67 (m, 2H), 5.93 (s, 2H), 5.92-5.84 (m, 1H), 4.15-4.10 (m, 1H), 4.09 (s, 3H), 4.02 (s, 3H), 1.45 (d, J=6.8 Hz, 3H), 0.64 (d, J=6.4 Hz, 3H). MS (ESI) m/z: 518.2 $(M+H)^+$.

Example 7

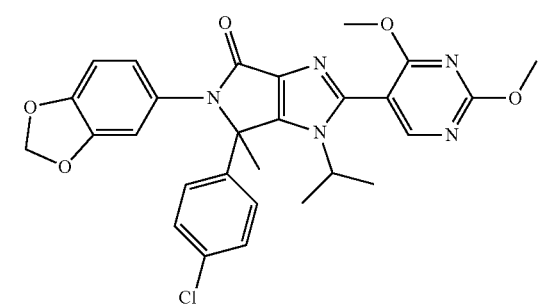

7-I and 7-II

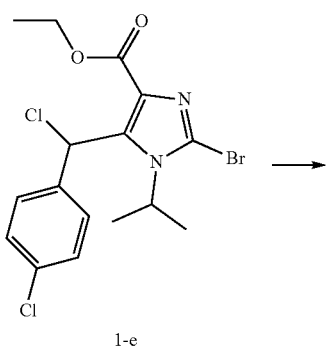

1-e

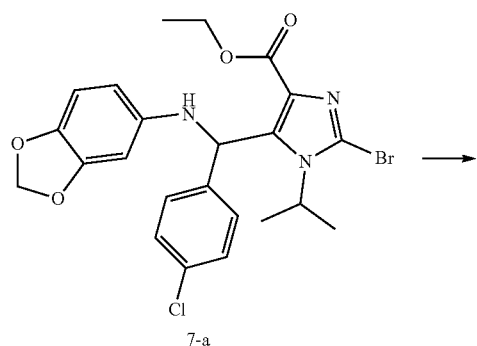

7-a

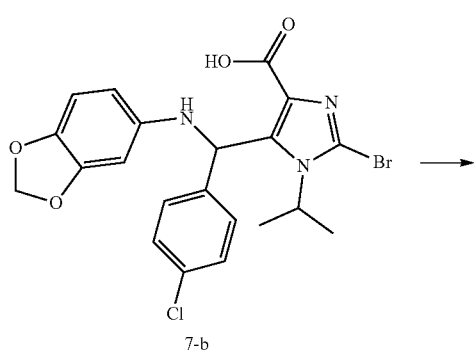

7-b

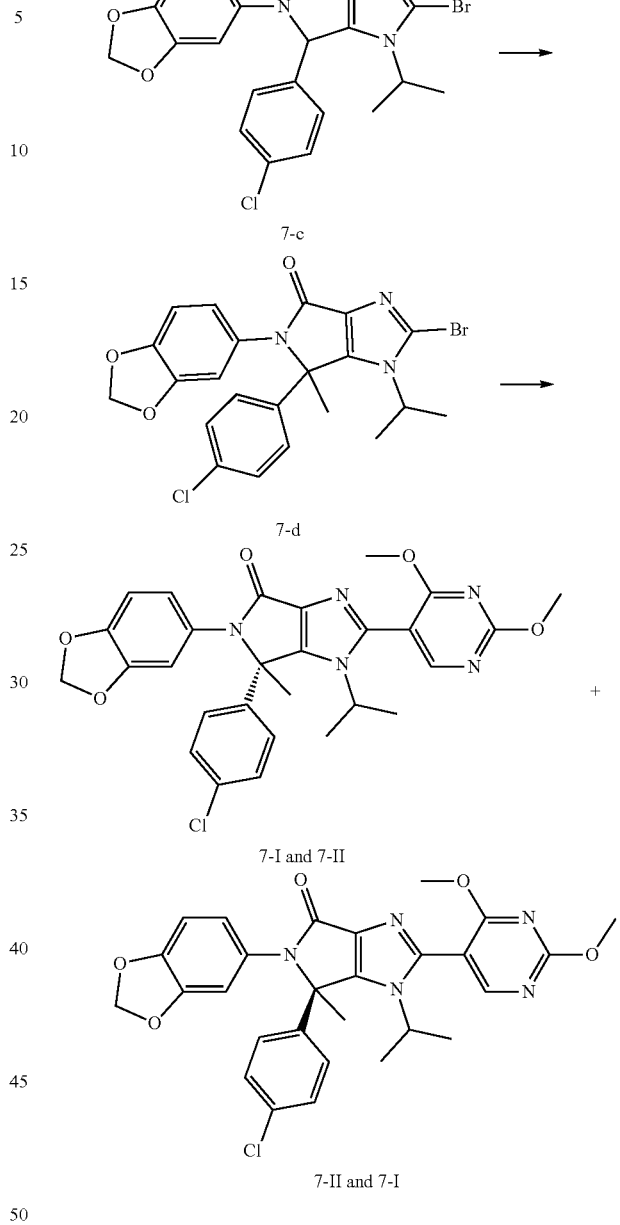

Step A: At room temperature, to a solution of the compound 1-e (10.1 g, 24.04 mmol, 1 eq) and piperonylamine (3.30 g, 24.04 mmol, 1 eq) in MeCN (120 mL) was added DIEA (12.43 g, 96.16 mmol, 16.75 mL, 4 eq), and the reaction solution was heated to 80° C. and stirred for 12 hours. After cooling, an aqueous hydrochloric acid solution (1 M, 50 mL) was added to the reaction solution and concentrated, and the residue was extracted with ethyl acetate (200 mL*2). The organic phases were combined, washed with saturated brine (100 mL*2), dried over Na$_2$SO$_4$, filtered and concentrated. The residue was purified and separated by column chromatography (V/V) SiO$_2$, PE:EA=10:1 to 3:1) to obtain compound 7-a (11 g, yield: 87.86%).

Step B: At room temperature, to a mixed solution of the compound 7-a (15 g, 28.80 mmol, 1 eq) in MeOH (30 mL), H₂O (40 mL) and THF (110 mL) was added NaOH (5.76 g, 144.01 mmol, 5 eq), and stirred for 2 hours at room temperature. The reaction solution was adjusted to pH of about 5 with aqueous HCl solution (1 M, 30 mL), and extracted with ethyl acetate (200 mL*2). The organic phases were combined, washed with saturated brine (100 mL*2), dried over Na₂SO₄, filtered and collected, and the filter cake was dried to obtain compound 7-b (14 g, yield: 98.65%).

Step C: At room temperature, to a solution of the compound 7-b (14 g, 28.41 mmol, 1 eq) in DCM (140 mL) were added T₃P (36.16 g, 56.82 mmol, 33.79 mL, purity: 50%, 2 eq) and pyridine (11.24 g, 142.06 mmol, 11.47 mL, 5 eq), and stirred for 1 hour at 25° C. An aqueous NH₄Cl solution (100 mL) was added to the reaction solution, and extracted with DCM (150 mL*2). The organic phases were combined, washed with saturated brine (100 mL*2), dried over Na₂SO₄, filtered and concentrated. The residue was slurried by (V/V) (EA:PE=1:5, 40 mL) to obtain compound 7-c (12 g, yield: 88.97%).

Step D: At −70° C. under nitrogen protection, to a solution of the compound 7-c (1 g, 2.11 mmol, 1 eq) in THF (15 mL) was slowly added KHMDS (1 M, 4.50 mL, 2.14 eq) solution. After the addition, the reaction solution was stirred at −70° C. for 1 hour, and then CH₃I (3.020 g, 21.28 mmol, 1.32 mL, 10.10 eq) was added thereto, and the reaction solution was stirred for another 1.5 hour. To the reaction solution was added 20 mL of saturated aqueous NH₄Cl (aq.) solution and extracted with ethyl acetate (20 mL*2), and the organic phases were combined, washed with saturated brine (20 mL*1), dried over Na₂SO₄, filtered and concentrated. The residue was purified and separated by column chromatography (V/V) SiO₂, PE:EA=1:0-3:1-1:1) to obtain compound 7-d (450 mg, yield: 42.58%).

Step E: At room temperature under nitrogen protection, to a mixed solution of the compound 7-d (300 mg, 613.80 μmol, 1 eq) and 2,4-dimethoxy-pyrimidine-5-boronic acid (180.00 mg, 978.48 μmol, 1.59 eq) in dioxane (12 mL) and water (4 mL) were added K₃P04 (270.00 mg, 1.27 mmol, 2.07 eq) and Pd(dppf)Cl₂.CH₂Cl₂ (102.00 mg, 124.90 μmol, 2.03e-1 eq) respectively, and the reaction solution was heated to 100° C. and stirred for 12 hours. The reaction solution was cooled and then filtered, and the filtrate was diluted with water (10 mL) and extracted with ethyl acetate (20 mL*2). The organic phases were combined, washed with saturated brine (10 mL*1), dried over Na₂SO₄, filtered and concentrated. The residue was purified and separated by column chromatography (V/V) (SiO2, PE:EA-1:0-3:1-1:1) and preparative HPLC (column: Luna C18 150 mm*25 mm 5 μm; mobile phase: [water (0.225% FA)-ACN]; ACN %: 57%-67%) to obtain compound 7-I (retention time: 0.721 min, 66 mg, yield: 19.09%) and compound 7-II (retention time: 1.291 min, 60 mg, yield: 17.54%).

7-I: ¹H NMR (400 MHz, DMSO-d₆): δ=8.49 (s, 1H), 7.47 (d, J=8.8 Hz, 2H), 7.27 (d, J=8.5 Hz, 2H), 6.82 (d, J=8.3 Hz, 1H), 6.40 (d, J=2.0 Hz, 1H), 6.16 (dd, J=2.0, 8.2 Hz, 1H), 6.02 (d, J=0.9 Hz, 1H), 6.01 (d, J=0.8 Hz, 1H), 4.18-4.06 (m, 1H), 3.99 (s, 3H), 3.93 (s, 3H), 1.97 (s, 3H), 1.16 (d, J=6.8 Hz, 3H), 0.62 (d, J=6.8 Hz, 3H). MS (ESI) m/z: 548.2 (M+H)⁺.

7-II: ¹H NMR (400 MHz, DMSO-d₆): δ=8.49 (s, 1H), 7.47 (d, J=8.8 Hz, 2H), 7.27 (d, J=8.4 Hz, 2H), 6.82 (d, J=8.2 Hz, 1H), 6.40 (d, J=2.0 Hz, 1H), 6.16 (dd, J=2.0, 8.3 Hz, 1H), 6.02 (d, J=0.8 Hz, 1H), 6.01 (s, 1H), 4.18-4.07 (m, 1H), 3.99 (s, 3H), 3.94 (s, 3H), 1.97 (s, 3H), 1.17 (d, J=6.8 Hz, 3H), 0.62 (d, J=6.8 Hz, 3H). MS (ESI) m/z: 548.2 (M+H)⁺.

Example 8

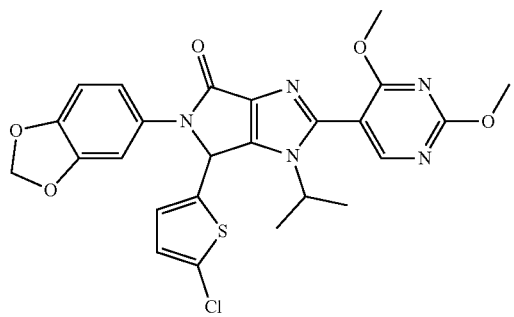

8-I and 8-II 1-e 8-a 8-b 8-c

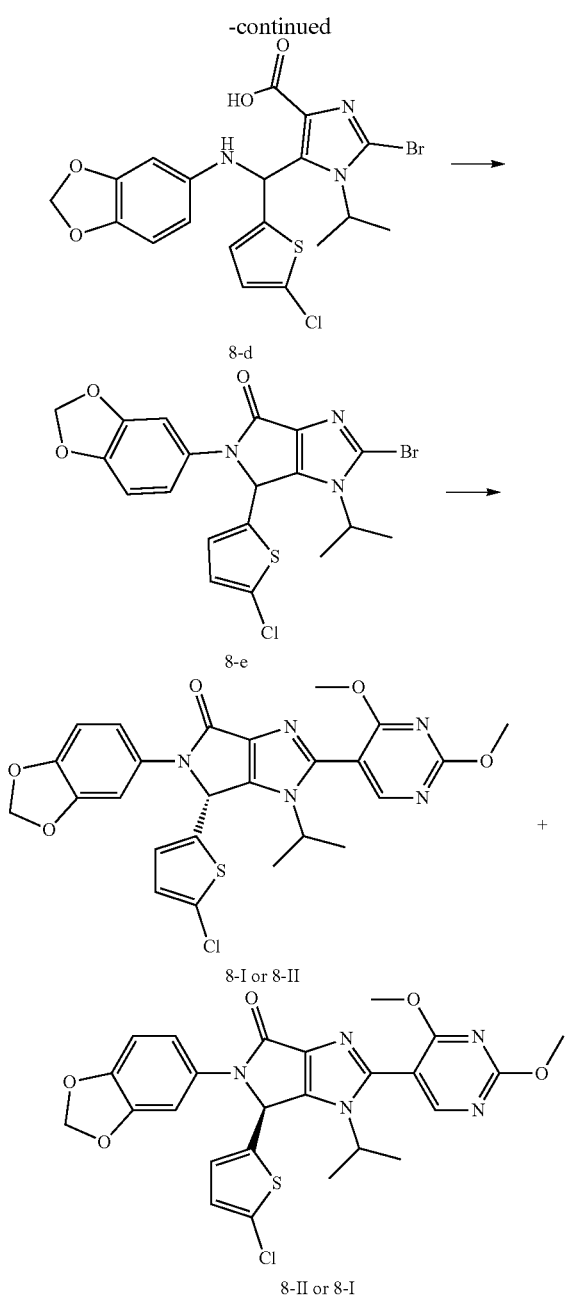

Step A: At −70° C. under nitrogen protection, to a solution of the compound 1-e (50 g, 191.49 mmol, 1 eq) in THF (300 mL) was added dropwise LDA (1 M, 287.23 mL, 1.5 eq), and after the addition, the reaction system was stirred at −70° C. for 0.5 hour. At −70° C. under nitrogen protection, to the reaction solution was added dropwise a solution of 5-chloro-2-thiophenecarboxaldehyde (28.07 g, 191.49 mmol, 20.34 mL, 1 eq) in THF (200 mL), and after the addition, the reaction system was stirred for another 1.5 hours. The reaction solution was quenched with 10% aqueous NH$_4$Cl solution (0.6 L), and extracted with EA (300 mL*3). The organic layers were combined, washed with saturated brine (200 mL), dried over anhydrous Na$_2$SO$_4$, filtered and concentrated to obtain a crude product. The crude product was purified by a silica gel chromatographic column (V/V) (PE:EA=3:1-1:1) to obtain compound 8-a (30 g, yield: 38.43%).

Step B: At 25° C., to a solution of the compound 8-a (30 g, 73.58 mmol, 1 eq) in DCM (200 mL) was added SOCl$_2$ (26.26 g, 220.75 mmol, 16.01 mL, 3 eq), and the reaction solution was stirred for 1 hour at 25° C. The reaction solution was concentrated, and the residue was dissolved in toluene and concentrated to obtain compound 8-b (30 g, the crude product was directly used in the next step).

Step C: At room temperature, to a solution of the compound 8-b (20 g, 46.93 mmol, 1 eq) in acetonitrile (200 mL) were added piperonylamine (6.44 g, 46.93 mmol, 1 eq) and DIPEA (12.13 g, 93.86 mmol, 16.35 mL, 2 eq) respectively, and the reaction solution was heated to 80° C. and stirred for 12 hours. The reaction solution was cooled and then quenched with water (400 mL), and extracted with EA (100 mL*3). The organic layers were combined, washed with saturated brine (100 mL), dried over anhydrous Na$_2$SO$_4$, filtered and concentrated to obtain a crude product. The crude product was purified by a silica gel chromatographic column (V/V) (PE:EA=3:1) to obtain compound 8-c (18 g, yield: 72.8%).

Step D: At room temperature, to a mixed solution of the compound 8-c (16.85 g, 31.98 mmol, 1 eq) in tetrahydrofuran (150 mL), ethanol (100 mL) and water (150 mL) was added LiOH.H$_2$O (2.68 g, 63.96 mmol, 2 eq), and the reaction solution was stirred for 12 hours at 25° C. The reaction solution was concentrated, and the residue was adjusted to pH=4 with HCl (1 M), and extracted with EA (50 mL*3). The organic phases were combined, washed with saturated brine (100 mL), dried over anhydrous Na$_2$SO$_4$, filtered and concentrated to obtain compound 8-d (4 g, yield: 25.08%).

Step E: At room temperature, to a solution of the compound 8-d (4 g, 8.02 mmol, 1 eq) in DMF (40 mL) were added HATU (4.57 g, 12.03 mmol, 1.5 eq) and DIPEA (2.07 g, 16.04 mmol, 2.79 mL, 2 eq) respectively, and the reaction solution was heated to 65° C. and stirred for 2 hours. The reaction system was cooled and then quenched with water (200 mL), a solid was precipitated and filtered, and the filter cake was purified and separated by a silica gel chromatographic column (V/V)(PE:EA=3:1) to obtain compound 8-e (1.8 g, yield: 46.69%).

Step F: At room temperature under nitrogen protection, to a mixed solution of the compound 8-e (0.5 g, 1.04 mmol, 1 eq) and 2,4-dimethoxypyrimidine boronic acid (286.98 mg, 1.56 mmol, 1.5 eq) in dioxane (5 mL) and water (2 mL) were added K$_3$PO$_4$ (662.28 mg, 3.12 mmol, 3 eq) and Pd(dppf)Cl$_2$.CH$_2$Cl$_2$ (67.95 mg, 83.20 μmol, 0.08 eq) respectively, and the reaction system was replaced with nitrogen 3 times, heated to 80° C. and stirred for 12 hours. The reaction system was cooled, then quenched with water (15 mL) and extracted with EA (10 mL*3), and the organic phases were combined, washed with saturated brine (15 mL), dried over anhydrous Na$_2$SO$_4$, filtered and concentrated to obtain a crude product. The crude product was purified and separated by a silica gel chromatographic column (V/V) (PE:EA=1:1) and SFC (column: OD (250 mm*30 mm, 10 μm); mobile phase: [0.1% ammonia water, methanol]; B %: 55%-55%) to obtain compound 8-I (retention time: 1.809 min, 46 mg, yield: 7.89%) and compound 8-II (retention time: 2.286 min, 52 mg, yield: 8.92%).

8-I: $^1$H NMR (400 MHz, CDCl$_3$): δ=8.48 (s, 1H), 7.30 (s, 1H), 6.93 (s, 1H), 6.76-6.71 (m, 3H), 6.02 (s, 1H), 5.97 (s, 2H), 4.24-4.17 (m, 1H), 4.10 (s, 3H), 4.04 (s, 3H), 1.49 (d, J=6.8 Hz, 3H), 0.933 (d, J=6.8 Hz, 3H). MS (ESI) m/z: 540.1 (M+H)$^+$.

8-II: $^1$H NMR (400 MHz, CDCl$_3$): δ=8.48 (s, 1H), 7.30 (s, 1H), 6.93 (s, 1H), 6.76-6.71 (m, 3H), 6.02 (s, 1H), 5.97 (s,

2H), 4.24-4.17 (m, 1H), 4.10 (s, 3H), 4.04 (s, 3H), 1.49 (d, J=6.8 Hz, 3H), 0.933 (d, J=6.8 Hz, 3H). MS (ESI) m/z: 540.1 (M+H)$^+$.

Example 9

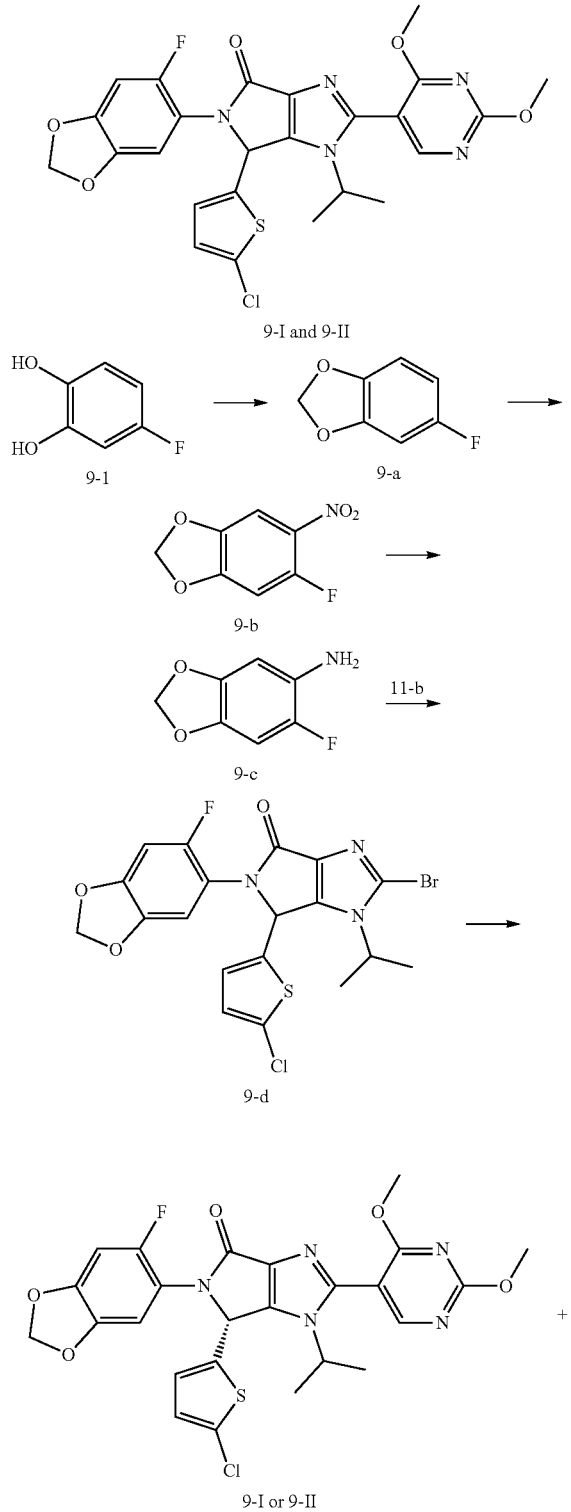

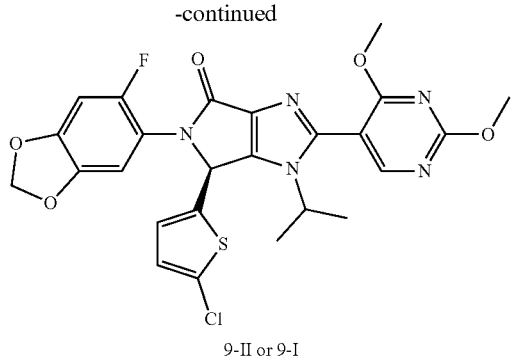

9-II or 9-I

Step A: At room temperature, to a solution of the compound 9-1 (3 g, 23.42 mmol, 1 eq) in DMF (50 mL) were added CH$_2$I$_2$ (9.41 g, 35.13 mmol, 2.83 mL, 1.5 eq) and Cs$_2$CO$_3$ (22.89 g, 70.26 mmol, 3 eq) respectively, and the reaction solution was heated to 100° C. and stirred for 24 hours. The reaction solution was cooled and then quenched with water (50 mL), and extracted with EA (16 mL*3). The organic phases were combined, washed with water (16 mL*3) and saturated brine (16 mL), dried over anhydrous Na$_2$SO$_4$, filtered and concentrated. The residue was purified and separated by column chromatography (V/V) (petroleum ether) to obtain compound 9-a (1.5 g, the crude product was directly used in the next step).

Step B: At −30° C., to the compound 9-a (1.5 g, 10.71 mmol, 1 eq) was added nitric acid (5.78 g, 32.12 mmol, 4.13 mL, purity: 35%, 3 eq). The reaction solution was heated to 20° C. and stirred for 0.5 hour. The reaction solution was poured into water (5 mL), and a solid was precipitated and filtered to obtain compound 9-b as filter cake (1 g, yield: 50.46%).

Step C: At room temperature, to a solution of the compound 9-b (1 g, 5.40 mmol, 1 eq) in HCl (10 mL) was added SnCl$_2$.2H$_2$O (7.31 g, 32.41 mmol, 6 eq), and the reaction solution was stirred for 1 hour at 25° C. The reaction solution was quenched with water (5 mL), and extracted with EA (5 mL*3). The organic phases were combined, washed with saturated brine (5 mL), dried over anhydrous Na$_2$SO$_4$, filtered and concentrated to obtain compound 9-c (0.5 g, yield: 59.66%).

Step D: According to Steps C, D, E and F of Example 11, piperonylamine was replaced with the compound 9-c. The crude product was purified and separated by a silica gel chromatographic column (V/V) (PE:EA=1:2) and SFC (column: OD (250 mm*30 mm, 10 μm); mobile phase: [neutral, MeOH]; MeOH %: 30%-30%) to obtain compound 9-I (retention time: 1.391 min, 46 mg, yield: 25.82%) and compound 9-II (retention time: 1.918 min, 52 mg, yield: 29.19%).

9-I: $^1$H NMR (400 MHz, CDCl$_3$): δ=8.39 (s, 1H), 6.83 (d, J=1.8 Hz, 1H), 6.70-6.65 (m, 2H), 6.56-6.53 (m, 1H), 6.09 (s, 1H), 5.90-5.88 (m, 2H), 4.14-4.10 (m, 1H), 4.01 (s, 3H), 3.95 (s, 3H), 1.39 (d, J=6.8 Hz, 3H), 0.86 (d, J=6.8 Hz, 3H). MS (ESI) m/z: 558.1 (M+H)$^+$.

9-II: $^1$H NMR (400 MHz, CDCl$_3$): δ=8.39 (s, 1H), 6.83 (d, J=1.8 Hz, 1H), 6.70-6.65 (m, 2H), 6.56-6.53 (m, 1H), 6.09 (s, 1H), 5.90-5.88 (m, 2H), 4.14-4.10 (m, 1H), 4.01 (s, 3H), 3.95 (s, 3H), 1.39 (d, J=6.8 Hz, 3H), 0.86 (d, J=6.8 Hz, 3H). MS (ESI) m/z: 558.1 (M+H)$^+$.

Example 10

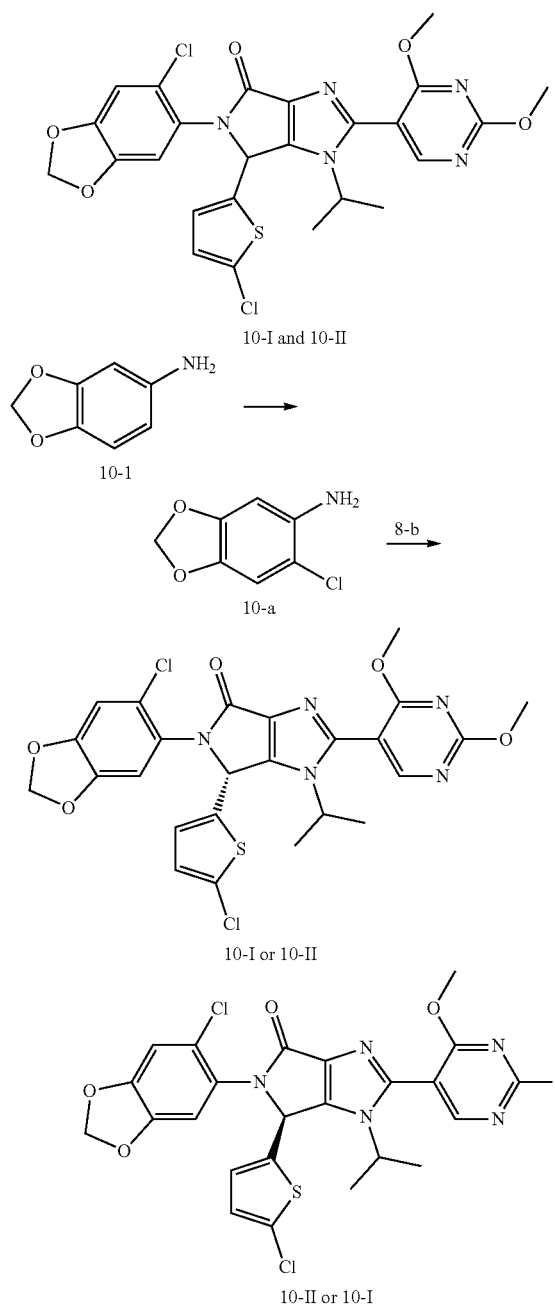

Step A: At room temperature, to a solution of the compound 10-1 (2 g, 14.58 mmol, 59.52 µL, 1 eq) in acetonitrile (20 mL) was added NCS (2.14 g, 16.04 mmol, 1.1 eq), and the reaction solution was stirred for 12 hours at 25° C. The reaction solution was quenched with water (30 mL), and extracted with EA (15 mL*3). The organic phases were combined, washed with HCl (1 N, 15 mL) and saturated brine (16 mL), dried over anhydrous $Na_2SO_4$, filtered and concentrated. The residue was purified and separated by column chromatography (V/V)(petroleum ether/ethyl acetate=10:1) to obtain compound 10-a (1.5 g, yield: 59.94%).

Step B: According to the order of Steps C, D, E and F in Example 11, piperonylamine was replaced with the compound 10-a. The crude product was purified and separated by a silica gel plate (V/V) (PE:EA=1:2) and SFC (column: OD (250 mm*30 mm, 10 µm); mobile phase: [neutral, MeOH]; MeOH %: 40%-40%) to obtain compound 10-I (retention time: 2.740 min, 30 mg, yield: 42.09%) and compound 10-II (retention time: 3.077 min, 33 mg, yield: 46.11%).

10-I: $^1$H NMR (400 MHz, $CDCl_3$): δ=8.40 (s, 1H), 6.81-6.77 (m, 2H), 6.66 (d, J=4 Hz, 1H), 6.53 (s, 1H), 6.18 (s, 1H), 5.92-5.89 (m, 2H), 4.16-4.09 (m, 1H), 4.01 (s, 3H), 3.96 (s, 3H), 1.37 (d, J=6.8 Hz, 3H), 0.88 (d, J=6.8 Hz, 3H). MS (ESI) m/z: 574.1 (M+H)$^+$.

10-II: $^1$H NMR (400 MHz, $CDCl_3$): δ=8.40 (s, 1H), 6.81-6.77 (m, 2H), 6.66 (d, J=4 Hz, 1H), 6.53 (s, 1H), 6.18 (s, 1H), 5.92-5.89 (m, 2H), 4.16-4.09 (m, 1H), 4.01 (s, 3H), 3.96 (s, 3H), 1.37 (d, J=6.8 Hz, 3H), 0.88 (d, J=6.8 Hz, 3H). MS (ESI) m/z: 574.1 (M+H)$^+$.

Example 11

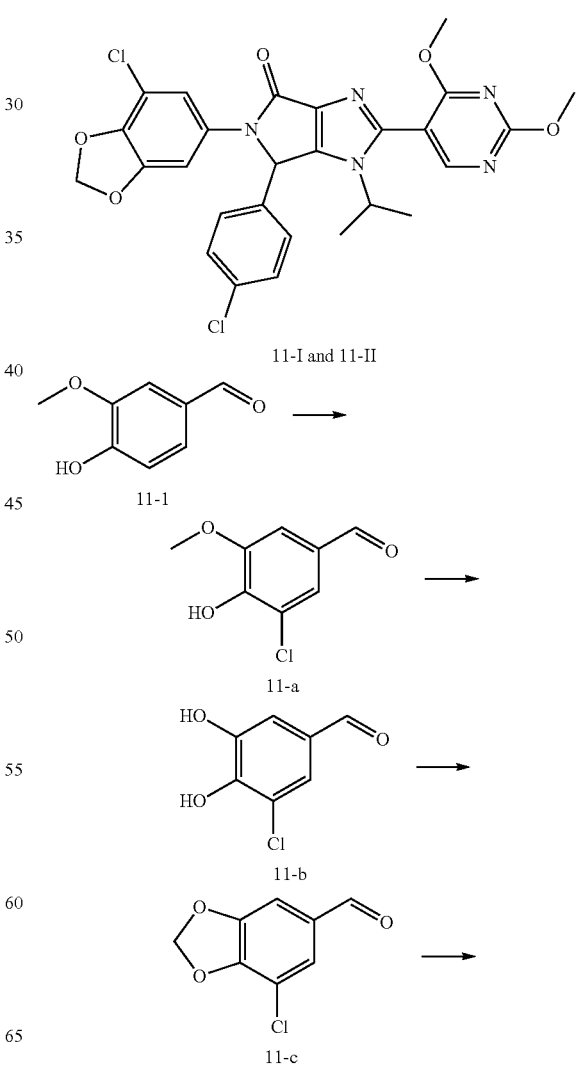

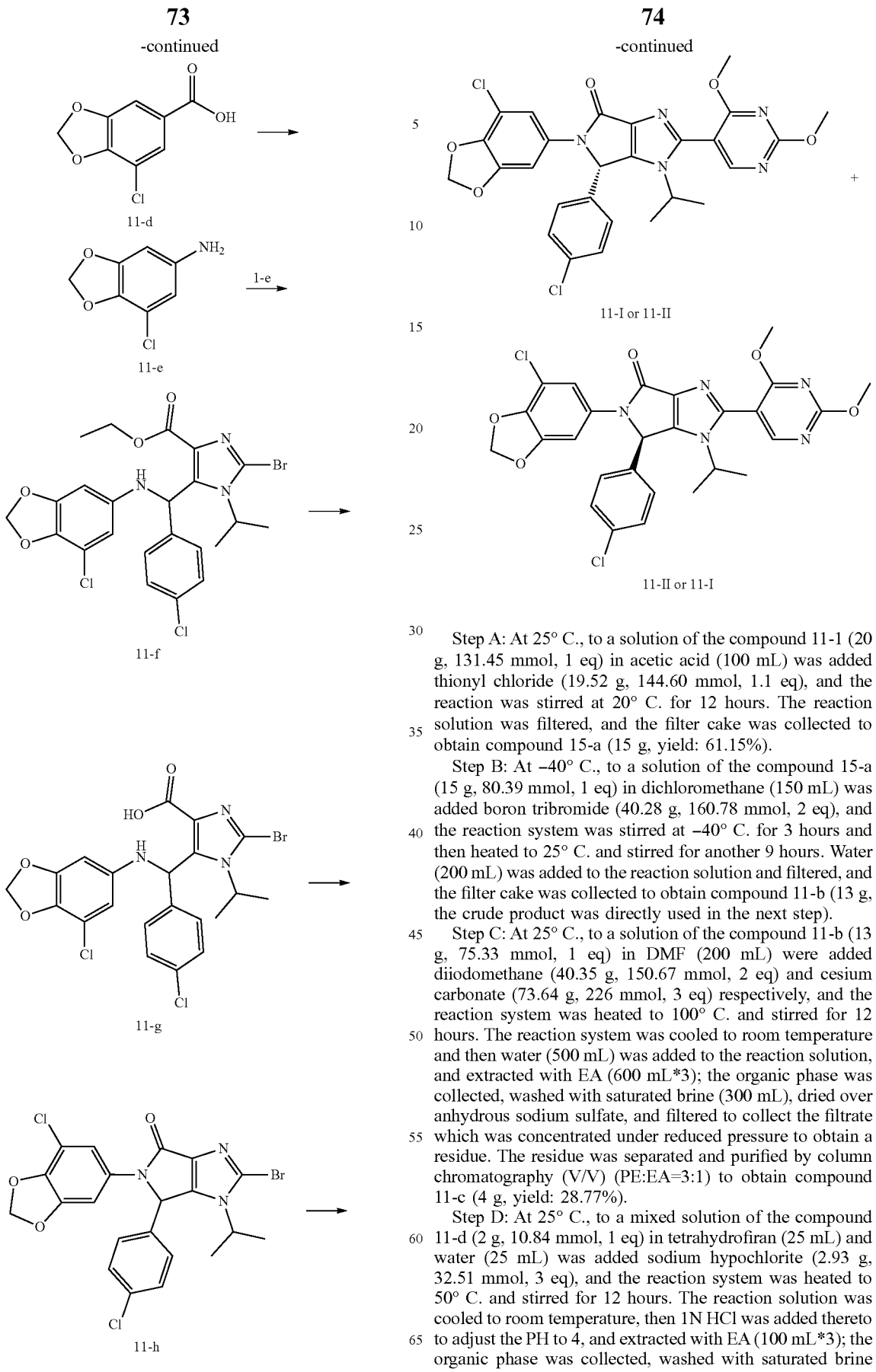

Step A: At 25° C., to a solution of the compound 11-1 (20 g, 131.45 mmol, 1 eq) in acetic acid (100 mL) was added thionyl chloride (19.52 g, 144.60 mmol, 1.1 eq), and the reaction was stirred at 20° C. for 12 hours. The reaction solution was filtered, and the filter cake was collected to obtain compound 15-a (15 g, yield: 61.15%).

Step B: At −40° C., to a solution of the compound 15-a (15 g, 80.39 mmol, 1 eq) in dichloromethane (150 mL) was added boron tribromide (40.28 g, 160.78 mmol, 2 eq), and the reaction system was stirred at −40° C. for 3 hours and then heated to 25° C. and stirred for another 9 hours. Water (200 mL) was added to the reaction solution and filtered, and the filter cake was collected to obtain compound 11-b (13 g, the crude product was directly used in the next step).

Step C: At 25° C., to a solution of the compound 11-b (13 g, 75.33 mmol, 1 eq) in DMF (200 mL) were added diiodomethane (40.35 g, 150.67 mmol, 2 eq) and cesium carbonate (73.64 g, 226 mmol, 3 eq) respectively, and the reaction system was heated to 100° C. and stirred for 12 hours. The reaction system was cooled to room temperature and then water (500 mL) was added to the reaction solution, and extracted with EA (600 mL*3); the organic phase was collected, washed with saturated brine (300 mL), dried over anhydrous sodium sulfate, and filtered to collect the filtrate which was concentrated under reduced pressure to obtain a residue. The residue was separated and purified by column chromatography (V/V) (PE:EA=3:1) to obtain compound 11-c (4 g, yield: 28.77%).

Step D: At 25° C., to a mixed solution of the compound 11-d (2 g, 10.84 mmol, 1 eq) in tetrahydrofuran (25 mL) and water (25 mL) was added sodium hypochlorite (2.93 g, 32.51 mmol, 3 eq), and the reaction system was heated to 50° C. and stirred for 12 hours. The reaction solution was cooled to room temperature, then 1N HCl was added thereto to adjust the PH to 4, and extracted with EA (100 mL*3); the organic phase was collected, washed with saturated brine (120 mL), dried over anhydrous sodium sulfate, and filtered to collect the filtrate which was concentrated under reduced pressure to obtain compound 11-d (1.1 g, yield: 50.61%).

Step E: At 25° C., to a solution of the compound 11-d (1.6 g, 7.98 mmol, 1 eq) in DMF (30 mL) were added Et$_3$N (1.21 g, 11.97 mmol, 1.5 eq) and DPPA (3.29 g, 11.97 mmol, 1.5 eq) respectively, and the reaction system was stirred for 2 hours. Water (150 mL) was added to the reaction solution to quench the reaction, and extracted with EA (150 mL*3); the organic phase was collected, washed with saturated brine (150 mL), dried over anhydrous sodium sulfate, and filtered to collect the filtrate which was concentrated under reduced pressure to obtain a residue. The residue was separated and purified by column chromatography (V/V) (PE:EA=1:1) to obtain compound 11-e (0.4 g, yield: 29.22%).

Step F: At 25° C., to a solution of the compound 11-e (1471.70 mg, 2.75 mmol, 1.1 eq) and compound 1-e (1.05 g, 2.50 mmol, 1 eq) in acetonitrile (15 mL) was added triethylamine (758.69 mg, 7.50 mmol, 3 eq), and the reaction system was heated to 70° C. and stirred for 12 hours. The reaction system was cooled to room temperature, and then water (50 mL) was added to the reaction solution to quench the reaction, and extracted with EA (30 mL*3); the organic phase was collected, washed with saturated brine (150 mL), dried over anhydrous sodium sulfate, filtered and concentrated to obtain compound 11-f (1.6 g, the crude product was directly used in the next step).

Step G: At 20° C., to a mixed solvent of the compound 11-f (1.6 g, 2.88 mmol, 1 eq) in tetrahydrofiran (20 mL), ethanol (10 mL) and water (10 mL) was added LiOH.H2O (483.69 mg, 11.53 mmol, 4 eq), and the reaction system was stirred for 12 hours. 1 N HCl was added to the reaction solution to adjust the PH to 3, and extracted with EA (30 mL*3); the organic phase was collected, washed with saturated brine (50 mL), dried over anhydrous sodium sulfate, and filtered to collect the filtrate which was concentrated under reduced pressure to obtain compound 11-g (1.6 g, the crude product was directly used in the next step).

Step H: At 25° C., to a solution of the compound 11-g (1.60 g, 3.03 mmol, 1 eq) in DMF (30 mL) were added HATU (1.73 g, 4.55 mmol, 1.5 eq) and DIPEA (1.18 g, 9.10 mmol, 3 eq) respectively, and the reaction system was heated to 60° C. and stirred for 10 minutes. The reaction system was cooled to room temperature, and then water (100 mL) was added to the reaction solution to quench the reaction, and extracted with EA (30 mL*3); the organic phase was collected, washed with saturated brine (30 mL), dried over anhydrous sodium sulfate, and filtered to collect the filtrate which was concentrated under reduced pressure to obtain a residue. The residue was separated and purified by column chromatography to obtain compound 11-h (0.5 g, yield: 32.36%).

Step I: At 25° C. under nitrogen atmosphere, to a mixed solution of the compound 11-h (0.5 g, 981.97 mmol, 1 eq) in dioxane (15 mL) and water (5 mL) were added 2,4-dimethoxypyrimidine-5-boronic acid (270.96 mg, 1.47 mmol, 1.5 eq), K$_3$PO$_4$ (625.33 mg, 2.95 mmol, 3 eq) and Pd(dppf)Cl$_2$.CH$_2$Cl$_2$ (80.19 mg, 98.20 μmol, 0.1 eq) respectively, and the reaction system was replaced with nitrogen 3 times, heated to 80° C. and stirred for 12 hours. The reaction system was cooled to room temperature, and then water (50 mL) was added to the reaction solution to quench the reaction, and extracted with EA (30 mL*3); the organic phase was collected, washed with saturated brine (60 mL), dried over anhydrous sodium sulfate, filtered and concentrated to obtain a residue; the residue was separated by column chromatography (V/V) (PE:EA=1:2), purified by HPLC (column: Luna C18 150 mm*25 mm 5 μm; mobile phase: [water (0.225% FA)-ACN]; ACN %: 40%-60%), and resolved by SFC (column: DAICEL CHIRALPAK AD (250 mm*50 mm, 10 μm); mobile phase: [neutral-MeOH]; MeOH %: 50%-50%) to obtain compound 11-I (retention time: 1.947 min, 44 mg, yield: 7.77%) and compound 11-II (retention time: 2.388 min, 37 mg, yield: 6.5%).

11-I: $^1$H NMR (400 MHz, CDCl$_3$): δ=8.46 (s, 1H), 7.37-7.35 (d, J=8, 2H), 7.26-7.22 (d, J=8, 2H), 6.82-6.81 (m, 1H), 6.76-6.75 (m, 1H), 6.01-6.00 (m, 2H), 5.84 (s, 1H), 4.16-4.12 (m, 1H), 4.09 (s, 3H), 4.02 (s, 3H), 1.45-1.44 (m, 3H), 0.65-0.62 (m, 3H). MS (ESI) m/z: 568.1 (M+H)$^+$.

11-II: $^1$H NMR (400 MHz, CDCl$_3$): δ=8.46 (s, 1H), 7.37-7.35 (d, J=8, 2H), 7.26-7.22 (d, J=8, 2H), 6.82-6.81 (m, 1H), 6.76-6.75 (m, 1H), 6.01-6.00 (m, 2H), 5.84 (s, 1H), 4.16-4.12 (m, 1H), 4.09 (s, 3H), 4.02 (s, 3H), 1.45-1.44 (m, 3H), 0.65-0.62 (m, 3H). MS (ESI) m/z: 568.1 (M+H)$^+$.

Example 12

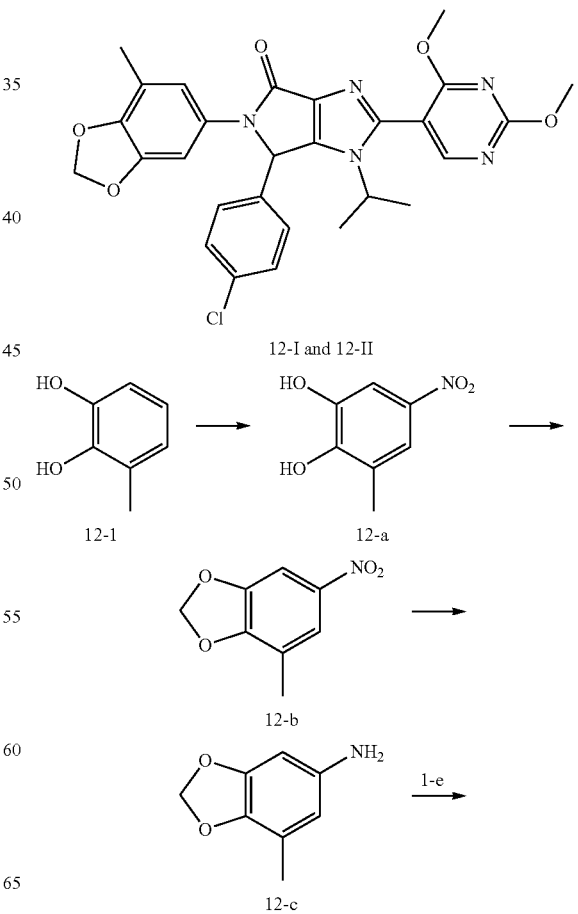

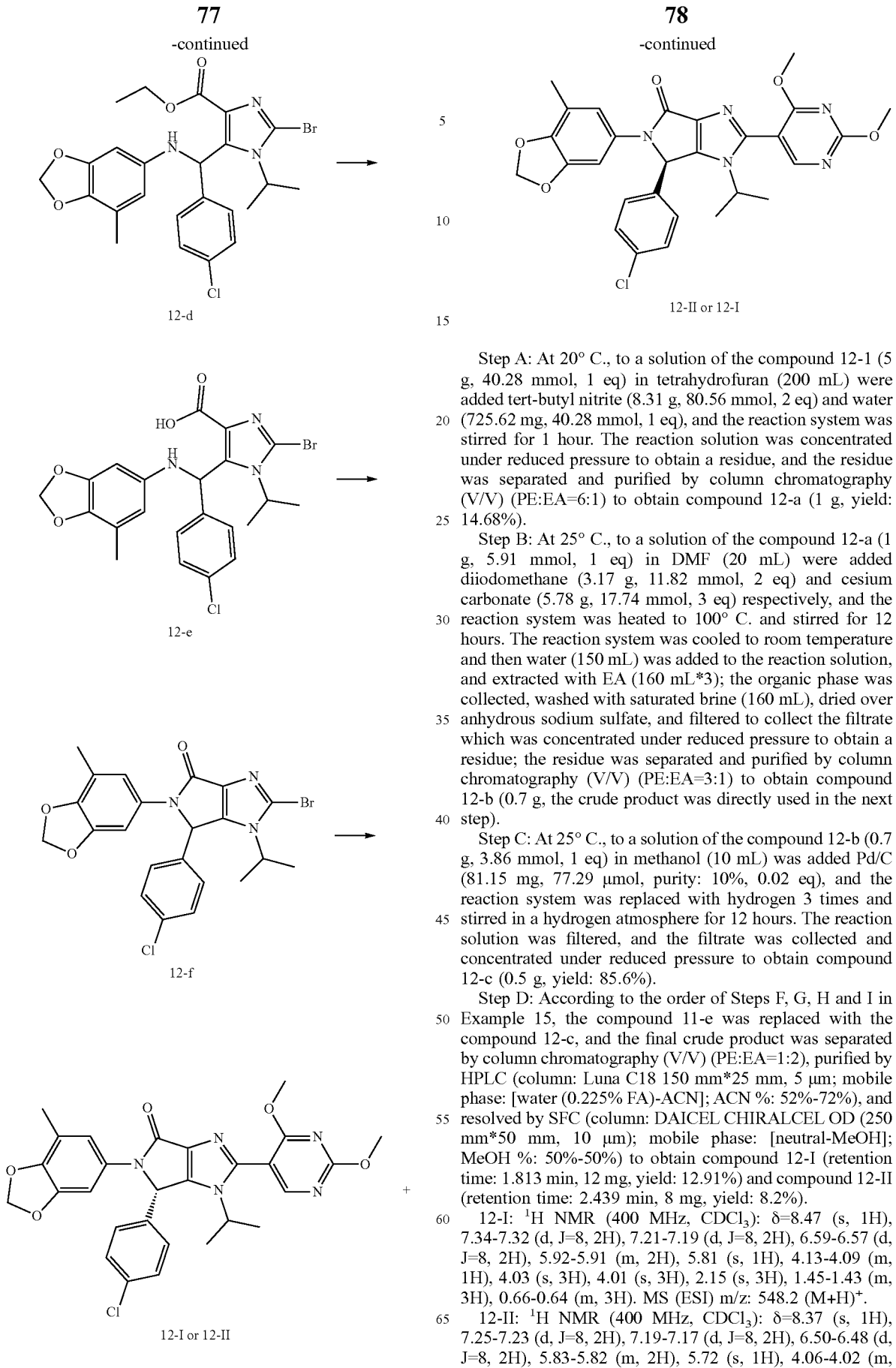

Step A: At 20° C., to a solution of the compound 12-1 (5 g, 40.28 mmol, 1 eq) in tetrahydrofuran (200 mL) were added tert-butyl nitrite (8.31 g, 80.56 mmol, 2 eq) and water (725.62 mg, 40.28 mmol, 1 eq), and the reaction system was stirred for 1 hour. The reaction solution was concentrated under reduced pressure to obtain a residue, and the residue was separated and purified by column chromatography (V/V) (PE:EA=6:1) to obtain compound 12-a (1 g, yield: 14.68%).

Step B: At 25° C., to a solution of the compound 12-a (1 g, 5.91 mmol, 1 eq) in DMF (20 mL) were added diiodomethane (3.17 g, 11.82 mmol, 2 eq) and cesium carbonate (5.78 g, 17.74 mmol, 3 eq) respectively, and the reaction system was heated to 100° C. and stirred for 12 hours. The reaction system was cooled to room temperature and then water (150 mL) was added to the reaction solution, and extracted with EA (160 mL*3); the organic phase was collected, washed with saturated brine (160 mL), dried over anhydrous sodium sulfate, and filtered to collect the filtrate which was concentrated under reduced pressure to obtain a residue; the residue was separated and purified by column chromatography (V/V) (PE:EA=3:1) to obtain compound 12-b (0.7 g, the crude product was directly used in the next step).

Step C: At 25° C., to a solution of the compound 12-b (0.7 g, 3.86 mmol, 1 eq) in methanol (10 mL) was added Pd/C (81.15 mg, 77.29 μmol, purity: 10%, 0.02 eq), and the reaction system was replaced with hydrogen 3 times and stirred in a hydrogen atmosphere for 12 hours. The reaction solution was filtered, and the filtrate was collected and concentrated under reduced pressure to obtain compound 12-c (0.5 g, yield: 85.6%).

Step D: According to the order of Steps F, G, H and I in Example 15, the compound 11-e was replaced with the compound 12-c, and the final crude product was separated by column chromatography (V/V) (PE:EA=1:2), purified by HPLC (column: Luna C18 150 mm*25 mm, 5 μm; mobile phase: [water (0.225% FA)-ACN]; ACN %: 52%-72%), and resolved by SFC (column: DAICEL CHIRALCEL OD (250 mm*50 mm, 10 μm); mobile phase: [neutral-MeOH]; MeOH %: 50%-50%) to obtain compound 12-I (retention time: 1.813 min, 12 mg, yield: 12.91%) and compound 12-II (retention time: 2.439 min, 8 mg, yield: 8.2%).

12-I: $^1$H NMR (400 MHz, CDCl$_3$): δ=8.47 (s, 1H), 7.34-7.32 (d, J=8, 2H), 7.21-7.19 (d, J=8, 2H), 6.59-6.57 (d, J=8, 2H), 5.92-5.91 (m, 2H), 5.81 (s, 1H), 4.13-4.09 (m, 1H), 4.03 (s, 3H), 4.01 (s, 3H), 2.15 (s, 3H), 1.45-1.43 (m, 3H), 0.66-0.64 (m, 3H). MS (ESI) m/z: 548.2 (M+H)$^+$.

12-II: $^1$H NMR (400 MHz, CDCl$_3$): δ=8.37 (s, 1H), 7.25-7.23 (d, J=8, 2H), 7.19-7.17 (d, J=8, 2H), 6.50-6.48 (d, J=8, 2H), 5.83-5.82 (m, 2H), 5.72 (s, 1H), 4.06-4.02 (m,

1H), 4.00 (s, 3H), 3.92 (s, 3H), 2.06 (s, 3H) 1.35-1.34 (m, 3H), 0.56-0.52 (m, 3H). MS (ESI) m/z: 548.2 (M+H)+.

Example 13

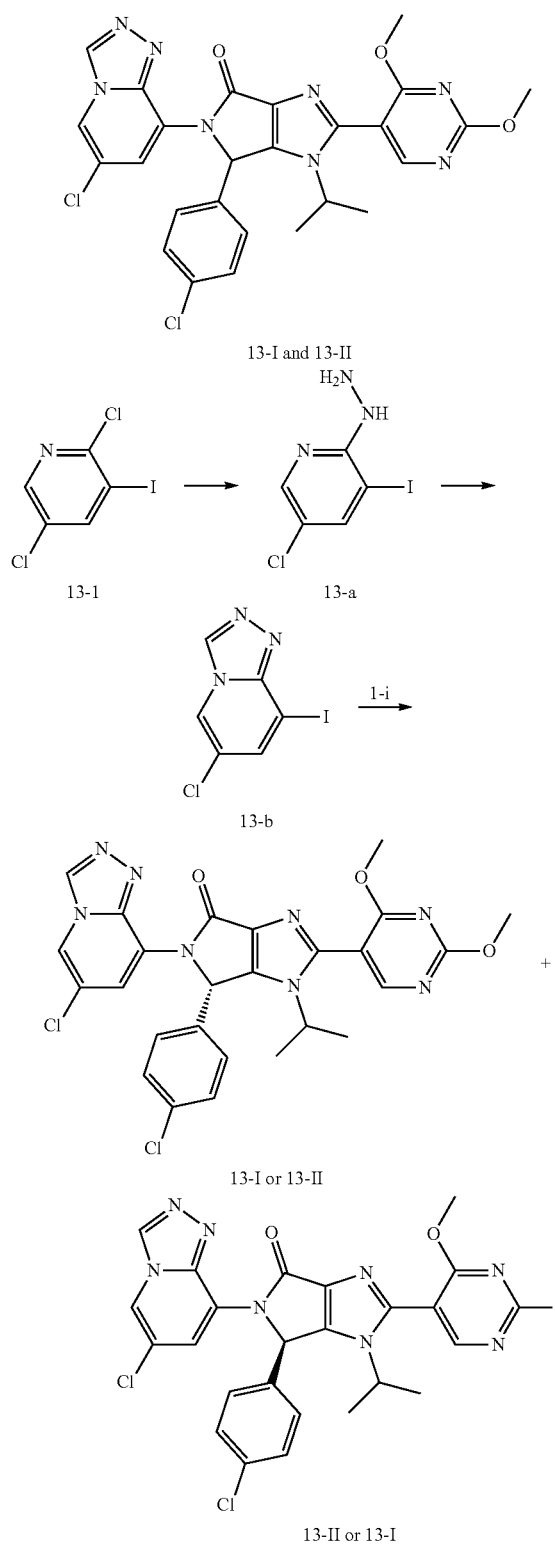

Step A: At 0° C. under nitrogen protection, to a solution of 13-1 (1.00 g, 3.65 mmol, 1.00 eq) in THF (5.00 mL) was added hydrazine hydrate (1.29 g, 21.90 mmol, 1.25 mL, purity: 85%, 6.00 eq). Then the mixture was heated to 70° C. and stirred for 12 hours at this temperature. The mixture was concentrated under reduced pressure to remove THF, and then water (10 ml) was added to the mixture. A white solid was precipitated from the mixture and filtered. The solid was washed with (PE/EA=5:1, 1 mL) to obtain 13-a (0.2 g, yield: 20.33%).

Step B: A mixture of 13-a (200.00 mg, 742.20 μmol, 1.00 eq) and diethoxymethoxyethane (4.00 g, 27.00 mmol, 4.49 mL, 10.00 eq) in acetic acid (2.00 mL) was reacted at 110° C. for 12 hours. The mixture was cooled to 25° C., and then water (20 ml) was added to precipitate a solid and filtered to obtain 13-b (150 mg, yield: 72.32%).

Step C: To a mixture of 1-i (70.00 mg, 157.30 μmol, 1.00 eq) and 13-b (60.00 mg, 214.70 μmol, 1.36 eq) in dioxane (2.50 mL) were added Xantphos (9.10 mg, 15.73 μmol, 0.10 eq) and $Pd_2(dba)_3$ (14.38 mg, 15.73 μmol, 0.10 eq). The mixture was stirred at 90° C. for 10 hours. After cooling, the reaction mixture was filtered and the filtrate was concentrated. The residue was purified by a preparative TLC plate (PE:EA=0:1), and the resulting product was resolved by SFC (column: AS (250 mm*30 mm, 10 μm), 0.1% $NH_3H_2O$ MeOH) to obtain compound 13-I (retention time: 2.269 min, 14 mg, yield: 15.71%) and compound 13-II (retention time: 4.026 min, 13.4 mg, yield: 15.04%).

13-I: $^1$H NMR (400 MHz, CDCl$_3$): δ=8.74 (s, 1H), 8.46 (s, 1H), 7.97 (d, J=1.5 Hz, 1H), 7.76-7.71 (m, 2H), 7.30 (br s, 2H), 7.24-7.18 (m, 2H), 4.14 (quin, J=6.8 Hz, 1H), 4.08 (s, 3H), 4.01 (s, 3H), 1.52 (d, J=6.9 Hz, 3H), 0.62 (d, J=6.8 Hz, 3H). MS (ESI) m/z: 565.1 (M+H)+.

13-II: $^1$H NMR (400 MHz, CDCl$_3$): δ=8.76 (s, 1H), 8.48 (s, 1H), 7.98 (d, J=1.5 Hz, 1H), 7.77-7.73 (m, 2H), 7.35-7.29 (m, 2H), 7.25-7.20 (m, 2H), 4.15 (quin, J=6.8 Hz, 1H), 4.09 (s, 3H), 4.03 (s, 3H), 1.54 (d, J=6.8 Hz, 3H), 0.64 (d, J=6.8 Hz, 3H). MS (ESI) m/z: 565.1 (M+H)+.

Example 14

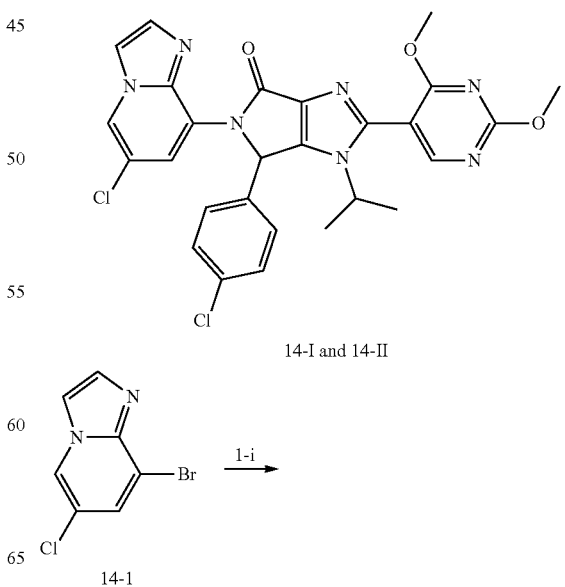

-continued

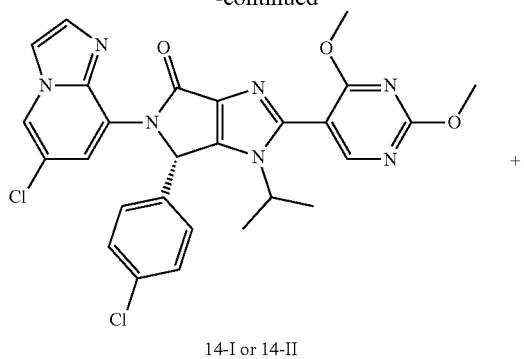

14-I or 14-II

14-II or 14-I

Step A: To a solution of 1-i (400.00 mg, 898.85 μmol, 1.00 eq) and 14-1 (312.10 mg, 1.35 mmol, 1.50 eq) in dioxane (10.00 mL) were added Cs$_2$CO$_3$ (585.73 mg, 1.80 mmol, 2.00 eq), Xantphos (104.02 mg, 179.77 μmol, 0.20 eq) and Pd$_2$(dba)$_3$ (164.62 mg, 179.77 μmol, 0.20 eq). The mixture was stirred at 100° C. for 2 hours under nitrogen protection. The reaction mixture was filtered, and the filtrate was concentrated. The residue was purified by column chromatography (V/V) (PE:EA=1:0-0:1), and then purified by a preparative TLC plate (PE:EA=0:1) to obtain a product which was resolved by SFC (column: OD (250 mm*30 mm, 10 μm), 0.1% NH$_3$H$_2$O MEOH) to obtain compound 14-I (retention time: 2.969 min, 75 mg, yield: 11.99%) and compound 14-II (retention time: 3.223 min, 92 mg, yield: 14.76%).

14-I: (400 MHz, DMSO-d$_6$): δ=8.69 (d, J=1.8 Hz, 1H), 8.51 (s, 1H), 7.96 (d, J=1.0 Hz, 1H), 7.72 (s, 1H), 7.44-7.39 (m, 2H), 7.36-7.25 (m, 4H), 4.23-4.10 (m, 1H), 3.98 (s, 3H), 3.94 (s, 3H), 1.40 (d, J=6.7 Hz, 3H), 0.52 (d, J=6.7 Hz, 3H). MS (ESI) m/z: 564.1 (M+H)$^+$.

14-II: (400 MHz, DMSO-d$_6$): δ=8.69 (d, J=1.6 Hz, 1H), 8.51 (s, 1H), 7.95 (s, 1H), 7.72 (s, 1H), 7.45-7.38 (m, 2H), 7.35-7.26 (m, 4H), 4.23-4.11 (m, 1H), 3.99 (s, 3H), 3.95 (s, 3H), 1.40 (d, J=6.8 Hz, 3H), 0.52 (d, J=6.7 Hz, 3H). MS (ESI) m/z: 564.1 (M+H)$^+$.

Example 15

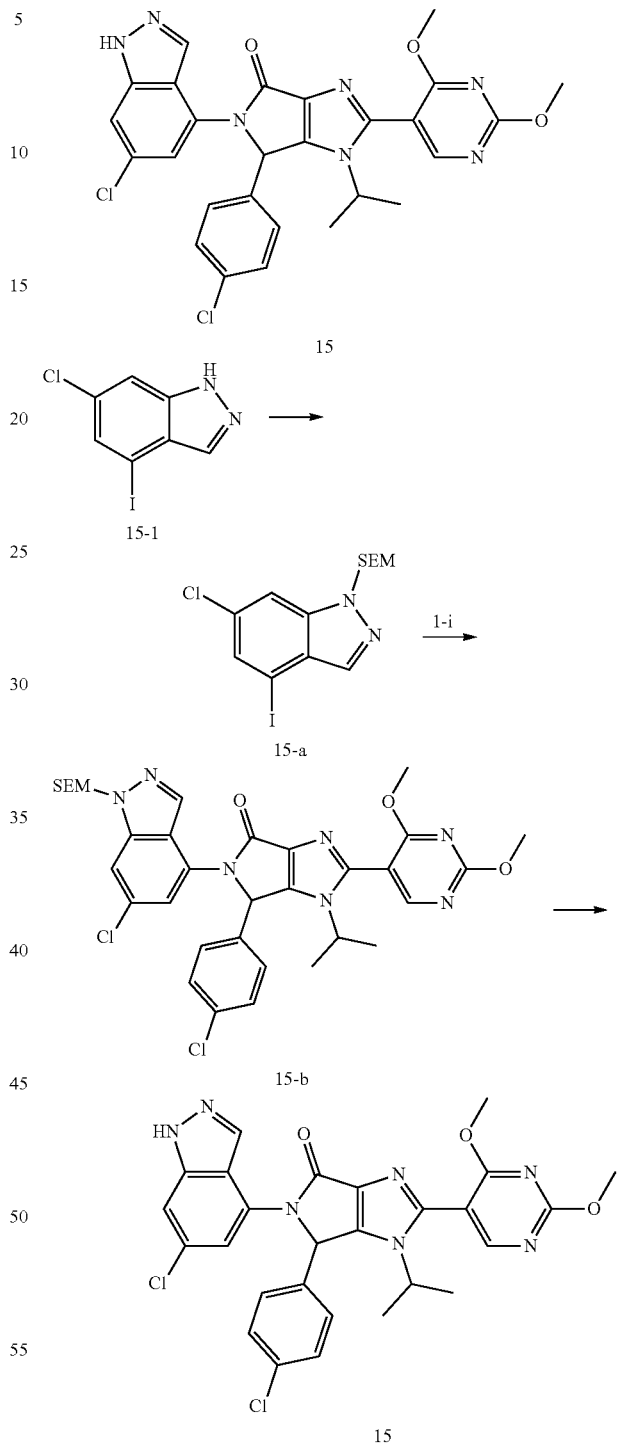

Step A: To a mixture of 15-1 (300.00 mg, 1.08 mmol, 1.00 eq) and K$_2$CO$_3$ (373.17 mg, 2.70 mmol, 2.50 eq) in DMF (3.00 mL) was added SEM-Cl (234.07 mg, 1.40 mmol, 249.01 μL, 1.30 eq). The mixture was stirred at 25° C. for 1 hour. The mixture was quenched with water (6 mL), and extracted with EA (3 mL×3). The combined organic layer was washed with water (2 mL×3), dried over anhydrous Na$_2$SO$_4$, and filtered. The filtrate was concentrated under reduced pressure, and the residue was purified by silica gel chromatography with PE/EA=(10:1-5:1) to obtain 15-a (0.2 g, yield: 45.31%).

Step B: A solution of 1-i (100.00 mg, 118.52 μmol, 1.00 eq), 15-a (118.52 mg, 289.95 μmol, 1.20 eq), Pd$_2$(dba)$_3$ (44.25 mg, 48.33 μmol, 0.20 eq), Xantphos (41.94 mg, 72.49 μmol, 0.30 eq), and Cs$_2$CO$_3$ (118.09 mg, 362.44 μmol, 1.50 eq) in dioxane (1.00 mL) was replaced with nitrogen 3 times. The mixture was stirred at 100° C. for 12 hours under nitrogen protection. The mixture was quenched with water (2 mL), and extracted with EA (2 mL×3). The combined organic layer was washed with brine (5 mL), dried over anhydrous Na$_2$SO$_4$, and filtered. The filtrate was concentrated under reduced pressure. The residue was purified by a preparative TLC plate (EA/PE=2:1) to obtain 15-b (0.1 g, yield: 59.58%).

Step C: To a solution of 15-b (100.00 mg, 143.95 μmol, 1.00 eq) in DCM (1.00 mL) was added trifluoroacetic acid (82.07 mg, 719.75 μmol, 53.29 μL, 5.00 eq), and the mixture was stirred at 25° C. for 2 hours. The mixture was concentrated under reduced pressure, and the residue was purified by a preparative TLC plate (EA) to obtain compound 15 (55 mg, yield: 66.34%).

15: (400 MHz, DMSO-d$_6$): δ=8.61 (s, 1H), 8.57-8.56 (m, 1H), 7.77-7.38 (m, 6H), 6.96-6.95 (m, 2H), 5.69 (s, 1H), 4.24-4.22 (m, 1H), 4.05 (s, 3H), 4.01 (s, 3H), 1.48-1.46 (m, 3H), 0.58-0.56 (m, 3H). MS (ESI) m/z: 564.1 (M+H)$^+$.

Effect Example 1: Determination of Enzyme Level Activity of the Compounds

In the present disclosure, the enzyme level activity the compounds is detected by using the MDM2/p53 protein binding experiment and using a TR-FRET method. The steps were specifically as follows: an Echo pipette (Labcyte) was used to perform a 3.162-fold serial dilution on the test compounds, and each compound was diluted in 11 concentrations and 250 nL for each concentration was transferred to a 384-well plate, with two replicate wells set for each compound concentration. The well with positive compound (100% inhibition) added was set as a positive control, and the well with DMSO only as a negative control. The GST-MDM2 protein (R & D-E3-202-050) was diluted to 0.625 nM with a buffer (125 mM NaCl, 1 mM DTT, 0.01% Gelatin (animal gelatin), 0.1% Pluronic f-127 (polyether), 1 PBS), and 20 μL of the diluent was added to the 384-well plate. After centrifugation and shaking, the 384-well plate was placed in a 23° C. incubator and incubated for 20 min. The His-p53 protein (R & D-SP-450-020) was diluted to 12.5 nM with a buffer, and 20 μL of the diluent was added to the 384-well plate. After centrifugation and shaking, the 384-well plate was placed in a 23° C. incubator and incubated for 60 min. The Eu2+ anti-GST antibody (Cisbio-61GSTKLB) and XL665 anti-His antibody (Cisbio-61HISXLB) were diluted with a buffer, and the diluted mixture contains 0.3 nM Eu2+ anti-GST antibody and 9 nM XL665 anti-His antibody. 10 μL of the mixture of the two antibodies was added to the 384-well plate. After centrifugation and shaking, the 384-well plate was placed in a 23° C. incubator and incubated for 20 h. Reading was performed on an Envision multifunctional microplate reader (PerkinElmer) (excitation light at 340 nm, and emission lights at 665 nm and 615 nm). Ratio=signal intensity at 665 nm/signal intensity at 615 nm×10000 is used to calculate the inhibition ratio, and the formula is as follows: inhibition ratio=(Ratio of the well with compounds added−Ratio of the negative control)/(Ratio of the positive control−Ratio of the negative control)*100%, and the IC$_{50}$ value of each compound is shown in Table 1 below.

Effect Example 2: Determination of Cell Level Activity of the Compounds

Propidium iodide staining was used in SJSA-1 cell proliferation experiment for detection. Propidium iodide cannot pass through the cell membrane of living cells, but can pass through the cell membrane of apoptotic cells to stain the cells. The steps were specifically as follows: the SJSA-1 cells (from the cell bank of WuXi AppTec Biology Department) in the logarithmic growth phase in the cell culture flask were isolated and counted. The SJSA-1 cells were diluted to 1×105 cells/ml with an RPMI1640 cell culture medium supplemented with 10% FBS, 1% double antibody and 1% L-glutamine. 100 μL of PBS was added to the outermost circle of wells of the 384-well plate, 25 μL of the RPMI1640 cell culture medium was added to the second column of wells as a positive control, and 25 μL of the cell suspension was added to other wells (2500 cells/well). After standing at room temperature for 20 min, the cell plate was placed in a cell incubator for overnight culture. The next day, an Echo pipette (Labcyte) was used to perform a 3.162-fold serial dilution on the test compounds, and each compound was diluted in 10 concentrations and 300 nL for each concentration was transferred to a compound plate, with two replicate wells set for each compound concentration. Column 24 without compounds added was used as a negative control. 30 μL of the RPMI1640 cell culture medium was added to all the wells of the compound plate except for the outermost circle of wells, centrifuged and shaken. Then 25 μL of the compound from the compound plate was transferred to the cell plate, respectively. The cell plate was placed in a cell incubator for culture. After 72 h, 10 μL of the 15 μM YO-PRO-1 (Invitrogen-Y3603) dye was added to all the wells of the cell plate except for the outermost circle of wells. Centrifugation and shaking for 20 min at room temperature away from light were performed, and then reading was performed on an Envision multifunctional microplate reader (PerkinElmer) (excitation light at 485 nm, and emission light at 535 nm). Then 20 μL of the cell lysate (150 mM NaCl, 2 mM Tris pH 7.5, 1 mM EDTA, 1 mM EGTA, 1% Triton X-100, ddH$_2$O) was added to all the wells of the cell plate except for the outermost circle of wells. Centrifugation and shaking for 20 min at room temperature away from light were performed, and then reading was performed on an Envision multifunctional microplate reader.

The signal value of the living cells was obtained by using the signal value of the second reading minus the signal value of the first reading, and the inhibition ratio of the drug on tumor cell growth was calculated according to the following formula: inhibition ratio=(signal of the well with compounds added−signal of the negative control)/(signal of the positive control−signal of the negative control)*100%. The anti-proliferative activity (IC$_{50}$ value) of each compound on SJSA-1 cells is shown in Table 1 below:

TABLE 1

Results of in vitro screening tests of compounds of the present disclosure

| Compounds | Target binding ability MDM2 IC$_{50}$ (nM) | Osteosarcoma Cell SJSA-1 Cell IC$_{50}$ (nM) |
|---|---|---|
| 1-I | 0.71 | 150.1 |
| 2 | 1.64 | — |
| 3 | 3.07 | — |
| 4 | 4.57 | — |
| 5 | 1.12 | — |
| 7-II | 0.44 | 156.5 |
| 8-I | 0.79 | — |
| 9I | 0.87 | — |
| 10-I | 0.59 | — |
| 11-I | 0.24 | 98.3 |
| 12-I | 0.69 | 172 |
| 13-I | 2.86 | — |
| 14-II | 0.25 | 154.6 |
| 15 | 1.1 | — |

"—" means the test result has not yet been obtained.

Conclusion: Compounds of the present disclosure show a good activity in binding to the MDM2 protein target and inhibiting the growth of SJSA-1 tumor cells.

Effect Example 3: Pharmacokinetic Studies

1. Abstract

Female Balb/c mice are used as the test animals, the LC/MS/MS method is used to determine drug concentrations in plasma at different times after administering positive reference compound NVP-HDM201 and Examples 1-I and 7-II via tail vein injection and oral cassette dosing in mice. The purposes of the present disclosure are to study the pharmacokinetic behaviors of the compounds of the present disclosure in mice and to evaluate the pharmacokinetic characteristics thereof.

2. Test Scheme 2.1 Experiment Drugs: NVP-HDM201, Compounds of Examples 1-I and 7-II.

2.2 Test Animals

Healthy juvenile female Balb/c mice by weight of 20-30 g, 6 in total.

2.3 Drug Formulation

An appropriate amount of samples were weighed, and then the NVP-HDM201 and compounds of Examples 1-I and 7-II of the present disclosure were formulated with 5% DMSO/40% PEG400/55% water to 0.2 mg/mL of a clear solution for intravenous injection, and formulated with aqueous 0.5% MC solution to 0.2 mg/mL of a suspension for an oral group.

2.4 Administration

There were 6 female Balb/c mice, with after fasting overnight 3 mice administered a dose of 0.5 mg/kg via tail vein injection; the other 3 mice administered orally a dose of 2 mg/kg.

3. Operations

Blood was collected before administration and 0.08, 0.25, 0.5, 1, 2, 4, 8, and 24 hours after administration, placed in a heparinized anticoagulation tube, and centrifuged at 7000 rpm (5204 g) at 4° C., and the plasma was separated and stored at −80° C. 4 hours after administration, the mice were fed.

The LC/MS/MS method was used to determine the content of the compounds to be tested in mouse plasma after iv and oral administration. Plasma samples were analyzed after pretreatment of protein precipitation.

4. Pharmacokinetic Parameters Results

TABLE 2

| Pharmacokinetic parameters | | NVP-HDM201 | Example 1-I | Example 7-II |
|---|---|---|---|---|
| Intravenous injection, 0.5 mpk; Oral administration, 2 mpk | Half-life T$_{1/2}$ (h) | 0.71 | 1.73 | 1.18 |
| | Oral exposure AUC$_{0-t}$ (nM · h) | 1322 | 9626 | 10377 |
| | Oral bioavailability F (%) | 39.6 | 64.4 | 97.4 |

5. Conclusion

Compared with the NVP-HDM201, when the dose of intravenous injection in mice is 0.5 mpk, the compounds of Examples 1-I and 7-II of the present disclosure have a longer half-life in vivo. When the dose of oral administration is 2 mg/kg, the compounds of Examples 1-I and 7-II of the present disclosure have a significantly greater plasma exposure, higher oral bioavailability, and better pharmacokinetic properties.

Effect Example 4: Two-Way Permeability Evaluation Experiment in MDR1-MDCK Cells

Experiment purpose: To determine the permeability of the test compounds in MDR1-MDCK cells Experiment operation: MDR1-MDCK cells that permanently express human P-glycoprotein were inoculated on a 96-well Insert cell plate, and cultured for 4-7 days to form confluent monolayer cells. The test compounds was diluted with an HBSS buffer (pH 7.4) to a concentration of 2 μM, added to the top or basolateral side of the cells, and incubated at 37° C., 5% CO$_2$, 95% relative humidity for 2.5 hours, and then the sample solutions in the donor wells and receiver wells were taken and immediately mixed with a cold acetonitrile solution containing an internal standard. In addition, the cells were lysed with the cold acetonitrile solution containing the internal standard to measure the accumulation amount of intracellular compounds. The LC/MS/MS method was used to analyze the concentrations of the compounds to be tested in all samples (including an initial dosing solution, supernatant of the donor wells, receiver solution, and cell lysate). The concentrations of the test compounds were expressed by the ratio of the peak area thereof to the peak area of the internal standard to detect the permeability of the compounds from directions of A→B and B→A.

| Compounds | Average P$_{app}$ (10$^{-6}$ cm/s) | | Efflux ratio | Average recovery rate % | |
|---|---|---|---|---|---|
| | A→B | B→A | | A→B | B→A |
| NVP-HDM201 | 0.91 | 18.44 | 20.33 | 38.03 | 50.03 |
| Example 7-II | 3.38 | 23.6 | 6.99 | 80.87 | 78.5 |

Experiment conclusion: The compounds of the present disclosure have a good permeability.

Effect Example 5: Two-Way Permeability Evaluation Experiment in Caco-2 Cells

Experiment purpose: To determine the permeability of the test compounds in Caco-2 cells Experiment operation: Human colon cancer Caco-2 cells were inoculated on a 96-well Insert cell plate at a density of $1\times10^5$ cells/cm², and cultured for 4-5 days to form confluent monolayer cells. The test compounds was diluted with an HBSS buffer (pH 7.4) to a concentration of 2 μM, added to the top or basolateral side of the cells, and incubated at 37° C., 5% $CO_2$ and saturated humidity for 2.5 hours, and then the sample solutions in the donor wells and receiver wells were taken and immediately mixed with a cold acetonitrile solution containing an internal standard. In addition, the cells were lysed with the cold acetonitrile solution containing the internal standard to measure the accumulation amount of intracellular compounds. The LC/MS/MS method was used to analyze the concentrations of the compounds to be tested in all samples (including an initial dosing solution, supernatant of the donor wells, receiver solution, and cell lysate). The concentrations of the test compounds were expressed by the ratio of the peak area thereof to the peak area of the internal standard to detect the permeability of the compounds from directions of A→B and B→A.

| Compounds | Average $P_{app}$ ($10^{-6}$ cm/s) | | Efflux ratio | Average recovery rate % | |
|---|---|---|---|---|---|
| | A→B | B→A | | A→B | B→A |
| NVP-HDM201 | 0.17 | 34.28 | 198.18 | 94.29 | 88.31 |
| Example 7-II | 1.15 | 43.41 | 37.82 | 73.22 | 85.58 |

Experiment conclusion: The compounds of the present disclosure have a good permeability.

Effect Example 6: Evaluation for Efficacy of the Compounds in Animals with Acute Myeloid Leukemia 0.2 mL (10×106 cells, containing 50% Matrigel) of MV4-11 tumor cells were inoculated subcutaneously on the right back of each mouse to form a transplanted tumor; when the volume reached 100-200 mm³, the animals were randomly grouped according to the tumor volume, with 8 in the negative control group, 8 in the positive control group, and 8 in the experimental group. The experimental group was orally administered with different doses of positive drug NVP-HDM201 (6 mg/kg) and Example 7-II (6 mg/kg and 12 mg/kg) once a day by gavage, and the negative control group was given the same amount of solvent at the same time. The length (A) and width (B) of the tumor were measured with a vernier caliper twice a week, thereby calculating the tumor volume V=A×B²/2. The calculation of relative tumor volume (RTV) follows: RTV=$V_t/V_0$, where $V_t$ is the tumor volume at the end of the administration, and $V_0$ is the tumor volume measured before division into different cages for administration. The pharmacodynamic evaluation index of the anti-tumor activity is the relative tumor proliferation ratio T/C (%), and the calculation formula is: T/C (%)=$T_{RTV}/C_{RTV}\times100\%$. Where $T_{RTV}$ is the RTV of the treatment group; $C_{RTV}$ is the RTV of the negative control group. Efficacy evaluation criteria: T/C %>60% is invalid; T/C %≤60% and P<0.05 upon statistical treatment is valid. The calculation formula of the tumor growth inhibition ratio (TGI) is as follows:

TGI (%)={[($CV_t-CV_0$)−($TV_t-TV_0$)]/($CV_t-CV0$)}×100%

$CV_t$ is the tumor volume of the control group at the end of the administration; $CV_0$ is the tumor volume of the control group before division into different cages for administration; $TV_t$ is the tumor volume of the dosing group at the end of the administration; $TV_0$ is the tumor volume of the dosing group before division into different cages for administration. The difference in tumor volumes between the dosing group and the control group was subjected to t-test. At the same time, the nude mice of each group were weighed twice a week to preliminarily evaluate the side effects of the drugs. The efficacy results of each compound in this model are shown in Table 3 below.

TABLE 3

In vivo efficacy test results of the compounds of the present disclosure

| Groups | Tumor volume (mm³) (Day 0) | Tumor volume (mm³)$^a$ (Day 21) | RTV (21 days) | T/C (%) | TGI (%) |
|---|---|---|---|---|---|
| Blank control | 153 ± 19 | 1012 ± 206 | 6.36 ± 1.00 | — | — |
| NVP-HDM201 (6 mg/kg) | 153 ± 20 | 695 ± 115 | 4.68 ± 0.69 | 73.58 | 36.91 |
| Example 7-II (6 mg/kg) | 153 ± 18 | 582 ± 72 | 4.00 ± 0.44 | 62.89 | 50.05 |
| Example 7-II (12 mg/kg) | 153 ± 17 | 445 ± 69 | 2.92 ± 0.41 | 45.96 | 65.94 |

Conclusion: The compounds of the present disclosure have a better anti-tumor effect in a model of mice transplanted with MV4-11 human acute myeloid leukemia, and show a good dose-effect relationship.

What is claimed is:
1. A compound represented by formula (I-1):

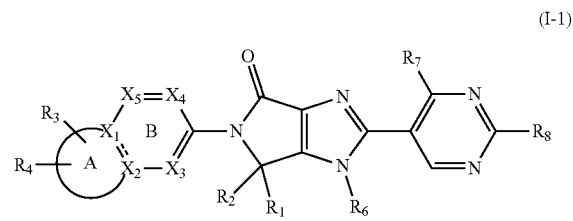

(I-1)

or a pharmaceutically acceptable salt or stereoisomer thereof,
wherein:

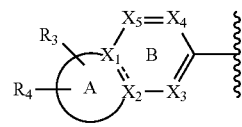

is:

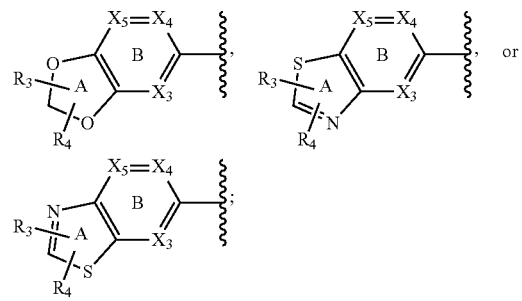

$X_3$ is CH or $CR_{10}$;

$X_4$ is CH or $CR_{11}$;

$X_5$ is CH or $CR_{12}$;

$R_1$ is H or $C_{1-3}$ alkyl, wherein the $C_{1-3}$ alkyl is optionally substituted with 1, 2, or 3 independently selected $R_a$ substituents;

$R_2$ is phenyl, wherein the phenyl is optionally substituted with 1, 2, or 3 independently selected $R_e$ substituents;

$R_3$ is H, halogen, CN, $C_{1-3}$ alkyl, $C_{1-3}$ heteroalkyl, $NH_2$, or OH, wherein the $C_{1-3}$ heteroalkyl comprises 1, 2, or 3 heteroatoms or heteroatomic groups independently selected from the group consisting of —C(O)—, —C(O)O—, —C(S)—, N, —NH—, —O—, —S—, —S(O)—, and —S(O)$_2$—, and further wherein the $C_{1-3}$ alkyl or $C_{1-3}$ heteroalkyl is optionally substituted with 1, 2, or 3 independently selected $R_c$ substituents;

$R_4$ is H, halogen, CN, $C_{1-3}$ alkyl, $C_{1-3}$ heteroalkyl, $NH_2$, or OH, wherein the $C_{1-3}$ heteroalkyl comprises 1, 2, or 3 heteroatoms or heteroatomic groups independently selected from the group consisting of —C(O)—, —C(O)O—, —C(S)—, N, —NH—, —O—, —S—, —S(O)—, and —S(O)$_2$—, and further wherein the $C_{1-3}$ alkyl or $C_{1-3}$ heteroalkyl is optionally substituted with 1, 2, or 3 independently selected $R_c$ substituents;

$R_6$ is $CH(CH_3)_2$;

$R_7$ is $OC_{1-3}$ alkyl, wherein the $OC_{1-3}$ alkyl is optionally substituted with 1, 2, or 3 independently selected halogen substituents;

$R_8$ is $OC_{1-3}$ alkyl, wherein the $OC_{1-3}$ alkyl is optionally substituted with 1, 2, or 3 independently selected halogen substituents;

$R_{10}$ is halogen, CN, $C_{1-3}$ alkyl, $C_{1-3}$ heteroalkyl, $NH_2$, or OH, wherein the $C_{1-3}$ heteroalkyl comprises 1, 2, or 3 heteroatoms or heteroatomic groups independently selected from the group consisting of —C(O)—, —C(O)O—, —C(S)—, N, —NH—, —O—, —S—, —S(O)—, and —S(O)$_2$—, and further wherein the $C_{1-3}$ alkyl or $C_{1-3}$ heteroalkyl is optionally substituted with 1, 2, or 3 independently selected $R_d$ substituents;

$R_{11}$ is halogen, CN, $C_{1-3}$ alkyl, $C_{1-3}$ heteroalkyl, $NH_2$, or OH, wherein the $C_{1-3}$ heteroalkyl comprises 1, 2, or 3 heteroatoms or heteroatomic groups independently selected from the group consisting of —C(O)—, —C(O)O—, —C(S)—, N, —NH—, —O—, —S—, —S(O)—, and —S(O)$_2$—, and further wherein the $C_{1-3}$ alkyl or $C_{1-3}$ heteroalkyl is optionally substituted with 1, 2, or 3 independently selected $R_d$ substituents;

$R_{12}$ is halogen, CN, $C_{1-3}$ alkyl, $C_{1-3}$ heteroalkyl, $NH_2$, or OH, wherein the $C_{1-3}$ heteroalkyl comprises 1, 2, or 3 heteroatoms or heteroatomic groups independently selected from the group consisting of —C(O)—, —C(O)O—, —C(S)—, N, —NH—, —O—, —S—, —S(O)—, and —S(O)$_2$—, and further wherein the $C_{1-3}$ alkyl or $C_{1-3}$ heteroalkyl is optionally substituted with 1, 2, or 3 independently selected $R_d$ substituents;

each $R_a$ is independently halogen, CN, $C_{1-3}$ alkyl, $C_{1-3}$ heteroalkyl, $NH_2$, OH, or $C_{3-5}$ cycloalkyl, wherein each $C_{1-3}$ heteroalkyl independently comprises 1, 2, or 3 heteroatoms or heteroatomic groups independently selected from the group consisting of —C(O)—, —C(O)O—, —C(S)—, N, —NH—, —O—, —S—, —S(O)—, and —S(O)$_2$—, and further wherein each $C_{1-3}$ alkyl, $C_{1-3}$ heteroalkyl, or $C_{3-5}$ cycloalkyl is optionally and independently substituted with 1, 2, or 3 independently selected R substituents;

each $R_b$ is independently halogen, CN, $C_{1-3}$ alkyl, $C_{1-3}$ heteroalkyl, $NH_2$, OH, or $C_{3-5}$ cycloalkyl, wherein each $C_{1-3}$ heteroalkyl independently comprises 1, 2, or 3 heteroatoms or heteroatomic groups independently selected from the group consisting of —C(O)—, —C(O)O—, —C(S)—, N, —NH—, —O—, —S—, —S(O)—, and —S(O)$_2$—, and further wherein each $C_{1-3}$ alkyl, $C_{1-3}$ heteroalkyl, or $C_{3-5}$ cycloalkyl is optionally and independently substituted with 1, 2, or 3 independently selected R substituents;

each $R_c$ is independently halogen, CN, $C_{1-3}$ alkyl, $C_{1-3}$ heteroalkyl, $NH_2$, OH, or $C_{3-5}$ cycloalkyl, wherein each $C_{1-3}$ heteroalkyl independently comprises 1, 2, or 3 heteroatoms or heteroatomic groups independently selected from the group consisting of —C(O)—, —C(O)O—, —C(S)—, N, —NH—, —O—, —S—, —S(O)—, and —S(O)$_2$—, and further wherein each $C_{1-3}$ alkyl, $C_{1-3}$ heteroalkyl, or $C_{3-5}$ cycloalkyl is optionally and independently substituted with 1, 2, or 3 independently selected R substituents;

each $R_d$ is independently halogen, CN, $C_{1-3}$ alkyl, $C_{1-3}$ heteroalkyl, $NH_2$, OH, or $C_{3-5}$ cycloalkyl, wherein each $C_{1-3}$ heteroalkyl independently comprises 1, 2, or 3 heteroatoms or heteroatomic groups independently selected from the group consisting of —C(O)—, —C(O)O—, —C(S)—, N, —NH—, —O—, —S—, —S(O)—, and —S(O)$_2$—, and further wherein each $C_{1-3}$ alkyl, $C_{1-3}$ heteroalkyl, or $C_{3-5}$ cycloalkyl is optionally and independently substituted with 1, 2, or 3 independently selected R substituents; and each R is independently F, Cl, Br, I, CN, $CH_3$, $CH_2F$, $CHF_2$, $CF_3$, $CH_2CH_3$, $CH_2CH_2CH_3$, $CH(CH_3)_2$, $NH_2$, $NO_2$, OH, or $OCH_3$.

2. The compound as defined in claim 1, or a pharmaceutically acceptable salt or stereoisomer thereof, wherein

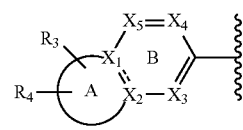

is:

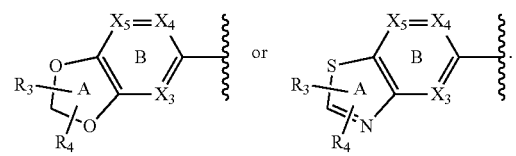

3. The compound as defined in claim 2, or a pharmaceutically acceptable salt or stereoisomer thereof, wherein

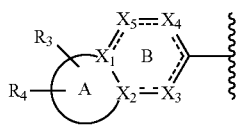

is:

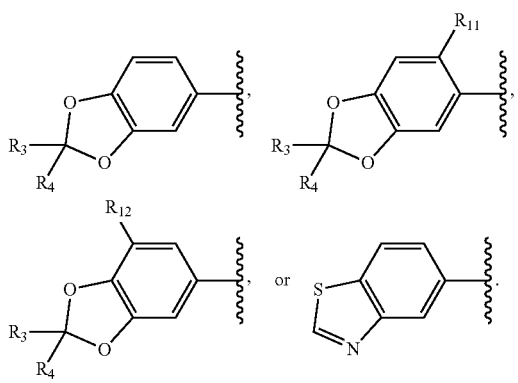

4. The compound as defined in claim 3, or a pharmaceutically acceptable salt or stereoisomer thereof, wherein

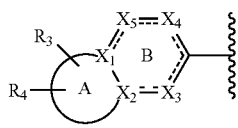

is:

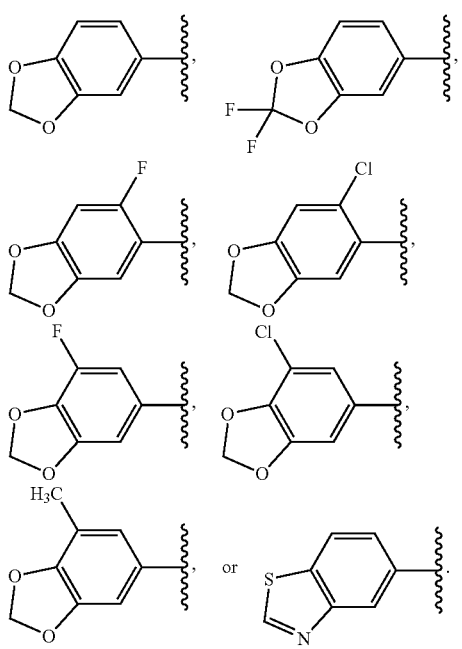

5. The compound as defined in claim 1, wherein the compound is of formula (I-3):

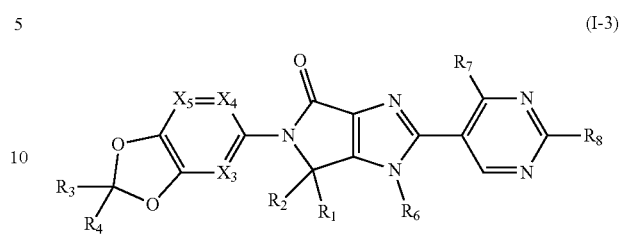

(I-3)

or a pharmaceutically acceptable salt or stereoisomer thereof.

6. The compound as defined in claim 1, or a pharmaceutically acceptable salt or stereoisomer thereof, wherein:
   (i) $R_1$ is H, $CH_3$, $CH_2CH_3$, or $CH(CH_3)_2$; or
   (ii) $R_2$ is phenyl, wherein the phenyl is optionally substituted with 1 or 2 independently selected $R_e$ substituents; or
   (iii) each $R_a$ is independently F, Cl, Br, I, CN, $CH_3$, $CH_2F$, $CHF_2$, $CF_3$, $CH_2CH_3$, $NH_2$, OH, $OCH_3$, or cyclopropyl;
   each $R_b$ is independently F, Cl, Br, I, CN, $CH_3$, $CH_2F$, $CHF_2$, $CF_3$, $CH_2CH_3$, $NH_2$, OH, $OCH_3$, or cyclopropyl;
   each $R_c$ is independently F, Cl, Br, I, CN, $CH_3$, $CH_2F$, $CHF_2$, $CF_3$, $CH_2CH_3$, $NH_2$, OH, $OCH_3$, or cyclopropyl; and
   each $R_d$ is independently F, Cl, Br, I, CN, $CH_3$, $CH_2F$, $CHF_2$, $CF_3$, $CH_2CH_3$, $NH_2$, OH, $OCH_3$, or cyclopropyl.

7. The compound as defined in claim 6, or a pharmaceutically acceptable salt or stereoisomer thereof, wherein $R_2$ is phenyl, 4-chlorophenyl, or 4-cyclopropylphenyl.

8. The compound as defined in claim 1, or a pharmaceutically acceptable salt or stereoisomer thereof, wherein:
   $R_3$ is H, F, Cl, Br, I, CN, $CH_3$, $CH_2CH_3$, OH, or $OCH_3$, wherein the $CH_3$, $CH_2CH_3$, or $OCH_3$ is optionally substituted with 1, 2, or 3 independently selected $R_c$ substituents; and
   $R_4$ is H, F, Cl, Br, I, CN, $CH_3$, $CH_2CH_3$, OH, or $OCH_3$, wherein the $CH_3$, $CH_2CH_3$, or $OCH_3$ is optionally substituted with 1, 2, or 3 independently selected $R_c$ substituents.

9. The compound as defined in claim 8, or a pharmaceutically acceptable salt or stereoisomer thereof, wherein:
   $R_3$ is H, F, Cl, Br, I, CN, $CH_3$, $CH_2CH_3$, $CH_2CF_3$, $CH(CH_3)_2$, OH, or $OCH_3$; and
   $R_4$ is H, F, Cl, Br, I, CN, $CH_3$, $CH_2CH_3$, $CH_2CF_3$, $CH(CH_3)_2$, OH, or $OCH_3$.

10. The compound as defined in claim 1, or a pharmaceutically acceptable salt or stereoisomer thereof, wherein:
    $R_7$ is $OCH_3$, $OCH_2F$, $OCHF_2$, $OCF_3$, $OCH_2CH_3$, $OCH_2CH_2CH_3$, or $OCH(CH_3)_2$; and
    $R_8$ is $OCH_3$, $OCH_2F$, $OCHF_2$, $OCF_3$, $OCH_2CH_3$, $OCH_2CH_2CH_3$, or $OCH(CH_3)_2$.

11. The compound as defined in claim 1, or a pharmaceutically acceptable salt or stereoisomer thereof, wherein:
    $R_{10}$ is F, Cl, Br, I, CN, $CH_3$, $CH_2CH_3$, OH, or $OCH_3$, wherein the $CH_3$, $CH_2CH_3$, or $OCH_3$ is optionally substituted with 1, 2, or 3 independently selected $R_d$ substituents;

$R_{11}$ is F, Cl, Br, I, CN, $CH_3$, $CH_2CH_3$, OH, or $OCH_3$, wherein the $CH_3$, $CH_2CH_3$, or $OCH_3$ is optionally substituted with 1, 2, or 3 independently selected $R_d$ substituents; and $R_{12}$ is F, Cl, Br, I, CN, $CH_3$, $CH_2CH_3$, OH, or $OCH_3$, wherein the $CH_3$, $CH_2CH_3$, or $OCH_3$ is optionally substituted with 1, 2, or 3 independently selected $R_d$ substituents.

12. The compound as defined in claim 11, or a pharmaceutically acceptable salt or stereoisomer thereof, wherein:

$R_{10}$ is F, Cl, Br, I, CN, $CH_3$, $CH_2CH_3$, $CH_2CF_3$, $CH(CH_3)_2$, OH, or $OCH_3$;

$R_{11}$ is F, Cl, Br, I, CN, $CH_3$, $CH_2CH_3$, $CH_2CF_3$, $CH(CH_3)_2$, OH, or $OCH_3$; and $R_{12}$ is F, Cl, Br, I, CN, $CH_3$, $CH_2CH_3$, $CH_2CF_3$, $CH(CH_3)_2$, OH, or $OCH_3$.

13. The compound as defined in claim 1, or a pharmaceutically acceptable salt or stereoisomer thereof, wherein

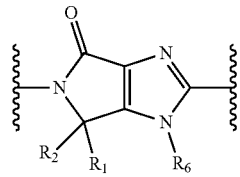

is:

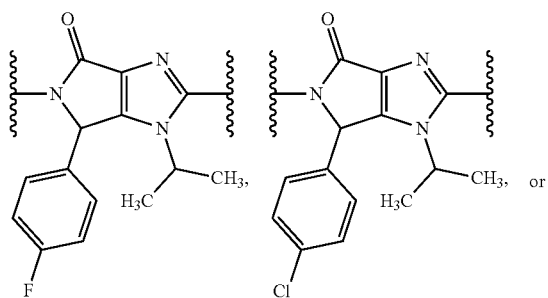

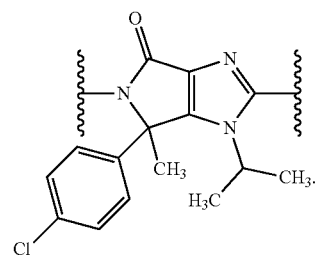

14. The compound as defined in claim 1, wherein the compound is selected from the group consisting of:

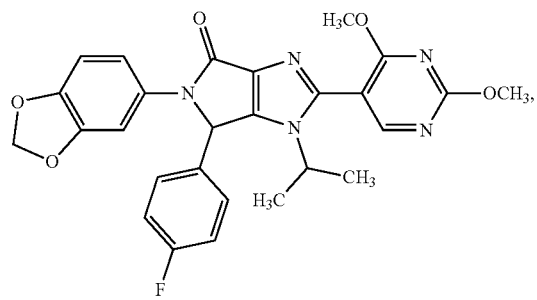 [SMILES: COc1ncc(-c2nc3c(n2C(C)C)C(c2ccc(Cl)cc2)N(c2ccc4ncsc4c2)C3=O)c(OC)n1]

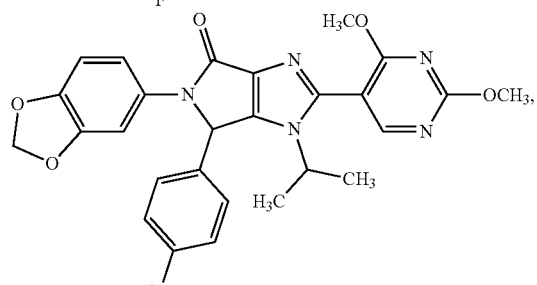

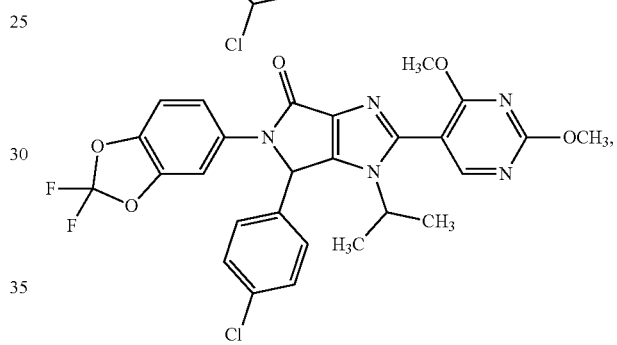

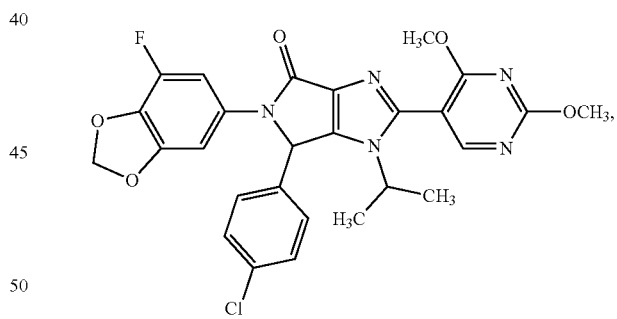

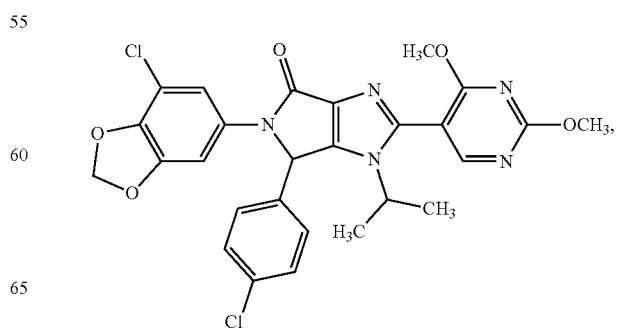

-continued
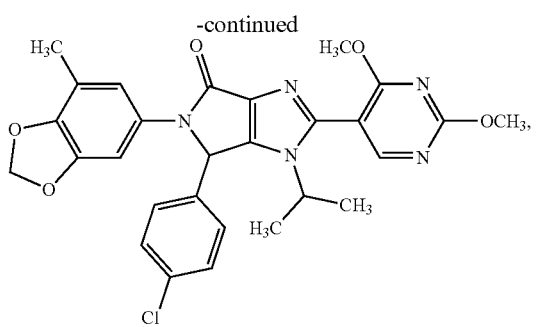
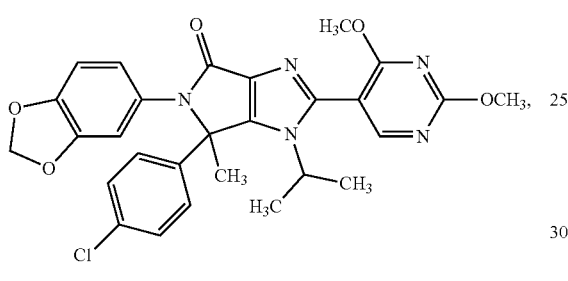
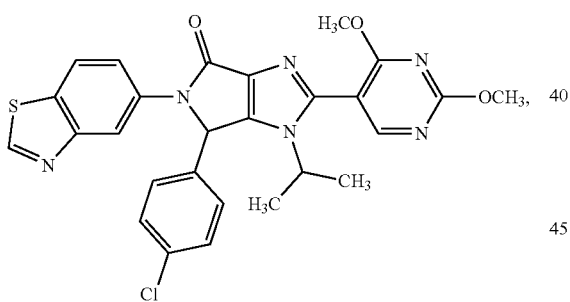
and
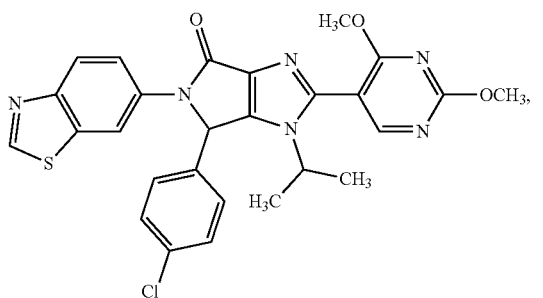
or a pharmaceutically acceptable salt or stereoisomer thereof.
15. The compound as defined in claim 1, or a stereoisomer thereof, wherein the compound, or stereoisomer thereof, is selected from the group consisting of:
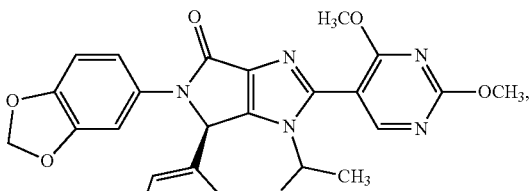
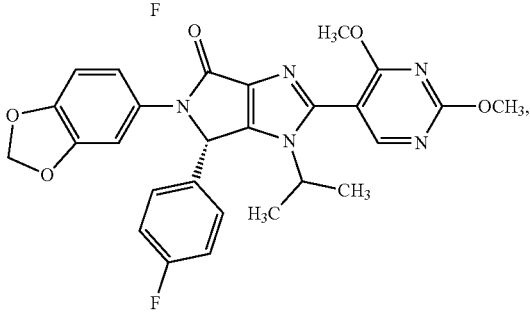
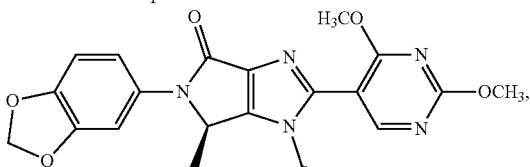
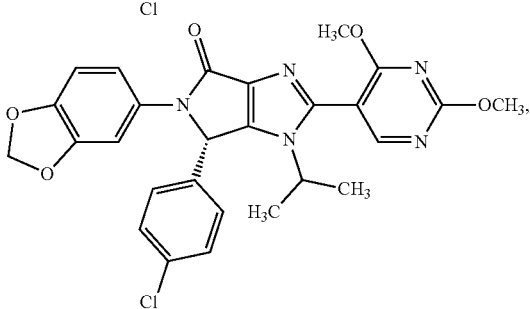
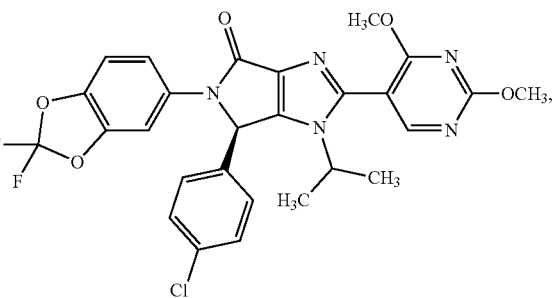

97
-continued
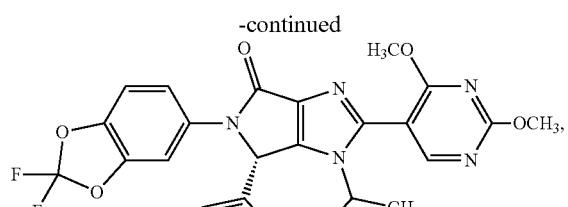
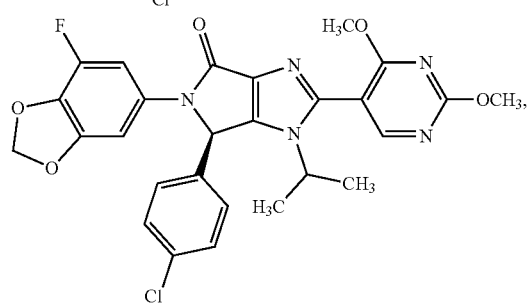
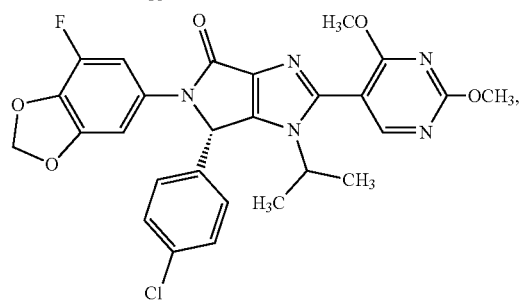
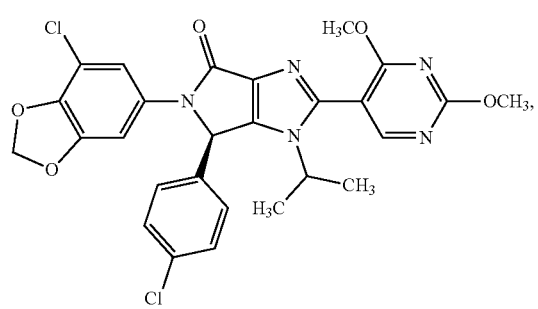
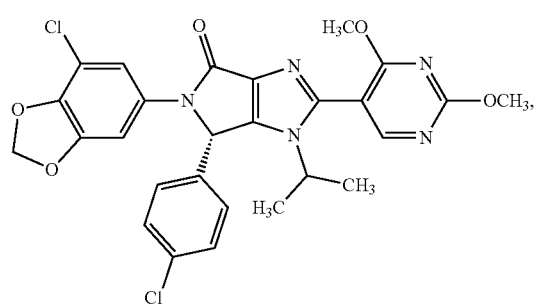
98
-continued
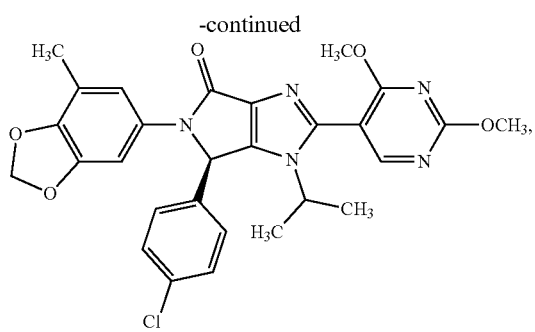
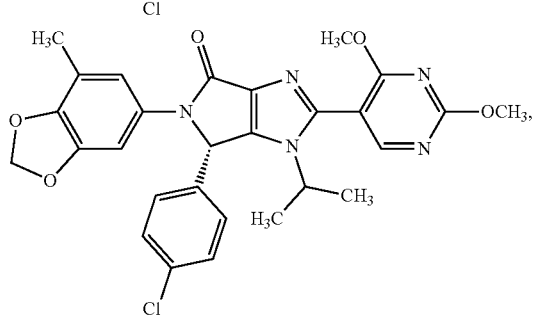
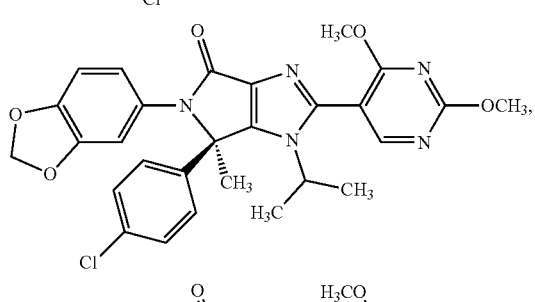
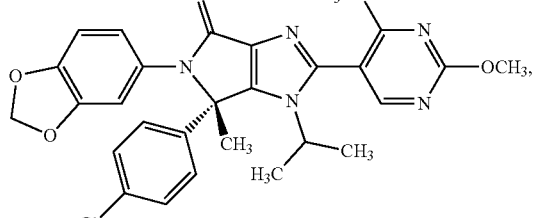
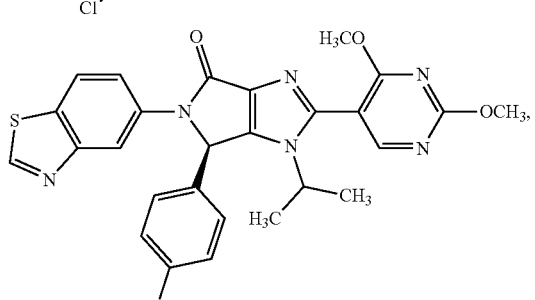
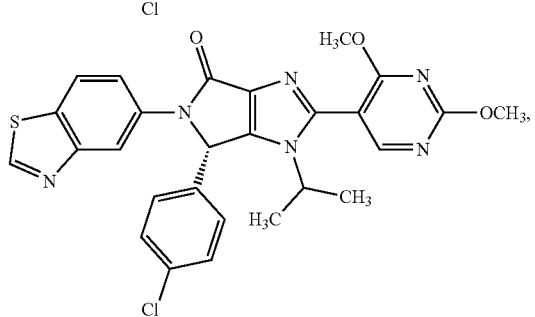

-continued
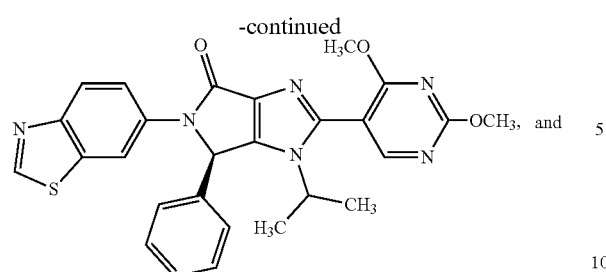
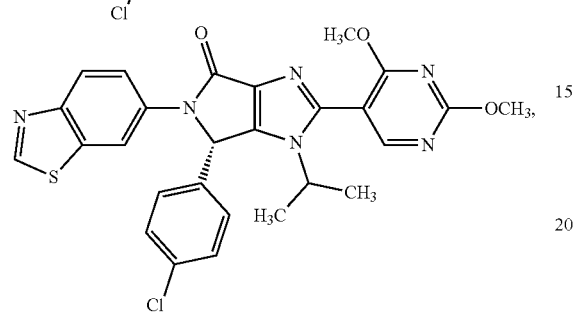
or a pharmaceutically acceptable salt thereof.
* * * * *